US012725686B2

(12) United States Patent
Davelaar et al.

(10) Patent No.: US 12,725,686 B2
(45) Date of Patent: Sep. 1, 2026

(54) MAINTAINING STATE AND CONTEXT OF CONVERSATIONS BETWEEN A USER AND DIGITAL ASSISTANT USING THREADS

(71) Applicant: Oracle International Corporation, Redwood Shores, CA (US)

(72) Inventors: Steven Martijn Davelaar, Utrecht (NL); Jashanpreet Singh, Bengaluru (IN)

(73) Assignee: ORACLE INTERNATIONAL CORPORATION, Redwood Shores, CA (US)

( * ) Notice: Subject to any disclaimer, the term of this patent is extended or adjusted under 35 U.S.C. 154(b) by 0 days.

(21) Appl. No.: 18/885,285

(22) Filed: Sep. 13, 2024

(65) Prior Publication Data

US 2025/0095808 A1 Mar. 20, 2025

Related U.S. Application Data

(60) Provisional application No. 63/583,161, filed on Sep. 15, 2023.

(51) Int. Cl.
*G16H 10/60* (2018.01)
*G06F 3/0482* (2013.01)
(Continued)

(52) U.S. Cl.
CPC ........... *G16H 10/60* (2018.01); *G06F 3/0482* (2013.01); *G06F 3/0483* (2013.01); *G06F 9/453* (2018.02); *G06F 9/546* (2013.01); *G06F 40/30* (2020.01)

(58) Field of Classification Search
CPC ...... G16H 10/60; G16H 10/00; G06F 3/0482; G06F 3/0483; G06F 9/453; G06F 9/546; G06F 40/30
See application file for complete search history.

(56) References Cited

U.S. PATENT DOCUMENTS 10,540,661 B2 1/2020 Lange et al.
11,893,356 B1 2/2024 Yannam et al.
(Continued)

FOREIGN PATENT DOCUMENTS

CN 111258479 B 12/2023

OTHER PUBLICATIONS

Multipurpose Intelligent Process Automation via Conversational Assistant Alena Moiseeva1 , Dietrich Trautmann1 , Michael Heimann2 , Hinrich Schutze 1 arXiv:2001.02284v2 [cs.CL] May 21, 2020 (Year: 2020).*

(Continued)

*Primary Examiner* — Sun M Li
(74) *Attorney, Agent, or Firm* — Kilpatrick Townsend & Stockton LLP

(57) ABSTRACT

Techniques for maintaining state and context of conversations between a user and digital assistant using threads. In one aspect, a method includes receiving a natural language utterance from a user during a session, obtaining a topic context instance for the natural language utterance, and generating, by a GenAI model, a list comprising an executable action based on candidate actions associated with the topic context instance. The executable action is then executed to produce an output. The executing includes determining there is no thread running within the session that is associated with the topic context instance, the executable action, or both, and responsive to determining there is no thread running, creating a thread associated with the topic context instance, the executable action, or both, and executing, using the thread, the executable action to obtain the output. The output or a communication derived from the output is then sent to the user.

20 Claims, 17 Drawing Sheets

(51) Int. Cl.

| | |
|---|---|
| ***G06F 3/0483*** | (2013.01) |
| ***G06F 9/451*** | (2018.01) |
| ***G06F 9/54*** | (2006.01) |
| ***G06F 40/30*** | (2020.01) |

(56) References Cited

U.S. PATENT DOCUMENTS

| | | | | |
|---|---|---|---|---|
| 12,430,329 | B2 * | 9/2025 | Hoang | G06F 40/44 |
| 2018/0068082 | A1 * | 3/2018 | Brown | G10L 15/08 |
| 2018/0324116 | A1 | 11/2018 | Vaduva | |
| 2021/0225507 | A1 * | 7/2021 | Van Kollenburg | G16H 20/30 |
| 2021/0257110 | A1 * | 8/2021 | Barkol | G10L 15/1815 |
| 2021/0303798 | A1 * | 9/2021 | Duong | G06F 40/35 |
| 2022/0308718 | A1 * | 9/2022 | Klein | G10L 15/08 |
| 2022/0374605 | A1 * | 11/2022 | Sethi | G06F 1/3209 |
| 2022/0415320 | A1 * | 12/2022 | Zheng | G06F 40/237 |
| 2023/0135179 | A1 * | 5/2023 | Mielke | G06N 5/022<br>704/232 |
| 2023/0306205 | A1 * | 9/2023 | Maeder | G06F 16/3344 |
| 2023/0419952 | A1 * | 12/2023 | Desai | G06F 40/35 |

OTHER PUBLICATIONS

W. A. H. Weerathunga, G. N. Lokugamage, H. V, A. D. N. H. Yahampath and D. Kasthurirathna, “Domain Specific Conversational Intelligence: Voice Based E-Channeling System,” 2020 2nd International Conference on Advancements in Computing (ICAC), Malabe, Sri Lanka, 2020,pp. 494-499, doi: 10.1109/ICAC51239. (Year: 2020).*

Mairittha T, Mairittha N, Inoue S. Automatic Labeled Dialogue Generation for Nursing Record Systems. J Pers Med. Jul. 16, 2020; 10(3):62. doi: 10.3390/jpm10030062. PMID: 32708593; PMCID: PMC7564988. (Year: 2020).*

Empowering Healthcare Professionals and Patients with ChatGPT: Applications and Challenges, Fatemeh Mosaiyebzadeh, Seyedamin Pouriyeh, Reza M. Pariził, Meng Han 8, Nasrin Dehbozorgi ,Mohsen Dorodchill, Daniel Macêdo Batista*, 979-8-3503-2759-5/23/$31.00 © 2023 IEEE DOI 10.1109/CSCE60160.2023.00233 (Year: 2023).*

Mosaiyebzadeh , et al., “Empowering Healthcare Professionals and Patients With Chatgpt: Applications and Challenges”, 2023 Congress in Computer Science, Computer Engineering, & Applied Computing (CSCE), Jul. 24, 2023, 7 pages.

International Application No. PCT/US2024/046761 , “International Search Report and Written Opinion”, Dec. 6, 2024, 14 pages.

“ACL Chatbot”, ALTEN Calsoft Labs Chatbot Solutions, Product Innovation, ALTEN Calsoft Labs Digital, Available online at: https://www.acldigital.com/offerings/product-innovation-and-engineering/acl-chatbot, Accessed from Internet on May 8, 2024, pp. 1-3.

“Get Better Answers by Setting the Context for Github Copilot Chat in Visual Studio”, Tips & Tricks for GitHub Copilot Chat in Visual Studio—Visual Studio (Windows), Available online at: https://learn.microsoft.com/en-us/visualstudio/ide/copilot-chat-context?view=vs-2022#threads, Mar. 20, 2024, pp. 1-8.

“MicroStrategy AI”, MicroStrategy AI Apps—AI Chatbots, AI Dashboards, AI Analytics, Available online at: https://www.microstrategy.com/enterprise-analytics/ai-chatbot-for-apps, Accessed from Internet on May 8, 2024, pp. 1-12.

“The askNivi Platform”, Nivi, Available online at: https://www.nivi.io/platform, Accessed from Internet on May 8, 2024, pp. 1-3.

Hong, et al., “Conversational AI Threads for Visualizing Multidimensional Datasets”, Available online at: https://arxiv.org/pdf/2311.05590, Nov. 9, 2023, pp. 1-37.

Manske, “Building a Micro Chatbot Platform”, Available online at: https://innv.northwesternmutual.com/blog/building-a-micro-chatbot-platform, Jan. 3, 2019, pp. 1-5.

Yu, et al., “Chatlang: A Two-window Approach to Chatbots for Language Learning”, Available online at: https://anrg.usc.edu/www/papers/chatlang.pdf, Sep. 21, 2023, pp. 1-6.

* cited by examiner

```
{
    "create.skill": {
        "$schema": "http: //json-schema.org/draft-07/schema#",
        "additionalProperties": false,
        "type": "object",
        "properties": {
                "skillName": {
                    "type": "string"
                },
                "skillPurpose": {
                    "type": "string"
                },
                "promptForMissingInformation": {
                    "type": "string"
                }
        },
          "required": [ ]
    },
    "create.intent": {
        "$schema": "http: //json-schema.org/draft-07/schema#",
        "additionalProperties": false,
        "type": "object",
        "properties": {
                "intentName": {
                    "type": "string"
                },
                "intentPurpose": {
                    "type": "string"
```

FIG. 11

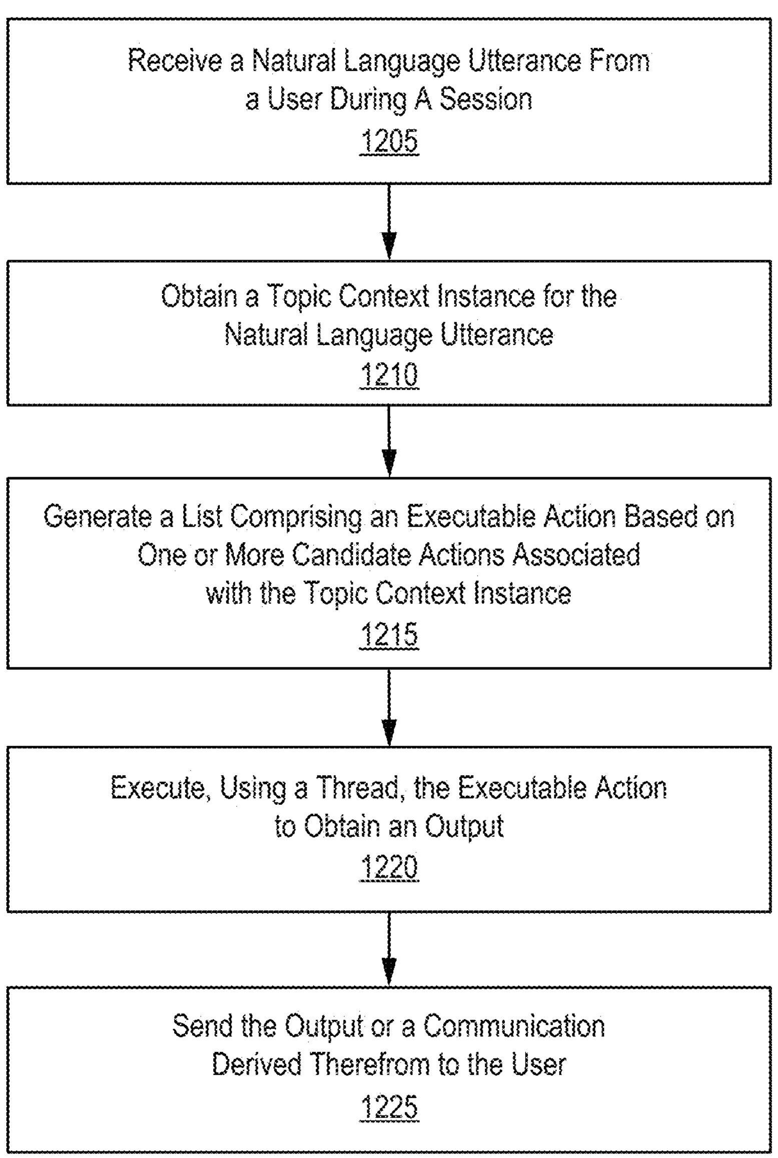
FIG. 12

MAINTAINING STATE AND CONTEXT OF CONVERSATIONS BETWEEN A USER AND DIGITAL ASSISTANT USING THREADS

CROSS-REFERENCE TO RELATED APPLICATION

The present application is a non-provisional application of and claims the benefit and priority under 35 U.S.C. 119(e) to U.S. Provisional Application No. 63/583,161, filed Sep. 15, 2023, the entire contents of which are incorporated herein by reference for all purposes.

FIELD

The present disclosure relates generally to artificial intelligence techniques, and more particularly, to techniques for maintaining state and context of conversations between a user and digital assistant using threads.

BACKGROUND

Artificial intelligence (AI) has a multitude of applications, and one example is its use in instant messaging or chat platforms to provide instant responses. Organizations leverage these platforms to engage with customers in real-time conversations, but hiring human service agents for this purpose can be prohibitively expensive. To address this, chatbots—automated programs designed to simulate human conversation have been developed, particularly for internet use. These chatbots can be integrated into existing messaging apps that users are already familiar with. Initially, the chatbots were simple programs designed to simulate conversation with users through text-based interactions, often following predefined scripts with limited capabilities. These early chatbots were primarily used for basic customer service tasks, such as answering frequently asked questions or providing information about products and services.

The evolution of chatbots into more sophisticated chatbot systems such as digital assistants have been driven by advancements in AI and the growing need for more sophisticated and interactive user experiences. More specifically, as AI technologies, particularly Natural Language Processing (NLP) and Machine Learning (ML), advanced, chatbots began to evolve into more intelligent and context-aware systems. NLP enabled chatbots to understand and process human language more effectively, allowing them to comprehend context, manage ambiguity, and handle diverse linguistic nuances. This shift allowed chatbots to engage in more natural and meaningful conversations, moving beyond simple keyword-based interactions to understanding user intent and providing more relevant responses. ML enabled chatbots to understand voice commands, interact with various applications and services, manage schedules, control smart devices, and provide personalized recommendations. The continuous learning and adaptation capabilities of AI ensure that chatbots can evolve with user needs and preferences, offering a more seamless and intuitive user experience. This evolution from simple chatbots to sophisticated chatbot systems represents a significant leap in AI's ability to enhance daily life and business operations.

BRIEF SUMMARY

In various embodiments, a computer-implemented method includes: receiving, at a digital assistant, a natural language utterance from a user during a session between the user and the digital assistant; obtaining a topic context instance for the natural language utterance; generating, by a generative artificial intelligence (GenAI) model, a list comprising an executable action based on one or more candidate actions associated with the topic context instance; executing the executable action to produce an output, wherein the executing comprises: determining there is no thread running within the session that is associated with the topic context instance, the executable action, or both, responsive to determining there is no thread running, creating a thread associated with the topic context instance, the executable action, or both, wherein the thread maintains the topic context instance, the executable action, or both as a separate context from that of context associated with any other conversations for a distinct conversation comprising the natural language utterance between the user and the digital assistant, and executing, using the thread, the executable action to obtain the output; and sending the output or a communication derived from the output to the user.

In some embodiments, the computer-implemented method further includes: receiving, at the digital assistant, a subsequent natural language utterance from the user during the session between the user and the digital assistant; obtaining the topic context instance for the natural language utterance; generating, by the GenAI model, another list comprising another executable action based on one or more candidate actions associated with the topic context instance; executing the another executable action, wherein the executing comprises: identifying the thread running within the session is associated with the topic context instance, the executable action, or both, determining the another executable action should be executed using the thread based on an identifier associated with the topic context instance, the executable action, or both, and executing, using the thread, the another executable action to obtain another output; and sending the another output or a communication derived from the another output to the user.

In some embodiments, the computer-implemented method further includes: receiving, at the digital assistant, a subsequent natural language utterance from the user during the session between the user and the digital assistant; obtaining a topic context instance for the subsequent natural language; generating, by the GenAI model, another list comprising another executable action based on one or more candidate actions associated with the topic context instance for the subsequent natural language utterance; executing the another executable action, wherein the executing comprises: identifying the thread running within the session is associated with the topic context instance for the natural language utterance, the executable action, or both, determining there is no thread running within the session that is associated with the topic context instance for the subsequent natural language utterance, the another executable action, or both, responsive to determining there is no thread running within the session that is associated with the topic context instance for the subsequent natural language utterance, creating another thread having an identifier associated with the topic context instance for the subsequent natural language utterance, the another executable action, or both, wherein the another thread maintains the topic context instance for the subsequent natural language utterance, the another executable action, or both as a separate context for another distinct conversation between the user and the digital assistant, and executing, using the another thread, the another executable action to obtain another output; and sending the another output or a communication derived from the another output to the user.

In some embodiments, the computer-implemented method further includes: responsive to identifying the thread running within the session is associated with the topic context instance for the natural language utterance, the executable action, or both and determining there is no thread running within the session that is associated with the topic context instance for the subsequent natural language utterance, sending a confirmation communication to the user requesting confirmation of the subsequent natural language utterance, the topic context instance for the subsequent natural language utterance, or both; and receiving, at the digital assistant, a confirmation utterance from the user that confirms the subsequent natural language utterance, the topic context instance for the subsequent natural language utterance, or both, wherein responsive to determining there is no thread running within the session that is associated with the topic context instance for the subsequent natural language utterance and receipt of the confirmation utterance, creating the another thread.

In some embodiments, the computer-implemented method further includes receiving a message payload comprising: (i) a subsequent utterance or indication of an event, and (ii) application context, associated with an interaction between a user and an application; identifying an identifier associated with the subsequent utterance or the indication of the interface action, (ii) the application context, or (iii) both; determining the identifier associated with the subsequent utterance or the indication of the interface action, (ii) the application context, or (iii) both is the same identifier associated with the topic context instance, the executable action, or both; and responsive to determining the identifiers are the same, processing the message payload using the thread.

In some embodiments, the computer-implemented method further includes: receiving a message payload comprising: (i) a subsequent utterance or indication of an event, and (ii) application context, associated with an interaction between a user and an application; identifying an identifier associated with (i) the subsequent utterance or the indication of the interface action, (ii) the application context, or (iii) both; determining the identifier associated with (i) the subsequent utterance or the indication of the interface action, (ii) the application context, or (iii) both is different from an identifier associated with the topic context instance, the executable action, or both; and responsive to determining the identifiers are different, creating another thread having an identifier associated with (i) the subsequent utterance or the indication of the interface action, (ii) the application context, or (iii) both, wherein the another thread maintains (i) the subsequent utterance or the indication of the interface action, (ii) the application context, or (iii) both as a separate context for another distinct conversation between the user and the digital assistant; and processing the message payload using the another thread.

In some embodiments, the computer-implemented method further includes: responsive to determining the identifiers are different, sending a confirmation communication to the user requesting confirmation of (i) the subsequent utterance or the indication of the interface action, (ii) the application context, or (iii) both; and receiving, at the digital assistant, a confirmation utterance from the user that confirms (i) the subsequent utterance or the indication of the interface action, (ii) the application context, or (iii) both, wherein responsive to determining the identifiers are different and receipt of the confirmation utterance, creating the another thread.

In some embodiments, a system is provided that includes one or more processors and one or more computer-readable media storing instructions which, when executed by the one or more processors, cause the system to perform part or all of the operations and/or methods disclosed herein.

In some embodiments, one or more non-transitory computer-readable media are provided for storing instructions which, when executed by one or more processors, cause a system to perform part or all of the operations and/or methods disclosed herein.

The techniques described above and below may be implemented in a number of ways and in a number of contexts. Several example implementations and contexts are provided with reference to the following figures, as described below in more detail. However, the following implementations and contexts are but a few of many.

BRIEF DESCRIPTION OF THE DRAWINGS

FIG. 11 illustrates an exemplary schema payload (e.g., JSON payload) required to generate digital assistant artefacts in accordance with various embodiments.

FIG. 12 is a flowchart of a process for maintaining state and context of conversations between a user and digital assistant using threads in accordance with various embodiments.

DETAILED DESCRIPTION

Figure 1:
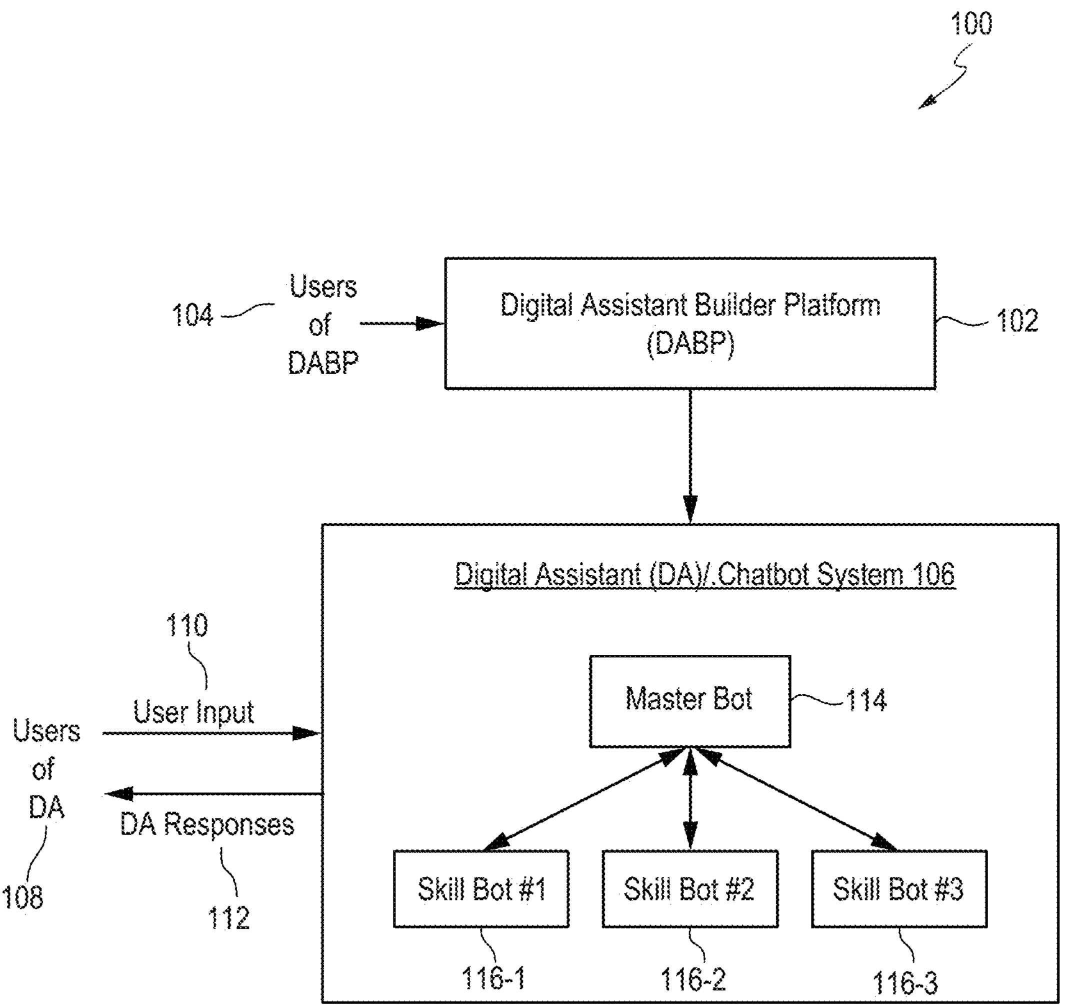
FIG. 1 is a simplified block diagram of a distributed environment in accordance with various embodiments.

In the following description, for the purposes of explanation, specific details are set forth in order to provide a thorough understanding of some embodiments. However, it will be apparent that various embodiments may be practiced without these specific details. The figures and description are not intended to be restrictive. The word "exemplary" is used herein to mean "serving as an example, instance, or illustration." Any embodiment or design described herein as "exemplary" is not necessarily to be construed as preferred or advantageous over other embodiments or designs.

Introduction

Artificial intelligence has many applications. For example, a digital assistant is an artificial intelligence-driven interface that helps users accomplish a variety of tasks using natural language conversations. For each digital assistant, a customer may assemble one or more skills. Skills (also described herein as chatbots, bots, or skill bots) are individual bots that are focused on specific types of tasks, such as tracking inventory, submitting timecards, and creating expense reports. When an end user engages with the digital assistant, the digital assistant evaluates the end user input and routes the conversation to and from the appropriate chatbot. The digital assistant can be made available to end users through a variety of channels such as FACEBOOK® Messenger, SKYPE MOBILE® messenger, or a Short Message Service (SMS). Channels carry the chat back and forth from end users on various messaging platforms to the digital assistant and its various chatbots. The channels may also support user agent escalation, event-initiated conversations, and testing.

Intents allow artificial intelligence-based technology such as a chatbot to understand what the user wants the chatbot to do. Intents are the user's intention communicated to the chatbot via user requests and statements, which are also referred to as utterances (e.g., get account balance, make a purchase, etc.). As used herein, an utterance or a message may refer to a set of words (e.g., one or more sentences) exchanged during a conversation with a chatbot. Intents may be created by providing a name that illustrates some user action (e.g., order a pizza) and compiling a set of real-life user statements, or utterances that are commonly associated with triggering the action. Because the chatbot's cognition is derived from these intents, each intent may be created from a data set that is robust (one to two dozen utterances) and varied, so that the chatbot may interpret ambiguous user input. A rich set of utterances enables a chatbot to understand what the user wants when it receives messages like "Forget this order!" or "Cancel delivery!"—messages that mean the same thing, but are expressed differently. Collectively, the intents, and the utterances that belong to them, make up a training corpus for the chatbot. By training a model with the corpus, a customer may essentially turn that model into a reference tool for resolving end user input to a single intent. A customer can improve the acuity of the chatbot's cognition through rounds of intent testing and intent training.

Once an intent of the user is understood by the chatbot, the chatbot can execute a dialog flow. A flow is a piece of the skill dialog flow that defines the interaction with the user to complete a task or a part of a task that the user wants to perform. Typical examples of flows include:

- Intent-driven flows, where each intent defined in the skill has an associated flow, for example 'Order Pizza', 'Send Money' or 'Create Expense'.
- Supporting or utility flows for tasks like user authorization, new user onboarding, logging, or providing user assistance. Such flows can be invoked from multiple flows. For example, you could have a Create Account sub-flow that you invoke from flows like Order Pizza or Send Money.

Generally speaking, flows break down into the following types: Main Flow, Intent flows, Flows for built-in events and system transitions, and Sub-flows that can be used by top-level flows. The main flow isn't really a flow as such. Rather, it is the control center for the skill, from where users are directed to specialized flows that are mapped to the intents. Within the intent and sub-flows various actions may be defined for supporting what the user wants the chatbot to do in accordance with the understood intent. The various actions can include conversation dialogue, execution of queries on databases, sentiment analysis, data analysis, API and REST calls, and the like.

More recently, Large Language Models (LLMs) have been integrated into digital assistants to enhance skills with generative AI capabilities. These capabilities include handling small talk with a user, generating written summaries of data, automating challenging or repetitive business tasks, such as those required for talent acquisition, and providing sentiment analysis of a given piece of text to determine whether it reflects a positive, negative, or neutral opinion. Using the Invoke Large Language Model component (the LLM component), a skill bot developer can plug these capabilities into their dialog flow wherever they're needed. This dialog flow component is the primary integration piece for generative AI in that it contacts the LLM through a call (e.g., REST call), then sends the LLM a prompt (the natural language instructions to the LLM) along with related parameters. It then returns the results generated by the model (which are also known as completions) and manages the state of the LLM-user interactions so that its responses remain in context after successive rounds of user queries and feedback. The LLM component can call any LLM. A user can add one or more LLM component states (or LLM blocks) to flows. A user can also chain the LLM calls so that the output of one LLM request can be passed to a subsequent LLM request.

Copilot represents a new generation of innovative user experiences aimed at enhancing application (e.g., business application) usage. With the digital assistant framework, developers can create customized digital assistants comprising multiple skills, including specialized functionalities such as a ready-to-use digital assistant, which has skills like Expenses, Project Management, Human Capital Management (HCM) and more. As discussed herein, skill developers now have the ability to incorporate generative AI components such as LLMs into their skill flows which allow them to introduce generative AI capability into their existing digital assistant. With blended capabilities of the digital assistant, copilot can seamlessly integrate with applications, thus providing conversational AI and generative AI tailored experience to users' needs while using applications for various tasks. The challenge is developing/configuring the copilot such that it can be used irrespective of the application upon which it is being integrated. If the copilot is not usable across various applications, then it may break if an application or version of an application changes.

In order to address this challenge and others, the copilot platform is developed/configured with a relatively loose coupling between digital assistant (DA) and application using various technical techniques including context passing, interaction modalities (side panel chat and micro conversation chat), and copilot actions. Context passing involves obtaining context from the application, pages displayed by the application, and the user using the application in order for the copilot to better understand the situation and work with the DA to provide the most relevant information concerning the application to the user. The interaction modalities are interfaces for the user to interact with the copilot while still viewing the application and include a side-panel chat and a micro conversation chat. Copilot actions are actions performed or triggered by copilot and used to control views and information within the application. These technical techniques (described in greater detail herein) enable context-aware personalized journeys for the users of applications, proactively assists the users with certain suggestions or actions, assists with content generation and formatting, and makes application navigation and dynamic updates smooth for the users.

In order to allow for or maintaining state and context of conversations between a user and the DA, threads are used. Threading is maintaining multiple isolated conversations within a same session between a user and digital assistant. The thread identifier is main concept to switch between and determine which thread is being used or should be used. Threads are initiated as part of an executable action identified via a GenAI model such as an LLM. Alternatively, threads are initiated as part of an executable action directly identified via a UI event. The executable action has a thread ID configuration such as when specific to patient records, the thread ID=patient name [-] patient ID. The threads maintain state with conversation or task context for a particular dialogue or flow, which includes all utterances, responses, actions executed, etc. The conversation or task context is stored in the context memory store in association with the thread ID. The thread manager handles all thread IDs, states, and switching. Threading has the benefit of ensuring that utterances and actions are all grouped based on a given domain such as a patient identifier (e.g., a doctor cannot mistakenly mix data/information between patients). Threads can also be separated based on multiple domains such as per patient and per action. An ancillary technical challenge is knowing when to switch threads especially when the utterance does not match context. So, the dialogue may include a confirmation sent to user making sure they wish to switch threads.

In an exemplary embodiment, a computer-implemented method includes: receiving, at a digital assistant, a natural language utterance from a user during a session between the user and the digital assistant; obtaining a topic context instance for the natural language utterance; generating, by a generative artificial intelligence (GenAI) model, a list comprising an executable action based on one or more candidate actions associated with the topic context instance; executing the executable action to produce an output, wherein the executing comprises: determining there is no thread running within the session that is associated with the topic context instance, the executable action, or both, responsive to determining there is no thread running, creating a thread associated with the topic context instance, the executable action, or both, wherein the thread maintains the topic context instance, the executable action, or both as a separate context from that of context associated with any other conversations for a distinct conversation comprising the natural language utterance between the user and the digital assistant, and executing, using the thread, the executable action to obtain the output; and sending the output or a communication derived from the output to the user.

As used herein, the articles 'a' and 'an' are used herein to refer to one or to more than one (i.e. at least one) of the grammatical object of the article. By way of example, an element means at least one element and can include more than one element.

As used herein, the terms "about," "similarly," "substantially," and "approximately" are defined as being largely but not necessarily wholly what is specified (and include wholly what is specified) as understood by one of ordinary skill in the art. In any disclosed embodiment, the term "about," "similarly," "substantially," or "approximately" may be substituted with "within [a percentage] of" what is specified, where the percentage includes 0.1 percent, 1 percent, 5 percent, and 10 percent, etc. Moreover, the term terms "about," "similarly," "substantially," and "approximately" are used to provide flexibility to a numerical range endpoint by providing that a given value may be slightly above or slightly below the endpoint without affecting the desired result.

As used herein, when an action is "based on" something, this means the action can be based at least in part on at least a part of the something.

The use herein of the terms including, comprising, or having, and variations thereof, is meant to encompass the elements listed thereafter and equivalents thereof as well as additional elements. Embodiments recited as including, comprising, or having certain elements are also contemplated as consisting essentially of and consisting of those certain elements. As used herein, and/or, refers to and encompasses any and all possible combinations of one or more of the associated listed items, as well as the lack of combinations were interpreted in the alternative (or).

Bot and Analytic Systems (Skill Track)

A bot (also referred to as a skill, chatbot, chatterbot, or talkbot) is a computer program that can perform conversations with end users. The bot can generally respond to natural-language messages (e.g., questions or comments) through a messaging application that uses natural-language messages. Enterprises may use one or more bot systems to communicate with end users through a messaging application. The messaging application, which may be referred to as a channel, may be an end user preferred messaging application that the end user has already installed and familiar with. Thus, the end user does not need to download and install new applications in order to chat with the bot system. The messaging application may include, for example, over-the-top (OTT) messaging channels (such as Facebook Messenger, Facebook WhatsApp, WeChat, Line, Kik, Telegram, Talk, Skype, Slack, or SMS), virtual private assistants (such as Amazon Dot, Echo, or Show, Google Home, Apple HomePod, etc.), mobile and web app extensions that extend native or hybrid/responsive mobile apps or web applications with chat capabilities, or voice based input (such as devices or apps with interfaces that use Siri, Cortana, Google Voice, or other speech input for interaction).

In some examples, a bot system may be associated with a Uniform Resource Identifier (URI). The URI may identify the bot system using a string of characters. The URI may be used as a webhook for one or more messaging application systems. The URI may include, for example, a Uniform Resource Locator (URL) or a Uniform Resource Name (URN). The bot system may be designed to receive a message (e.g., a hypertext transfer protocol (HTTP) post call message) from a messaging application system. The HTTP post call message may be directed to the URI from the messaging application system. In some embodiments, the message may be different from a HTTP post call message. For example, the bot system may receive a message from a Short Message Service (SMS). While discussion herein may refer to communications that the bot system receives as a message, it should be understood that the message may be an HTTP post call message, a SMS message, or any other type of communication between two systems.

End users may interact with the bot system through a conversational interaction (sometimes referred to as a conversational user interface (UI)), just as interactions between people. In some cases, the interaction may include the end user saying "Hello" to the bot and the bot responding with a "Hi" and asking the end user how it can help. In some cases, the interaction may also be a transactional interaction with, for example, a banking bot, such as transferring money from one account to another; an informational interaction with, for example, a HR bot, such as checking for vacation balance; or an interaction with, for example, a retail bot, such as discussing returning purchased goods or seeking technical support.

In some embodiments, the bot system may intelligently handle end user interactions without interaction with an administrator or developer of the bot system. For example, an end user may send one or more messages to the bot system in order to achieve a desired goal. A message may include certain content, such as text, emojis, audio, image, video, or other method of conveying a message. In some embodiments, the bot system may convert the content into a standardized form (e.g., a representational state transfer (REST) call against enterprise services with the proper parameters) and generate a natural language response. The bot system may also prompt the end user for additional input parameters or request other additional information. In some embodiments, the bot system may also initiate communication with the end user, rather than passively responding to end user utterances. Described herein are various techniques for identifying an explicit invocation of a bot system and determining an input for the bot system being invoked. In some embodiments, explicit invocation analysis is performed by a master bot based on detecting an invocation name in an utterance. In response to detection of the invocation name, the utterance may be refined for input to a skill bot associated with the invocation name.

A conversation with a bot may follow a specific conversation flow including multiple states. The flow may define what would happen next based on an input. In some embodiments, a state machine that includes user defined states (e.g., end user intents) and actions to take in the states or from state to state may be used to implement the bot system. A conversation may take different paths based on the end user input, which may impact the decision the bot makes for the flow. For example, at each state, based on the end user input or utterances, the bot may determine the end user's intent in order to determine the appropriate next action to take. As used herein and in the context of an utterance, the term "intent" refers to an intent of the user who provided the utterance. For example, the user may intend to engage a bot in conversation for ordering pizza, so that the user's intent could be represented through the utterance "Order pizza." A user intent can be directed to a particular task that the user wishes a chatbot to perform on behalf of the user. Therefore, utterances can be phrased as questions, commands, requests, and the like, that reflect the user's intent. An intent may include a goal that the end user would like to accomplish.

In the context of the configuration of a chatbot, the term "intent" is used herein to refer to configuration information for mapping a user's utterance to a specific task/action or category of task/action that the chatbot can perform. In order to distinguish between the intent of an utterance (i.e., a user intent) and the intent of a chatbot, the latter is sometimes referred to herein as a "bot intent." A bot intent may comprise a set of one or more utterances associated with the intent. For instance, an intent for ordering pizza can be communicated by various permutations of utterances that express a desire to place an order for pizza. These associated utterances can be used to train an intent classifier of the chatbot to enable the intent classifier to subsequently determine whether an input utterance from a user matches the order pizza intent. A bot intent may be associated with one or more dialog flows for starting a conversation with the user and in a certain state. For example, the first message for the order pizza intent could be the question "What kind of pizza would you like?" In addition to associated utterances, a bot intent may further comprise named entities that relate to the intent. For example, the order pizza intent could include variables or parameters used to perform the task of ordering pizza, e.g., topping 1, topping 2, pizza type, pizza size, pizza quantity, and the like. The value of an entity is typically obtained through conversing with the user.

FIG. 1 is a simplified block diagram of an environment 100 incorporating a chatbot system according to some embodiments. Environment 100 comprises a digital assistant builder platform (DABP) 102 that enables users of DABP 102 to create and deploy digital assistants or chatbot systems. DABP 102 can be used to create one or more digital assistants (or DAs) or chatbot systems. For example, as shown in FIG. 1, user 104 representing a particular enterprise can use DABP 102 to create and deploy a digital assistant 106 for users of the particular enterprise. For example, DABP 102 can be used by a bank to create one or more digital assistants for use by the bank's customers. The same DABP 102 platform can be used by multiple enterprises to create digital assistants. As another example, an owner of a restaurant (e.g., a pizza shop) may use DABP 102 to create and deploy a digital assistant that enables customers of the restaurant to order food (e.g., order pizza).

For purposes of this disclosure, a "digital assistant" is an entity that helps users of the digital assistant accomplish various tasks through natural language conversations. A digital assistant can be implemented using software only (e.g., the digital assistant is a digital entity implemented using programs, code, or instructions executable by one or more processors), using hardware, or using a combination of hardware and software. A digital assistant can be embodied or implemented in various physical systems or devices, such as in a computer, a mobile phone, a watch, an appliance, a vehicle, and the like. A digital assistant is also sometimes referred to as a chatbot system. Accordingly, for purposes of this disclosure, the terms digital assistant and chatbot system are interchangeable.

A digital assistant, such as digital assistant 106 built using DABP 102, can be used to perform various tasks via natural language-based conversations between the digital assistant and its users 108. As part of a conversation, a user may provide one or more user inputs 110 to digital assistant 106 and get responses 112 back from digital assistant 106. A conversation can include one or more of inputs 110 and responses 112. Via these conversations, a user can request one or more tasks to be performed by the digital assistant and, in response, the digital assistant is configured to perform the user-requested tasks and respond with appropriate responses to the user.

User inputs 110 are generally in a natural language form and are referred to as utterances. A user utterance 110 can be in text form, such as when a user types in a sentence, a question, a text fragment, or even a single word and provides it as input to digital assistant 106. In some embodiments, a user utterance 110 can be in audio input or speech form, such as when a user says or speaks something that is provided as input to digital assistant 106. The utterances are typically in a language spoken by the user 108. For example, the utterances may be in English, or some other language. When an utterance is in speech form, the speech input is converted to text form utterances in that particular language and the text utterances are then processed by digital assistant 106. Various speech-to-text processing techniques may be used to convert a speech or audio input to a text utterance, which is then processed by digital assistant 106. In some embodiments, the speech-to-text conversion may be done by digital assistant 106 itself.

An utterance, which may be a text utterance or a speech utterance, can be a fragment, a sentence, multiple sentences, one or more words, one or more questions, combinations of the aforementioned types, and the like. Digital assistant 106 may be configured to apply natural language understanding (NLU) techniques to the utterance to understand the meaning of the user input. As part of the NLU processing for an utterance, digital assistant 106 may be configured to perform processing to understand the meaning of the utterance, which involves identifying one or more intents and one or more entities corresponding to the utterance. Upon understanding the meaning of an utterance, digital assistant 106 may perform one or more actions or operations responsive to the understood meaning or intents. For purposes of this disclosure, it is assumed that the utterances are text utterances that have been provided directly by a user 108 of digital assistant 106 or are the results of conversion of input speech utterances to text form. This however is not intended to be limiting or restrictive in any manner.

For example, a user 108 input may request a pizza to be ordered by providing an utterance such as "I want to order a pizza." Upon receiving such an utterance, digital assistant 106 is configured to understand the meaning of the utterance and take appropriate actions. The appropriate actions may involve, for example, responding to the user with questions requesting user input on the type of pizza the user desires to order, the size of the pizza, any toppings for the pizza, and the like. The responses provided by digital assistant 106 may also be in natural language form and typically in the same language as the input utterance. As part of generating these responses, digital assistant 106 may perform natural language generation (NLG). For the user ordering a pizza, via the conversation between the user and digital assistant 106, the digital assistant may guide the user to provide all the requisite information for the pizza order, and then at the end of the conversation cause the pizza to be ordered. Digital assistant 106 may end the conversation by outputting information to the user indicating that the pizza has been ordered.

At a conceptual level, digital assistant 106 performs various processing in response to an utterance received from a user. In some embodiments, this processing involves a series or pipeline of processing steps including, for example, understanding the meaning of the input utterance (sometimes referred to as Natural Language Understanding (NLU), determining an action to be performed in response to the utterance, where appropriate causing the action to be performed, generating a response to be output to the user responsive to the user utterance, outputting the response to the user, and the like. The NLU processing can include parsing the received input utterance to understand the structure and meaning of the utterance, refining and reforming the utterance to develop a better understandable form (e.g., logical form) or structure for the utterance. Generating a response may include using NLG techniques.

The NLU processing performed by a digital assistant, such as digital assistant 106, can include various NLP related processing such as sentence parsing (e.g., tokenizing, lemmatizing, identifying part-of-speech tags for the sentence, identifying named entities in the sentence, generating dependency trees to represent the sentence structure, splitting a sentence into clauses, analyzing individual clauses, resolving anaphoras, performing chunking, and the like). In some embodiments, the NLU processing or portions thereof is performed by digital assistant 106 itself. In some other embodiments, digital assistant 106 may use other resources to perform portions of the NLU processing. For example, the syntax and structure of an input utterance sentence may be identified by processing the sentence using a parser, a part-of-speech tagger, and/or a named entity recognizer. In one implementation, for the English language, a parser, a part-of-speech tagger, and a named entity recognizer such as ones provided by the Stanford Natural Language Processing (NLP) Group are used for analyzing the sentence structure and syntax. These are provided as part of the Stanford CoreNLP toolkit.

While the various examples provided in this disclosure show utterances in the English language, this is meant only as an example. In some embodiments, digital assistant 106 is also capable of handling utterances in languages other than English. Digital assistant 106 may provide subsystems (e.g., components implementing NLU functionality) that are configured for performing processing for different languages. These subsystems may be implemented as pluggable units that can be called using service calls from an NLU core server. This makes the NLU processing flexible and extensible for each language, including allowing different orders of processing. A language pack may be provided for individual languages, where a language pack can register a list of subsystems that can be served from the NLU core server.

A digital assistant, such as digital assistant 106 depicted in FIG. 1, can be made available or accessible to its users 108 through a variety of different channels, such as but not limited to, via certain applications, via social media platforms, via various messaging services and applications, and other applications or channels. A single digital assistant can have several channels configured for it so that it can be run on and be accessed by different services simultaneously.

A digital assistant or chatbot system generally contains or is associated with one or more skills. In some embodiments, these skills are individual chatbots (referred to as skill bots) that are configured to interact with users and fulfill specific types of tasks, such as tracking inventory, submitting timecards, creating expense reports, ordering food, checking a bank account, making reservations, buying a widget, and the like. For example, for the embodiment depicted in FIG. 1, digital assistant or chatbot system 106 includes skills 116-1, 116-2, and so on. For purposes of this disclosure, the terms "skill" and "skills" are used synonymously with the terms "skill bot" and "skill bots", respectively.

Each skill associated with a digital assistant helps a user of the digital assistant complete a task through a conversation with the user, where the conversation can include a combination of text or audio inputs provided by the user and responses provided by the skill bots. These responses may be in the form of text or audio messages to the user and/or using simple user interface elements (e.g., select lists) that are presented to the user for the user to make selections.

There are various ways in which a skill or skill bot can be associated or added to a digital assistant. In some instances, a skill bot can be developed by an enterprise and then added to a digital assistant using DABP 102. In other instances, a skill bot can be developed and created using DABP 102 and then added to a digital assistant created using DABP 102. In yet other instances, DABP 102 provides an online digital store (referred to as a "skills store") that offers multiple skills directed to a wide range of tasks. The skills offered through the skills store may also expose various cloud services. In order to add a skill to a digital assistant being generated using DABP 102, a user of DABP 102 can access the skills store via DABP 102, select a desired skill, and indicate that the selected skill is to be added to the digital assistant created using DABP 102. A skill from the skills store can be added to a digital assistant as is or in a modified form (for example, a user of DABP 102 may select and clone a particular skill bot provided by the skills store, make customizations or modifications to the selected skill bot, and then add the modified skill bot to a digital assistant created using DABP 102).

Various different architectures may be used to implement a digital assistant or chatbot system. For example, in some embodiments, the digital assistants created and deployed using DABP 102 may be implemented using a master bot/child (or sub) bot paradigm or architecture. According to this paradigm, a digital assistant is implemented as a master bot that interacts with one or more child bots that are skill bots. For example, in the embodiment depicted in FIG. 1, digital assistant 106 comprises a master bot 114 and skill bots 116-1, 116-2, etc. that are child bots of master bot 114. In some embodiments, digital assistant 106 is itself considered to act as the master bot.

A digital assistant implemented according to the master-child bot architecture enables users of the digital assistant to interact with multiple skills through a unified user interface, namely via the master bot. When a user engages with a digital assistant, the user input is received by the master bot. The master bot then performs processing to determine the meaning of the user input utterance. The master bot then determines whether the task requested by the user in the utterance can be handled by the master bot itself, else the master bot selects an appropriate skill bot for handling the user request and routes the conversation to the selected skill bot. This enables a user to converse with the digital assistant through a common single interface and still provide the capability to use several skill bots configured to perform specific tasks. For example, for a digital assistance developed for an enterprise, the master bot of the digital assistant may interface with skill bots with specific functionalities, such as a CRM bot for performing functions related to customer relationship management (CRM), an ERP bot for performing functions related to enterprise resource planning (ERP), an HCM bot for performing functions related to human capital management (HCM), etc. This way the end user or consumer of the digital assistant need only know how to access the digital assistant through the common master bot interface and behind the scenes multiple skill bots are provided for handling the user request.

In some embodiments, in a master bot/child bots infrastructure, the master bot is configured to be aware of the available list of skill bots. The master bot may have access to metadata that identifies the various available skill bots, and for each skill bot, the capabilities of the skill bot including the tasks that can be performed by the skill bot. Upon receiving a user request in the form of an utterance, the master bot is configured to, from the multiple available skill bots, identify or predict a specific skill bot that can best serve or handle the user request. The master bot then routes the utterance (or a portion of the utterance) to that specific skill bot for further handling. Control thus flows from the master bot to the skill bots. The master bot can support multiple input and output channels. In some embodiments, routing may be performed with the aid of processing performed by one or more available skill bots. For example, as discussed below, a skill bot can be trained to infer an intent for an utterance and to determine whether the inferred intent matches an intent with which the skill bot is configured. Thus, the routing performed by the master bot can involve the skill bot communicating to the master bot an indication of whether the skill bot has been configured with an intent suitable for handling the utterance.

While the embodiment in FIG. 1 shows digital assistant 106 comprising a master bot 114 and skill bots 116-1, 116-2, and 116-3, this is not intended to be limiting. A digital assistant can include various other components (e.g., other systems and subsystems) that provide the functionalities of the digital assistant. These systems and subsystems may be implemented only in software (e.g., code, instructions stored on a computer-readable medium and executable by one or more processors), in hardware only, or in implementations that use a combination of software and hardware.

DABP 102 provides an infrastructure and various services and features that enable a user of DABP 102 to create a digital assistant including one or more skill bots associated with the digital assistant. In some instances, a skill bot can be created by cloning an existing skill bot, for example, cloning a skill bot provided by the skills store. As previously indicated, DABP 102 provides a skills store or skills catalog that offers multiple skill bots for performing various tasks. A user of DABP 102 can clone a skill bot from the skills store. As needed, modifications or customizations may be made to the cloned skill bot. In some other instances, a user of DABP 102 created a skill bot from scratch using tools and services offered by DABP 102. As previously indicated, the skills store or skills catalog provided by DABP 102 may offer multiple skill bots for performing various tasks.

In some embodiments, at a high level, creating or customizing a skill bot involves the following steps:

(1) Configuring settings for a new skill bot
(2) Configuring one or more intents for the skill bot
(3) Configuring one or more entities for one or more intents
(4) Training the skill bot
(5) Creating a dialog flow for the skill bot
(6) Adding custom components to the skill bot as needed
(7) Testing and deploying the skill bot Each of the above steps is briefly described below.

(1) Configuring settings for a new skill bot—Various settings may be configured for the skill bot. For example, a skill bot designer can specify one or more invocation names for the skill bot being created. These invocation names can then be used by users of a digital assistant to explicitly invoke the skill bot. For example, a user can input an invocation name in the user's utterance to explicitly invoke the corresponding skill bot.

(2) Configuring one or more intents and associated example utterances for the skill bot—The skill bot designer specifies one or more intents (also referred to as bot intents)

for a skill bot being created. The skill bot is then trained based upon these specified intents. These intents represent categories or classes that the skill bot is trained to infer for input utterances. Upon receiving an utterance, a trained skill bot infers an intent for the utterance, where the inferred intent is selected from the predefined set of intents used to train the skill bot. The skill bot then takes an appropriate action responsive to an utterance based upon the intent inferred for that utterance. In some instances, the intents for a skill bot represent tasks that the skill bot can perform for users of the digital assistant. Each intent is given an intent identifier or intent name. For example, for a skill bot trained for a bank, the intents specified for the skill bot may include "CheckBalance," "TransferMoney," "DepositCheck," and the like.

For each intent defined for a skill bot, the skill bot designer may also provide one or more example utterances that are representative of and illustrate the intent. These example utterances are meant to represent utterances that a user may input to the skill bot for that intent. For example, for the CheckBalance intent, example utterances may include "What's my savings account balance?", "How much is in my checking account?", "How much money do I have in my account," and the like. Accordingly, various permutations of typical user utterances may be specified as example utterances for an intent.

The intents and the associated example utterances are used as training data to train the skill bot. Various different training techniques may be used. As a result of this training, a predictive model is generated that is configured to take an utterance as input and output an intent inferred for the utterance by the predictive model. In some instances, input utterances are provided to an intent analysis engine, which is configured to use the trained model to predict or infer an intent for the input utterance. The skill bot may then take one or more actions based upon the inferred intent.

(3) Configuring entities for one or more intents of the skill bot—In some instances, additional context may be needed to enable the skill bot to properly respond to a user utterance. For example, there may be situations where a user input utterance resolves to the same intent in a skill bot. For instance, in the above example, utterances "What's my savings account balance?" and "How much is in my checking account?" both resolve to the same CheckBalance intent, but these utterances are different requests asking for different things. To clarify such requests, one or more entities are added to an intent. Using the banking skill bot example, an entity called AccountType, which defines values called "checking" and "saving" may enable the skill bot to parse the user request and respond appropriately. In the above example, while the utterances resolve to the same intent, the value associated with the AccountType entity is different for the two utterances. This enables the skill bot to perform possibly different actions for the two utterances in spite of them resolving to the same intent. One or more entities can be specified for certain intents configured for the skill bot. Entities are thus used to add context to the intent itself. Entities help describe an intent more fully and enable the skill bot to complete a user request.

In some embodiments, there are two types of entities: (a) built-in entities provided by DABP 102, and (2) custom entities that can be specified by a skill bot designer. Built-in entities are generic entities that can be used with a wide variety of bots. Examples of built-in entities include, without limitation, entities related to time, date, addresses, numbers, email addresses, duration, recurring time periods, currencies, phone numbers, URLs, and the like. Custom entities are used for more customized applications. For example, for a banking skill, an AccountType entity may be defined by the skill bot designer that enables various banking transactions by checking the user input for keywords like checking, savings, and credit cards, etc.

(4) Training the skill bot—A skill bot is configured to receive user input in the form of utterances parse or otherwise process the received input, and identify or select an intent that is relevant to the received user input. As indicated above, the skill bot has to be trained for this. In some embodiments, a skill bot is trained based upon the intents configured for the skill bot and the example utterances associated with the intents (collectively, the training data), so that the skill bot can resolve user input utterances to one of its configured intents. In some embodiments, the skill bot uses a predictive model that is trained using the training data and allows the skill bot to discern what users say (or in some cases, are trying to say). DABP 102 provides various different training techniques that can be used by a skill bot designer to train a skill bot, including various machine learning based training techniques, rules-based training techniques, and/or combinations thereof. In some embodiments, a portion (e.g., 80%) of the training data is used to train a skill bot model and another portion (e.g., the remaining 20%) is used to test or verify the model. Once trained, the trained model (also sometimes referred to as the trained skill bot) can then be used to handle and respond to user utterances. In certain cases, a user's utterance may be a question that requires only a single answer and no further conversation. In order to handle such situations, a Q&A (question-and-answer) intent may be defined for a skill bot. This enables a skill bot to output replies to user requests without having to update the dialog definition. Q&A intents are created in a similar manner as regular intents. The dialog flow for Q&A intents can be different from that for regular intents.

(5) Creating a dialog flow for the skill bot—A dialog flow specified for a skill bot describes how the skill bot reacts as different intents for the skill bot are resolved responsive to received user input. The dialog flow defines operations or actions that a skill bot will take, e.g., how the skill bot responds to user utterances, how the skill bot prompts users for input, how the skill bot returns data. A dialog flow is like a flowchart that is followed by the skill bot. The skill bot designer specifies a dialog flow using a language, such as markdown language. In some embodiments, a version of YAML called OBotML may be used to specify a dialog flow for a skill bot. The dialog flow definition for a skill bot acts as a model for the conversation itself, one that lets the skill bot designer choreograph the interactions between a skill bot and the users that the skill bot services.

In some embodiments, the dialog flow definition for a skill bot contains three sections:

(a) a context section (b) a default transitions section (c) a states section

Context section—The skill bot designer can define variables that are used in a conversation flow in the context section. Other variables that may be named in the context section include, without limitation: variables for error handling, variables for built-in or custom entities, user variables that enable the skill bot to recognize and persist user preferences, and the like.

Default transitions section—Transitions for a skill bot can be defined in the dialog flow states section or in the default transitions section. The transitions defined in the default transition section act as a fallback and get triggered when there are no applicable transitions defined within a state, or the conditions required to trigger a state transition cannot be met. The default transitions section can be used to define routing that allows the skill bot to gracefully handle unexpected user actions.

States section—A dialog flow and its related operations are defined as a sequence of transitory states, which manage the logic within the dialog flow. Each state node within a dialog flow definition names a component that provides the functionality needed at that point in the dialog. States are thus built around the components. A state contains component-specific properties and defines the transitions to other states that get triggered after the component executes.

Special case scenarios may be handled using the states sections. For example, there might be times when you want to provide users the option to temporarily leave a first skill they are engaged with to do something in a second skill within the digital assistant. For example, if a user is engaged in a conversation with a shopping skill (e.g., the user has made some selections for purchase), the user may want to jump to a banking skill (e.g., the user may want to ensure that he/she has enough money for the purchase), and then return to the shopping skill to complete the user's order. To address this, an action in the first skill can be configured to initiate an interaction with the second different skill in the same digital assistant and then return to the original flow.

(6) Adding custom components to the skill bot—As described above, states specified in a dialog flow for a skill bot name components that provide the functionality needed corresponding to the states. Components enable a skill bot to perform functions. In some embodiments, DABP 102 provides a set of preconfigured components for performing a wide range of functions. A skill bot designer can select one of more of these preconfigured components and associate them with states in the dialog flow for a skill bot. The skill bot designer can also create custom or new components using tools provided by DABP 102 and associate the custom components with one or more states in the dialog flow for a skill bot.

(7) Testing and deploying the skill bot—DABP 102 provides several features that enable the skill bot designer to test a skill bot being developed. The skill bot can then be deployed and included in a digital assistant.

While the description above describes how to create a skill bot, similar techniques may also be used to create a digital assistant (or the master bot). At the master bot or digital assistant level, built-in system intents may be configured for the digital assistant. These built-in system intents are used to identify general tasks that the digital assistant itself (i.e., the master bot) can handle without invoking a skill bot associated with the digital assistant. Examples of system intents defined for a master bot include: (1) Exit: applies when the user signals the desire to exit the current conversation or context in the digital assistant; (2) Help: applies when the user asks for help or orientation; and (3) UnresolvedIntent: applies to user input that doesn't match well with the exit and help intents. The digital assistant also stores information about the one or more skill bots associated with the digital assistant. This information enables the master bot to select a particular skill bot for handling an utterance.

At the master bot or digital assistant level, when a user inputs a phrase or utterance to the digital assistant, the digital assistant is configured to perform processing to determine how to route the utterance and the related conversation. The digital assistant determines this using a routing model, which can be rules-based, AI-based, or a combination thereof. The digital assistant uses the routing model to determine whether the conversation corresponding to the user input utterance is to be routed to a particular skill for handling, is to be handled by the digital assistant or master bot itself per a built-in system intent, or is to be handled as a different state in a current conversation flow.

In some embodiments, as part of this processing, the digital assistant determines if the user input utterance explicitly identifies a skill bot using its invocation name. If an invocation name is present in the user input, then it is treated as explicit invocation of the skill bot corresponding to the invocation name. In such a scenario, the digital assistant may route the user input to the explicitly invoked skill bot for further handling. If there is no specific or explicit invocation, in some embodiments, the digital assistant evaluates the received user input utterance and computes confidence scores for the system intents and the skill bots associated with the digital assistant. The score computed for a skill bot or system intent represents how likely the user input is representative of a task that the skill bot is configured to perform or is representative of a system intent. Any system intent or skill bot with an associated computed confidence score exceeding a threshold value (e.g., a Confidence Threshold routing parameter) is selected as a candidate for further evaluation. The digital assistant then selects, from the identified candidates, a particular system intent or a skill bot for further handling of the user input utterance. In some embodiments, after one or more skill bots are identified as candidates, the intents associated with those candidate skills are evaluated (according to the intent model for each skill) and confidence scores are determined for each intent. In general, any intent that has a confidence score exceeding a threshold value (e.g., 70%) is treated as a candidate intent. If a particular skill bot is selected, then the user utterance is routed to that skill bot for further processing. If a system intent is selected, then one or more actions are performed by the master bot itself according to the selected system intent.

Figure 2:
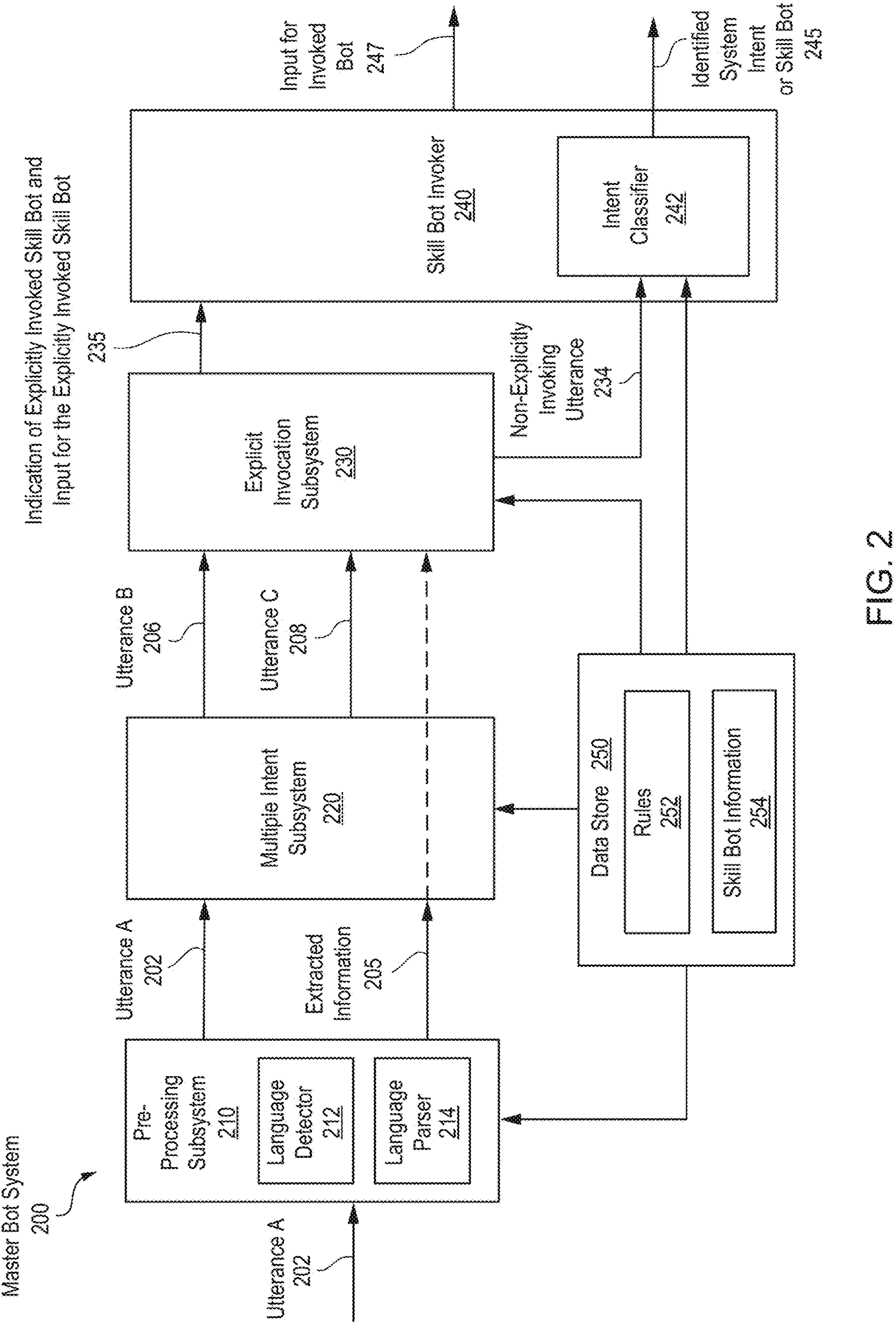
FIG. 2 is a simplified block diagram of a computing system implementing a master bot in accordance with various embodiments.

FIG. 2 is a simplified block diagram of a master bot (MB) system 200 according to some embodiments. MB system 200 can be implemented in software only, hardware only, or a combination of hardware and software. MB system 200 includes a pre-processing subsystem 210, a multiple intent subsystem (MIS) 220, an explicit invocation subsystem (EIS) 230, a skill bot invoker 240, and a data store 250. MB system 200 depicted in FIG. 2 is merely an example of an arrangement of components in a master bot. One of ordinary skill in the art would recognize many possible variations, alternatives, and modifications. For example, in some implementations, MB system 200 may have more or fewer systems or components than those shown in FIG. 2, may combine two or more subsystems, or may have a different configuration or arrangement of subsystems.

Pre-processing subsystem 210 receives an utterance "A" 202 from a user and processes the utterance through a language detector 212 and a language parser 214. As indicated above, an utterance can be provided in various ways including audio or text. The utterance 202 can be a sentence fragment, a complete sentence, multiple sentences, and the like. Utterance 202 can include punctuation. For example, if the utterance 202 is provided as audio, the pre-processing subsystem 210 may convert the audio to text using a speech-to-text converter (not shown) that inserts punctuation marks into the resulting text, e.g., commas, semicolons, periods, etc.

Language detector 212 detects the language of the utterance 202 based on the text of the utterance 202. The manner in which the utterance 202 is handled depends on the language since each language has its own grammar and semantics. Differences between languages are taken into consideration when analyzing the syntax and structure of an utterance.

Language parser 214 parses the utterance 202 to extract part of speech (POS) tags for individual linguistic units (e.g., words) in the utterance 202. POS tags include, for example, noun (NN), pronoun (PN), verb (VB), and the like. Language parser 214 may also tokenize the linguistic units of the utterance 202 (e.g., to convert each word into a separate token) and lemmatize words. A lemma is the main form of a set of words as represented in a dictionary (e.g., "run" is the lemma for run, runs, ran, running, etc.). Other types of pre-processing that the language parser 214 can perform include chunking of compound expressions, e.g., combining "credit" and "card" into a single expression "credit_card." Language parser 214 may also identify relationships between the words in the utterance 202. For example, in some embodiments, the language parser 214 generates a dependency tree that indicates which part of the utterance (e.g. a particular noun) is a direct object, which part of the utterance is a preposition, and so on. The results of the processing performed by the language parser 214 form extracted information 205 and are provided as input to MIS 220 together with the utterance 202 itself.

As indicated above, the utterance 202 can include more than one sentence. For purposes of detecting multiple intents and explicit invocation, the utterance 202 can be treated as a single unit even if it includes multiple sentences. However, in some embodiments, pre-processing can be performed, e.g., by the pre-processing subsystem 210, to identify a single sentence among multiple sentences for multiple intents analysis and explicit invocation analysis. In general, the results produced by MIS 220 and EIS 230 are substantially the same regardless of whether the utterance 202 is processed at the level of an individual sentence or as a single unit comprising multiple sentences.

Figure 3:
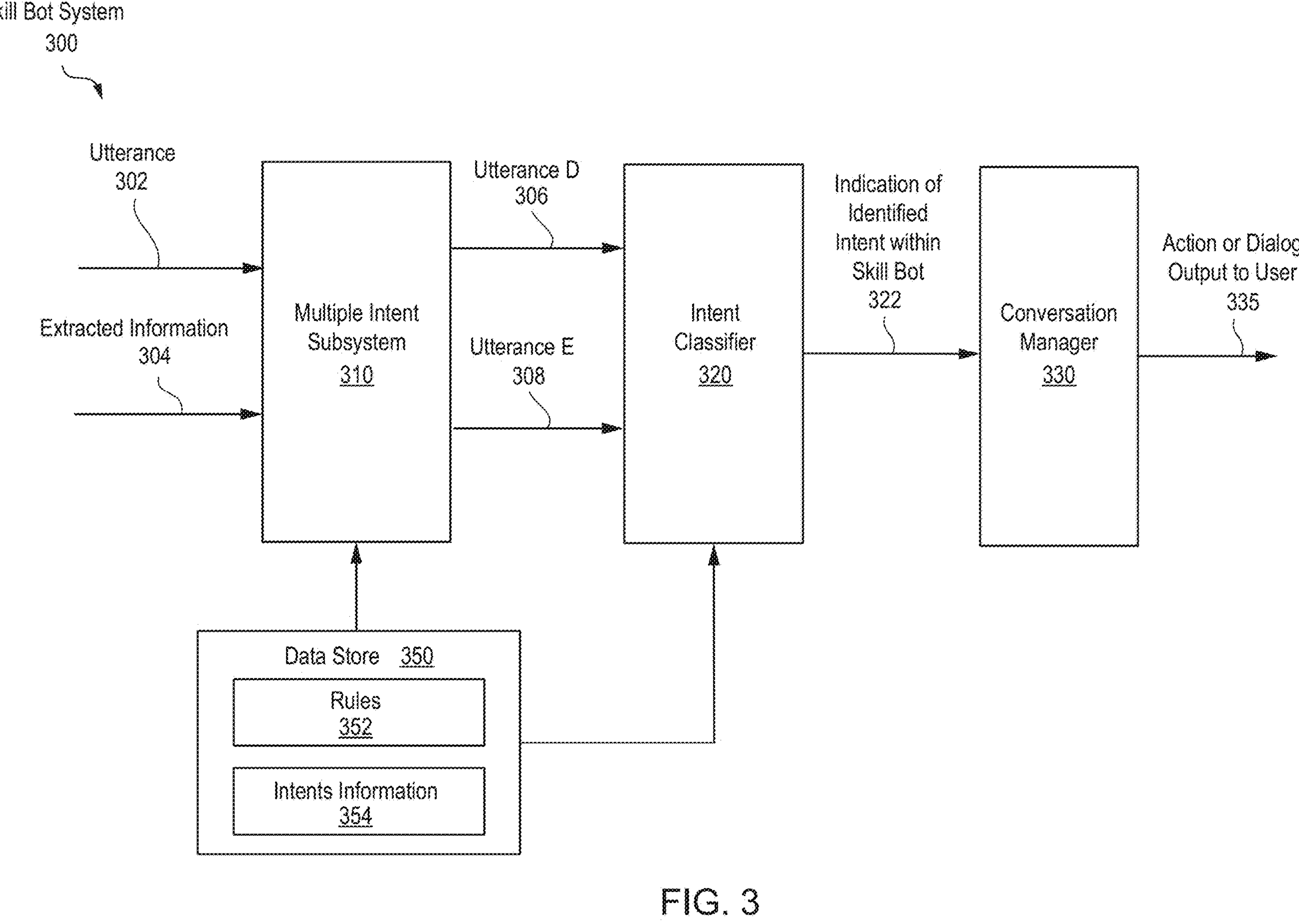
FIG. 3 is a simplified block diagram of a computing system implementing a skill bot in accordance with various embodiments.

MIS 220 determines whether the utterance 202 represents multiple intents. Although MIS 220 can detect the presence of multiple intents in the utterance 202, the processing performed by MIS 220 does not involve determining whether the intents of the utterance 202 match to any intents that have been configured for a bot. Instead, processing to determine whether an intent of the utterance 202 matches a bot intent can be performed by an intent classifier 242 of the MB system 200 or by an intent classifier of a skill bot (e.g., as shown in the embodiment of FIG. 3). The processing performed by MIS 220 assumes that there exists a bot (e.g., a particular skill bot or the master bot itself) that can handle the utterance 202. Therefore, the processing performed by MIS 220 does not require knowledge of what bots are in the chatbot system (e.g., the identities of skill bots registered with the master bot) or knowledge of what intents have been configured for a particular bot.

To determine that the utterance 202 includes multiple intents, the MIS 220 applies one or more rules from a set of rules 252 in the data store 250. The rules applied to the utterance 202 depend on the language of the utterance 202 and may include sentence patterns that indicate the presence of multiple intents. For example, a sentence pattern may include a coordinating conjunction that joins two parts (e.g., conjuncts) of a sentence, where both parts correspond to a separate intent. If the utterance 202 matches the sentence pattern, it can be inferred that the utterance 202 represents multiple intents. It should be noted that an utterance with multiple intents does not necessarily have different intents (e.g., intents directed to different bots or to different intents within the same bot). Instead, the utterance could have separate instances of the same intent, e.g. "Place a pizza order using payment account X, then place a pizza order using payment account Y."

As part of determining that the utterance 202 represents multiple intents, the MIS 220 also determines what portions of the utterance 202 are associated with each intent. MIS 220 constructs, for each intent represented in an utterance containing multiple intents, a new utterance for separate processing in place of the original utterance, e.g., an utterance "B" 206 and an utterance "C" 208, with respect to FIG. 2. Thus, the original utterance 202 can be split into two or more separate utterances that are handled one at a time. MIS 220 determines, using the extracted information 205 and/or from analysis of the utterance 202 itself, which of the two or more utterances should be handled first. For example, MIS 220 may determine that the utterance 202 contains a marker word indicating that a particular intent should be handled first. The newly formed utterance corresponding to this particular intent (e.g., one of utterance 206 or utterance 208) will be the first to be sent for further processing by EIS 230. After a conversation triggered by the first utterance has ended (or has been temporarily suspended), the next highest priority utterance (e.g., the other one of utterance 206 or utterance 208) can then be sent to the EIS 230 for processing.

EIS 230 determines whether the utterance that it receives (e.g., utterance 206 or utterance 208) contains an invocation name of a skill bot. In some embodiments, each skill bot in a chatbot system is assigned a unique invocation name that distinguishes the skill bot from other skill bots in the chatbot system. A list of invocation names can be maintained as part of skill bot information 254 in data store 250. An utterance is deemed to be an explicit invocation when the utterance contains a word match to an invocation name. If a bot is not explicitly invoked, then the utterance received by the EIS 230 is deemed a non-explicitly invoking utterance 234 and is input to an intent classifier (e.g., intent classifier 242) of the master bot to determine which bot to use for handling the utterance. In some instances, the intent classifier 242 will determine that the master bot should handle a non-explicitly invoking utterance. In other instances, the intent classifier 242 will determine a skill bot to route the utterance to for handling.

The explicit invocation functionality provided by the EIS 230 has several advantages. It can reduce the amount of processing that the master bot has to perform. For example, when there is an explicit invocation, the master bot may not have to do any intent classification analysis (e.g., using the intent classifier 242), or may have to do reduced intent classification analysis for selecting a skill bot. Thus, explicit invocation analysis may enable selection of a particular skill bot without resorting to intent classification analysis.

Also, there may be situations where there is an overlap in functionalities between multiple skill bots. This may happen, for example, if the intents handled by the two skill bots overlap or are very close to each other. In such a situation, it may be difficult for the master bot to identify which of the multiple skill bots to select based upon intent classification analysis alone. In such scenarios, the explicit invocation disambiguates the particular skill bot to be used.

In addition to determining that an utterance is an explicit invocation, the EIS 230 is responsible for determining whether any portion of the utterance should be used as input to the skill bot being explicitly invoked. In particular, EIS 230 can determine whether part of the utterance is not associated with the invocation. The EIS 230 can perform this determination through analysis of the utterance and/or analysis of the extracted information 205. EIS 230 can send the part of the utterance not associated with the invocation to the invoked skill bot in lieu of sending the entire utterance that was received by the EIS 230. In some instances, the input to the invoked skill bot is formed simply by removing any portion of the utterance associated with the invocation. For example, "I want to order pizza using Pizza Bot" can be shortened to "I want to order pizza" since "using Pizza Bot" is relevant to the invocation of the pizza bot, but irrelevant to any processing to be performed by the pizza bot. In some instances, EIS 230 may reformat the part to be sent to the invoked bot, e.g., to form a complete sentence. Thus, the EIS 230 determines not only that there is an explicit invocation, but also what to send to the skill bot when there is an explicit invocation. In some instances, there may not be any text to input to the bot being invoked. For example, if the utterance was "Pizza Bot", then the EIS 230 could determine that the pizza bot is being invoked, but there is no text to be processed by the pizza bot. In such scenarios, the EIS 230 may indicate to the skill bot invoker 240 that there is nothing to send.

Skill bot invoker 240 invokes a skill bot in various ways. For instance, skill bot invoker 240 can invoke a bot in response to receiving an indication 235 that a particular skill bot has been selected as a result of an explicit invocation. The indication 235 can be sent by the EIS 230 together with the input for the explicitly invoked skill bot. In this scenario, the skill bot invoker 240 will turn control of the conversation over to the explicitly invoked skill bot. The explicitly invoked skill bot will determine an appropriate response to the input from the EIS 230 by treating the input as a stand-alone utterance. For example, the response could be to perform a specific action or to start a new conversation in a particular state, where the initial state of the new conversation depends on the input sent from the EIS 230.

Another way in which skill bot invoker 240 can invoke a skill bot is through implicit invocation using the intent classifier 242. The intent classifier 242 can be trained, using machine learning and/or rules-based training techniques, to determine a likelihood that an utterance is representative of a task that a particular skill bot is configured to perform. The intent classifier 242 is trained on different classes, one class for each skill bot. For instance, whenever a new skill bot is registered with the master bot, a list of example utterances associated with the new skill bot can be used to train the intent classifier 242 to determine a likelihood that a particular utterance is representative of a task that the new skill bot can perform. The parameters produced as result of this training (e.g., a set of values for parameters of a machine learning model) can be stored as part of skill bot information 254.

In some embodiments, the intent classifier 242 is implemented using a machine learning model, as described in further detail herein. Training of the machine learning model may involve inputting at least a subset of utterances from the example utterances associated with various skill bots to generate, as an output of the machine learning model, inferences as to which bot is the correct bot for handling any particular training utterance. For each training utterance, an indication of the correct bot to use for the training utterance may be provided as ground truth information. The behavior of the machine learning model can then be adapted (e.g., through back-propagation) to minimize the difference between the generated inferences and the ground truth information.

In some embodiments, the intent classifier 242 determines, for each skill bot registered with the master bot, a confidence score indicating a likelihood that the skill bot can handle an utterance (e.g., the non-explicitly invoking utterance 234 received from EIS 230). The intent classifier 242 may also determine a confidence score for each system level intent (e.g., help, exit) that has been configured. If a particular confidence score meets one or more conditions, then the skill bot invoker 240 will invoke the bot associated with the particular confidence score. For example, a threshold confidence score value may need to be met. Thus, an output 245 of the intent classifier 242 is either an identification of a system intent or an identification of a particular skill bot. In some embodiments, in addition to meeting a threshold confidence score value, the confidence score must exceed the next highest confidence score by a certain win margin. Imposing such a condition would enable routing to a particular skill bot when the confidence scores of multiple skill bots each exceed the threshold confidence score value.

After identifying a bot based on evaluation of confidence scores, the skill bot invoker 240 hands over processing to the identified bot. In the case of a system intent, the identified bot is the master bot. Otherwise, the identified bot is a skill bot. Further, the skill bot invoker 240 will determine what to provide as input 247 for the identified bot. As indicated above, in the case of an explicit invocation, the input 247 can be based on a part of an utterance that is not associated with the invocation, or the input 247 can be nothing (e.g., an empty string). In the case of an implicit invocation, the input 247 can be the entire utterance.

Data store 250 comprises one or more computing devices that store data used by the various subsystems of the master bot system 200. As explained above, the data store 250 includes rules 252 and skill bot information 254. The rules 252 include, for example, rules for determining, by MIS 220, when an utterance represents multiple intents and how to split an utterance that represents multiple intents. The rules 252 further include rules for determining, by EIS 230, which parts of an utterance that explicitly invokes a skill bot to send to the skill bot. The skill bot information 254 includes invocation names of skill bots in the chatbot system, e.g., a list of the invocation names of all skill bots registered with a particular master bot. The skill bot information 254 can also include information used by intent classifier 242 to determine a confidence score for each skill bot in the chatbot system, e.g., parameters of a machine learning model.

FIG. 3 is a simplified block diagram of a skill bot system 300 according to some embodiments. Skill bot system 300 is a computing system that can be implemented in software only, hardware only, or a combination of hardware and software. In some embodiments such as the embodiment depicted in FIG. 1, skill bot system 300 can be used to implement one or more skill bots within a digital assistant.

Skill bot system 300 includes an MIS 310, an intent classifier 320, and a conversation manager 330. The MIS 310 is analogous to the MIS 220 in FIG. 2 and provides similar functionality, including being operable to determine, using rules 352 in a data store 350: (1) whether an utterance represents multiple intents and, if so, (2) how to split the utterance into a separate utterance for each intent of the multiple intents. In some embodiments, the rules applied by MIS 310 for detecting multiple intents and for splitting an utterance are the same as those applied by MIS 220. The MIS 310 receives an utterance 302 and extracted information 304. The extracted information 304 is analogous to the extracted information 205 in FIG. 1 and can be generated using the language parser 214 or a language parser local to the skill bot system 300.

Intent classifier 320 can be trained in a similar manner to the intent classifier 242 discussed above in connection with the embodiment of FIG. 2 and as described in further detail herein. For instance, in some embodiments, the intent classifier 320 is implemented using a machine learning model. The machine learning model of the intent classifier 320 is trained for a particular skill bot, using at least a subset of example utterances associated with that particular skill bot as training utterances. The ground truth for each training utterance would be the particular bot intent associated with the training utterance.

The utterance 302 can be received directly from the user or supplied through a master bot. When the utterance 302 is supplied through a master bot, e.g., as a result of processing through MIS 220 and EIS 230 in the embodiment depicted in FIG. 2, the MIS 310 can be bypassed so as to avoid repeating processing already performed by MIS 220. However, if the utterance 302 is received directly from the user, e.g., during a conversation that occurs after routing to a skill bot, then MIS 310 can process the utterance 302 to determine whether the utterance 302 represents multiple intents. If so, then MIS 310 applies one or more rules to split the utterance 302 into a separate utterance for each intent, e.g., an utterance "D" 306 and an utterance "E" 308. If utterance 302 does not represent multiple intents, then MIS 310 forwards the utterance 302 to intent classifier 320 for intent classification and without splitting the utterance 302.

Intent classifier 320 is configured to match a received utterance (e.g., utterance 306 or 308) to an intent associated with skill bot system 300. As explained above, a skill bot can be configured with one or more intents, each intent including at least one example utterance that is associated with the intent and used for training a classifier. In the embodiment of FIG. 2, the intent classifier 242 of the master bot system 200 is trained to determine confidence scores for individual skill bots and confidence scores for system intents. Similarly, intent classifier 320 can be trained to determine a confidence score for each intent associated with the skill bot system 300. Whereas the classification performed by intent classifier 242 is at the bot level, the classification performed by intent classifier 320 is at the intent level and therefore finer grained. The intent classifier 320 has access to intents information 354. The intents information 354 includes, for each intent associated with the skill bot system 300, a list of utterances that are representative of and illustrate the meaning of the intent and are typically associated with a task performable by that intent. The intents information 354 can further include parameters produced as a result of training on this list of utterances.

Conversation manager 330 receives, as an output of intent classifier 320, an indication 322 of a particular intent, identified by the intent classifier 320, as best matching the utterance that was input to the intent classifier 320. In some instances, the intent classifier 320 is unable to determine any match. For example, the confidence scores computed by the intent classifier 320 could fall below a threshold confidence score value if the utterance is directed to a system intent or an intent of a different skill bot. When this occurs, the skill bot system 300 may refer the utterance to the master bot for handling, e.g., to route to a different skill bot. However, if the intent classifier 320 is successful in identifying an intent within the skill bot, then the conversation manager 330 will initiate a conversation with the user.

The conversation initiated by the conversation manager 330 is a conversation specific to the intent identified by the intent classifier 320. For instance, the conversation manager 330 may be implemented using a state machine configured to execute a dialog flow for the identified intent. The state machine can include a default starting state (e.g., for when the intent is invoked without any additional input) and one or more additional states, where each state has associated with it actions to be performed by the skill bot (e.g., executing a purchase transaction) and/or dialog (e.g., questions, responses) to be presented to the user. Thus, the conversation manager 330 can determine an action/dialog 335 upon receiving the indication 322 identifying the intent, and can determine additional actions or dialog in response to subsequent utterances received during the conversation.

Data store 350 comprises one or more computing devices that store data used by the various subsystems of the skill bot system 300. With respect to FIG. 3, the data store 350 includes the rules 352 and the intents information 354. In some embodiments, data store 350 can be integrated into a data store of a master bot or digital assistant, e.g., the data store 250 in FIG. 2.

Digital Assistant Using Large Language Model Block Handling (Skill Track with LLM Support)

Figure 4:
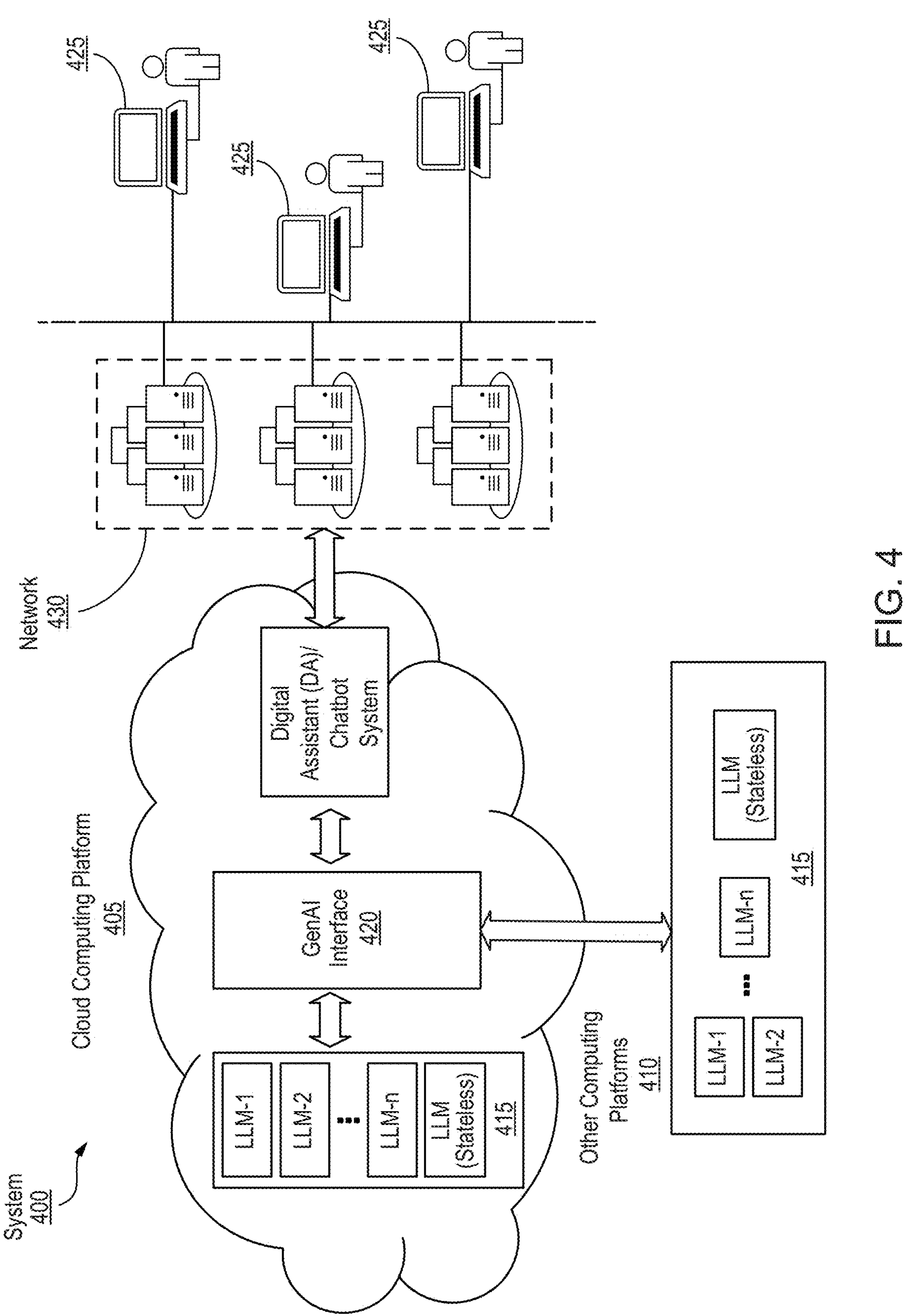
FIG. 4 is an example simplified system architecture for enabling interaction of multiple users with a set of large language models (LLMs) in accordance with various embodiments.

FIG. 4 illustrates an example system 400 for enabling the integration of large language models (LLMs) with digital assistants (e.g., DAs described with respect to FIGS. 1-3) to enhance skills with generative AI capabilities. These capabilities include handling small talk with a user, generating written summaries of data, automating challenging or repetitive business tasks, such as those required for talent acquisition, and providing sentiment analysis of a given piece of text to determine whether it reflects a positive, negative, or neutral opinion. Using the Invoke Large Language Model component, a skill bot developer can plug these capabilities into their dialog flow wherever they're needed. This dialog flow component is the primary integration piece for generative AI in that it contacts the LLM that are hosted on one or more computing platforms such as cloud platforms, on-premises platforms, edge platforms, etc. through a call (e.g., a REST call), then sends the LLM a prompt (the natural language instructions to the LLM) along with related parameters. It then returns the results generated by the model (which are also known as completions) and manages the state of the LLM-user interactions so that its responses remain in context after successive rounds of user queries and feedback. The LLM component can call any LLM. A user can add one or more LLM component states (or LLM blocks) to flows. A user can also chain the LLM calls so that the output of one LLM request can be passed to a subsequent LLM request.

The system 400 includes a cloud computing platform 405 (e.g., an IaaS platform such as Oracle Cloud Infrastructure as described in detail with respect to FIGS. 13-17) and other computing platforms 410 configured to provide services including the capability to interact with digital assistants enhanced with the LLM component for invoking LLMs 415 hosted by one or more LLM service providers. In some embodiments, the cloud computing platform 405 hosts the LLMs 415 for the one or more LLM service providers. In other embodiments, the one or more other computing platform(s) 410 such as one or more other cloud platforms, one or more on-premises platforms, one or more edge platforms, etc. hosts the LLMs 415 for the one or more LLM service providers. In other embodiments, the cloud computing platform 405 hosts some of the LLMs 415 for some of the one or more LLM service providers and the one or more other computing platform(s) 410 hosts some of the LLMs 415 for some of the one or more LLM service providers. The LLMs 415 include a collection of multiple LLMs (e.g., GPT-4, LaMDA, etc.) that can be used for processing various generative artificial intelligence tasks (e.g., natural language understanding and processing) to provide efficient, user centric and context aware responses to one or more users.

Besides the LLM component, the other major pieces of the LLM integration include endpoints for the one or more LLM service provider and transformation handlers for converting the request and response payloads to and from the digital assistant's format using the Common LLM Interface (CLMI) (also described herein as the GenAI Interface 420). Follows are the high-level steps for adding these and other components to create the LLM integration for a skill:

- Register an API service in the digital assistant instance for the LLM's endpoint (e.g., REST endpoint).
- For the skill, create a LLM Transformation Event Handler to convert the LLM request and response payloads to and from CLMI using the GenAI Interface 420.
  - In some instances, prebuilt handlers are provided for example if a user is integrating their skill with the Cohere model or with Oracle Generative AI Service. If they are accessing other models, such as Azure OpenAI, the user can update the starter transformation code that is provided using a declarative process.
- Define an LLM service for the skill that maps to the service that the user has registered to the instance with an LLM Transformation Handler.
- In the flow of the skill where the user wants to use the LLM, insert and configure an LLM component by adding the prompt text and setting other parameters.
  - The prompt text and/or template can be added using a Prompt Builder (accessed through the LLM component) to perfect and test the prompt.

Once the LLM integration is configured, the CLMI or GenAI interface 420 enables the LLM component to handle these request and response payloads (e.g., translate, moderate, and validate responses and requests). In general, the GenAI interface 420 is comprised of various components for handling the following:

- A request body specification
- A success response body specification, applicable when LLM call returns a standard response such as a HTTP 200 status
- An error response body specification, applicable when the LLM call returns a status other than a standard response, and the LLM invocation itself was successful. For example, in case of HTTP status code 401 (not authorized) or 500 (internal server error) the LLM is not successfully invoked hence no response body is expected. The VFD LLM component will handle these status codes separately.
- A moderation request body
- A moderation response body The system 400 further includes one or more client devices 425 (e.g., personal computing device, mobile device, kiosk, IoT device, etc.) that can be used by one or more users to interact with the services provided by the cloud computing platform 405 and other computing platforms 410 (optionally via the one or more networks 430, which may host applications or websites that are used to interact with the services). Users using the client devices 425 may send utterances (e.g., queries) or commands to the digital assistant/chatbot system for processing including LLM integration via the LLM component and the CLMI or GenAI interface 420.

Digital Assistant and Knowledge Dialog (Agent Track)

Figure 5:
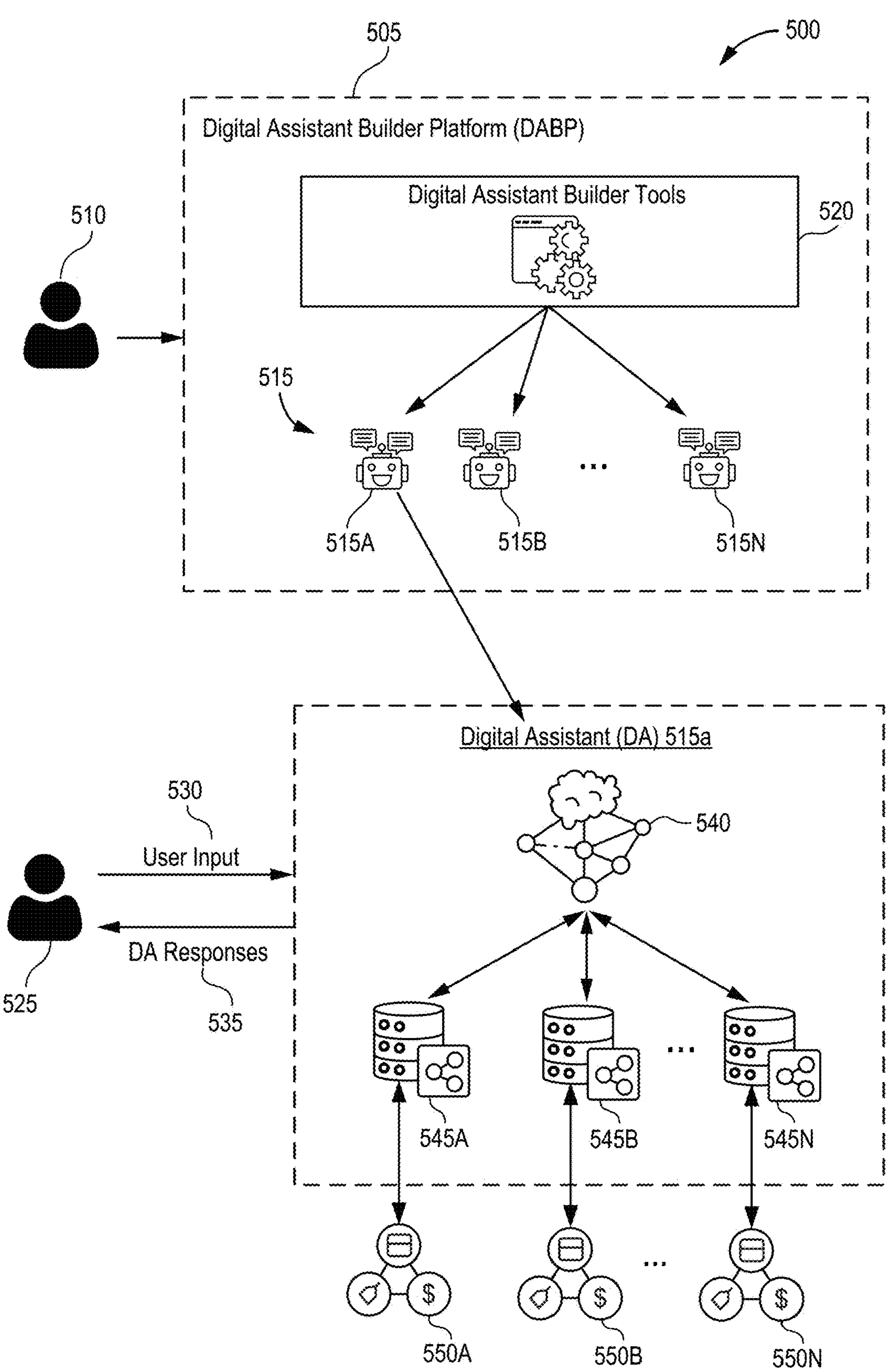
FIG. 5 is a simplified block diagram of a distributed environment incorporating a chatbot system in accordance with various embodiments.

FIG. 5 is a simplified block diagram of an environment 500 incorporating a generative AI based digital assistant system (also described herein as simply a digital assistant or in more specific terms with reference to implementation of agents as an agent assistant) according to certain embodiments. Environment 500 includes a digital assistant builder platform (DABP) 505 that enables users 510 to create and deploy digital assistant systems 515. For purposes of this disclosure, a digital assistant is an entity that helps users of the digital assistant accomplish various tasks through natural language conversations. The DABP and digital assistant can be implemented using software only (e.g., the digital assistant is a digital entity implemented using programs, code, or instructions executable by one or more processors), using hardware, or using a combination of hardware and software. In some instances, the environment 500 is part of an Infrastructure as a Service (IaaS) cloud service (as described below in detail) and the DABP and digital assistant can be implemented as part of the IaaS by leveraging the scalable computing resources and storage capabilities provided by the IaaS provider to process and manage large volumes of data and complex computations. This setup allows the DABP and digital assistant to deliver real-time, responsive interactions while ensuring high availability, security, and performance scalability to meet varying demand levels. A digital assistant can be embodied or implemented in various physical systems or devices, such as in a computer, a mobile phone, a watch, an appliance, a vehicle, and the like. A digital assistant is also sometimes referred to as a chatbot system. Accordingly, for purposes of this disclosure, the terms digital assistant and chatbot system are interchangeable.

DABP 505 can be used to create one or more digital assistant systems (or DAs). For example, as illustrated in FIG. 5, user 510 representing a particular enterprise can use DABP 505 to create and deploy a digital assistant 515A for users of the particular enterprise. For example, DABP 505 can be used by a bank to create one or more digital assistants for use by the bank's customers, for example to change a 401k contribution, etc. The same DABP 505 platform can be used by multiple enterprises to create digital assistants. As another example, an owner of a restaurant, such as a pizza shop, may use DABP 505 to create and deploy digital assistant 515B that enables customers of the restaurant to order food (e.g., order pizza).

To create one or more digital assistant systems 515, the DABP 505 is equipped with a suite of tools 520, enabling the acquisition of LLMs, agent creation, asset identification, and deployment of digital assistant systems within a service architecture for users via a computing platform such as a cloud computing platform described in detail with respect to FIGS. 13-17. In some instances, the tools 520 can be utilized to access pre-trained and/or fine-tuned LLMs from data repositories or computing systems. The pre-trained LLMs serve as foundational elements, possessing extensive language understanding derived from vast datasets. This capability enables the models to generate coherent responses across various topics, facilitating transfer learning. Pre-trained models offer cost-effectiveness and flexibility, which allows for scalable improvements and continuous pre-training with new data, often establishing benchmarks in Natural Language Processing (NLP) tasks. Conversely, fine-tuned models are specifically trained for tasks or industries (e.g., plan creation utilizing the LLM's in-context learning capability, knowledge or information retrieval on behalf of an agent, response generation for human-like conversation, etc.), enhancing their performance on specific applications and enabling efficient learning from smaller, specialized datasets. Fine-tuning provides advantages such as task specialization, data efficiency, quicker training times, model customization, and resource efficiency. In some embodiments, fine-tuning may be particularly advantageous for niche applications and ongoing enhancement.

In other instances, the tools 520 can be utilized to pre-train and/or fine-tune the LLMs. The tools 520, or any subset thereof, may be standalone or part of a machine-learning operationalization framework, inclusive of hardware components like processors (e.g., CPU, GPU, TPU, FPGA, or any combination), memory, and storage. This framework operates software or computer program instructions (e.g., TensorFlow, PyTorch, Keras, etc.) to execute arithmetic, logic, input/output commands for training, validating, and deploying machine-learning models in a production environment. In certain instances, the tools 520 implement the training, validating, and deploying of the models using a cloud platform such as Oracle Cloud Infrastructure (OCI). Leveraging a cloud platform can make machine-learning more accessible, flexible, and cost-effective, which can facilitate faster model development and deployment for developers.

The tools 520 further include a prompt-based agent composition unit for creating agents and their associated actions that an end-user can end up invoking. An agent is a container of agent actions and can be part of one or more digital assistants. Each digital assistant may contain one or more agents through a digital assistant relation, which is the intersection entity that links an agent to a digital assistant. The agent and digital assistant are implemented as bot subtypes and may be persisted into an existing BOTS table. This has advantages in terms of reuse of design-time code (e.g., Java code) and UI artefacts.

An agent action is of a specific action type (e.g., knowledge, service or API, LLM, etc.) and contains a description and schema (e.g., JSON schema) which defines the action parameters. The action description and parameters schema are indexed by semantic index and sent to the planner LLM to select the appropriate action(s) to execute. The action parameters are key-value pairs that are input for the action execution. They are derived from the properties in the schema but may also include additional UI/dialog properties that are used for slot filling dialogs. The actions can be part of one or more classes. For example, some actions may be part of an application event subscription class, which defines an agent action that should be executed when an application event is received. The application event can be received in the form of un update application context command message. An application event property mapping class (part of the application event subscription class) specifically maps the application event payload properties to corresponding agent action parameters. An action can optionally be part of an action group. An action group may be used when importing a plugin manifest, or when importing an external API spec such as an Open API spec. An action group is particularly useful when re-importing a plugin or open API spec, so new actions can be added, existing actions can be updated, or actions that are no longer present in the new manifest or Open API spec can be removed. At runtime, an action group may only be used to limit the application context groups that are sent to the LLM as conversation context by looking up the action group name which corresponds to a context group context.

The agents (e.g., 401k Change Contribution Agent) may be primarily defined as a compilation of agent artifacts using natural language within the prompt-based agent composition unit. Users 510 can create functional agents quickly by providing agent artifact information, parameters, and configurations and by pointing to assets. The assets can be or include resources, such as APIs for interfacing with applications, files and/or documents for retrieving knowledge, data stores for interacting with data, and the like, available to the agents for the execution of actions. The assets are imported, and then the users 510 can use natural language again to provide additional API customizations for dialog and routing/reasoning. Most of what an agent does may involve executing actions. An action can be an explicit action that's authored using natural language (similar to creating agent artifacts—e.g., 'What is the impact of XYZ on my 401k Contribution limit?' action in the below '401k Contribution Agent' figure) or an implicit action that is created when an asset is imported (automatically imported upon pointing to a given asset based on metadata and/or specifications associated with the asset—e.g., actions created for Change Contribution and Get Contribution API in the below '401k Contribution Agent' figure). The design time user can easily create explicit actions. For example, the user can choose the 'Rich Text' action type (see Table 1 for a list of exemplary action types) and creates the name artifact 'What is the impact of XYZ on my 401k Contribution limit?' when the user learns that a new FAQ needs to be added, as it's not currently in the knowledge documents (assets) the agent references (thus was not implicitly added as an action).

TABLE 1

| | Action Type | Description |
|---|---|---|
| 1 | Prompt | The action is implemented using a prompt to an LLM. |
| 2 | Rich Text | The action is implemented using rich text. The most common use case is FAQs. |
| 3 | Flow | The action is implemented using Visual Flow Designer flow. May be used for complex cases where the developer is not able to use the out-of-the-box dialogue and dialog customizations. |

There are various ways in which the agents and assets can be associated or added to a digital assistant 515. In some instances, the agents can be developed by an enterprise and then added to a digital assistant using DABP 505. In other instances, the agents can be developed and created using DABP 505 and then added to a digital assistant created using DABP 505. In yet other instances, DABP 505 provides an online digital store (referred to as an "agent store") that offers various pre-created agents directed to a wide range of tasks and actions. The agents offered through the agent store may also expose various cloud services. In order to add the agents to a digital assistant being generated using DABP 505, a user 510 of DABP 505 can access assets via tools 520, select specific assets for an agent, initiate a few mock chat conversations with the agent, and indicate that the agent is to be added to the digital assistant created using DABP 505.

Once deployed in a production environment, such as the architecture described with respect to FIG. 2, a digital assistant, such as digital assistant 515A built using DABP 505, can be used to perform various tasks via natural language-based conversations between the digital assistant 515A and its users 525. As described above, the digital assistant 515A illustrated in FIG. 5, can be made available or accessible to its users 525 through a variety of different channels, such as but not limited to, via certain applications, via social media platforms, via various messaging services and applications, and other applications or channels. A single digital assistant can have several channels configured for it so that it can be run on and be accessed by different services simultaneously.

As part of a conversation, a user 525 may provide one or more user inputs 530 to digital assistant 515A and get responses 535 back from digital assistant 515A via a user interface element such as a chat window. A conversation can include one or more of user inputs 530 and responses 535. Via these conversations, a user 525 can request one or more tasks to be performed by the digital assistant 515A and, in response, the digital assistant 515A is configured to perform the user-requested tasks and respond with appropriate responses to the user 525 using one or more LLMs 540. Conversations shown in the chat window can be organized by thread. For example, in some applications, a conversation related to one page of an application should not be mixed with a conversation related to another page of the application. The application and/or the plugins for the application define the thread boundaries (e.g., a set of (nested) plugins can run within their own thread). Effectively, the chat window will only show the history of messages that belong to the same thread. Setting and changing the thread can be performed via the application and/or the plugins using an update application context command message. Additionally or alternatively, the thread can be changed via an execution plan orchestrator when a user query is matched to a plugin semantic action and the plugin runs in a thread different than the current thread. In this case, the planner changes threads, so that any messages sent in response to the action being executed are shown in the correct new thread. Per agent dialog thread, the following information can be maintained by the digital assistant: the application context, the LLM conversation history, the conversation history with the user, and the agent execution context which holds information about the (stacked) execution plan(s) related to this thread.

User inputs 530 are generally in a natural language form and are referred to as utterances, which may also be referred to as prompts, queries, requests, and the like. The user inputs 530 can be in text form, such as when a user types in a sentence, a question, a text fragment, or even a single word and provides it as input to digital assistant 515A. In some embodiments, a user input 530 can be in audio input or speech form, such as when a user says or speaks something that is provided as input to digital assistant 515A. The user inputs 530 are typically in a language spoken by the user 525. For example, the user inputs 530 may be in English, or some other language. When a user input 530 is in speech form, the speech input is converted to text form user input 530 in that particular language and the text utterances are then processed by digital assistant 515A. Various speech-to-text processing techniques may be used to convert a speech or audio input to a text utterance, which is then processed by digital assistant 515A. In some embodiments, the speech-to-text conversion may be done by digital assistant 515A itself. For purposes of this disclosure, it is assumed that the user inputs 530 are text utterances that have been provided directly by a user 525 of digital assistant 515A or are the results of conversion of input speech utterances to text form. This however is not intended to be limiting or restrictive in any manner.

The user inputs 530 can be used by the digital assistant 515A to determine a list of candidate agents 545A-N. The list of candidate agents (e.g., 545A-N) includes agents configured to perform one or more actions that could potentially facilitate a response 535 to the user input 530. The list may be determined by running a search, such as a semantic search, on a context and memory store that has one or more indices comprising metadata for all agents 545 available to the digital assistant 515A. Metadata for the candidate agents 545A-N in the list of candidate agents is then combined with the user input to construct an input prompt for the one or more LLMs 540.

Digital assistant 515A is configured to use one or more LLMs 540 to apply NLP techniques to text and/or speech to understand the input prompt and apply natural language understanding (NLU) including syntactic and semantic analysis of the text and/or speech to determine the meaning of the user inputs 530. Determining the meaning of the utterance may involve identifying the goal of the user, one or more intents of the user, the context surrounding various words or phrases or sentences, one or more entities corresponding to the utterance, and the like. The NLU processing can include parsing the received user inputs 530 to understand the structure and meaning of the utterance, refining and reforming the utterance to develop a better understandable form (e.g., logical form) or structure for the utterance. The NLU processing performed can include various NLP-related processing such as sentence parsing (e.g., tokenizing, lemmatizing, identifying part-of-speech tags for the sentence, identifying named entities in the sentence, generating dependency trees to represent the sentence structure, splitting a sentence into clauses, analyzing individual clauses, resolving anaphoras, performing chunking, and the like). In certain instances, the NLU processing, or any portions thereof, is performed by the LLMs 540 themselves. In other instances, the LLMs 540 use other resources to perform portions of the NLU processing. For example, the syntax and structure of an input utterance sentence may be identified by processing the sentence using a parser, a part-of-speech tagger, a named entity recognition model, a pre-trained language model such as BERT, or the like.

Upon understanding the meaning of an utterance, the one or more LLMs 540 generate an execution plan that identifies one or more agents (e.g., agent 545A) from the list of candidate agents to execute and perform one or more actions or operations responsive to the understood meaning or goal of the user. The one or more actions or operations are then executed by the digital assistant 515A on one or more assets (e.g., asset 550A—knowledge, API, SQL operations, etc.) and/or the context and memory store. The execution of the one or more actions or operations generates output data from one or more assets and/or relevant context and memory information from a context and memory store comprising context for a present conversation with the digital assistant 515A. The output data and relevant context and memory information are then combined with the user input 530 to construct an output prompt for one or more LLMs 540. The LLMs 540 synthesize the response 535 to the user input 530 based on the output data and relevant context and memory information, and the user input 530. The response 535 is then sent to the user 525 as an individual response or as part of a conversation with the user 525.

For example, a user input 530 may request a pizza to be ordered by providing an utterance such as "I want to order a pizza." Upon receiving such an utterance, digital assistant 515A is configured to understand the meaning or goal of the utterance and take appropriate actions. The appropriate actions may involve, for example, providing responses 535 to the user with questions requesting user input on the type of pizza the user desires to order, the size of the pizza, any toppings for the pizza, and the like. The questions requesting user may be generated by executing an action via an agent (e.g., agent 545A) on a knowledge asset (e.g., a menu for a pizza restaurant) to retrieve information that is pertinent to ordering a pizza (e.g., to order a pizza a user must provide type, seize, topping, etc.). The responses 535 provided by digital assistant 515A may also be in natural language form and typically in the same language as the user input 530. As part of generating these responses 535, digital assistant 515A may perform natural language generation (NLG) using the one or more LLMs 540. For the user ordering a pizza, via the conversation between the user and digital assistant 515A, the digital assistant 515A may guide the user to provide all the requisite information for the pizza order, and then at the end of the conversation cause the pizza to be ordered. The ordering may be performed by executing an action via an agent (e.g., agent 545A) on an API asset (e.g., an API for ordering pizza) to upload or provide the pizza order to the ordering system of the restaurant. Digital assistant 515A may end the conversation by generating a final response 535 providing information to the user 525 indicating that the pizza has been ordered.

While the various examples provided in this disclosure describe and/or illustrate utterances in the English language, this is meant only as an example. In certain embodiments, digital assistants 515 are also capable of handling utterances in languages other than English. Digital assistants 515 may provide subsystems (e.g., components implementing NLU functionality) that are configured for performing processing for different languages. These subsystems may be implemented as pluggable units that can be called using service calls from an NLU core server. This makes the NLU processing flexible and extensible for each language, including allowing different orders of processing. A language pack may be provided for individual languages, where a language pack can register a list of subsystems that can be served from the NLU core server.

While the embodiment in FIG. 5 illustrates the digital assistant 515A including one or more LLMs 540 and one or more agents 545A-N, this is not intended to be limiting. A digital assistant can include various other components (e.g., other systems and subsystems as described in greater detail with respect to FIG. 6) that provide the functionalities of the digital assistant. The digital assistant 515A and its systems and subsystems may be implemented only in software (e.g., code, instructions stored on a computer-readable medium and executable by one or more processors), in hardware only, or in implementations that use a combination of software and hardware.

Figure 6:
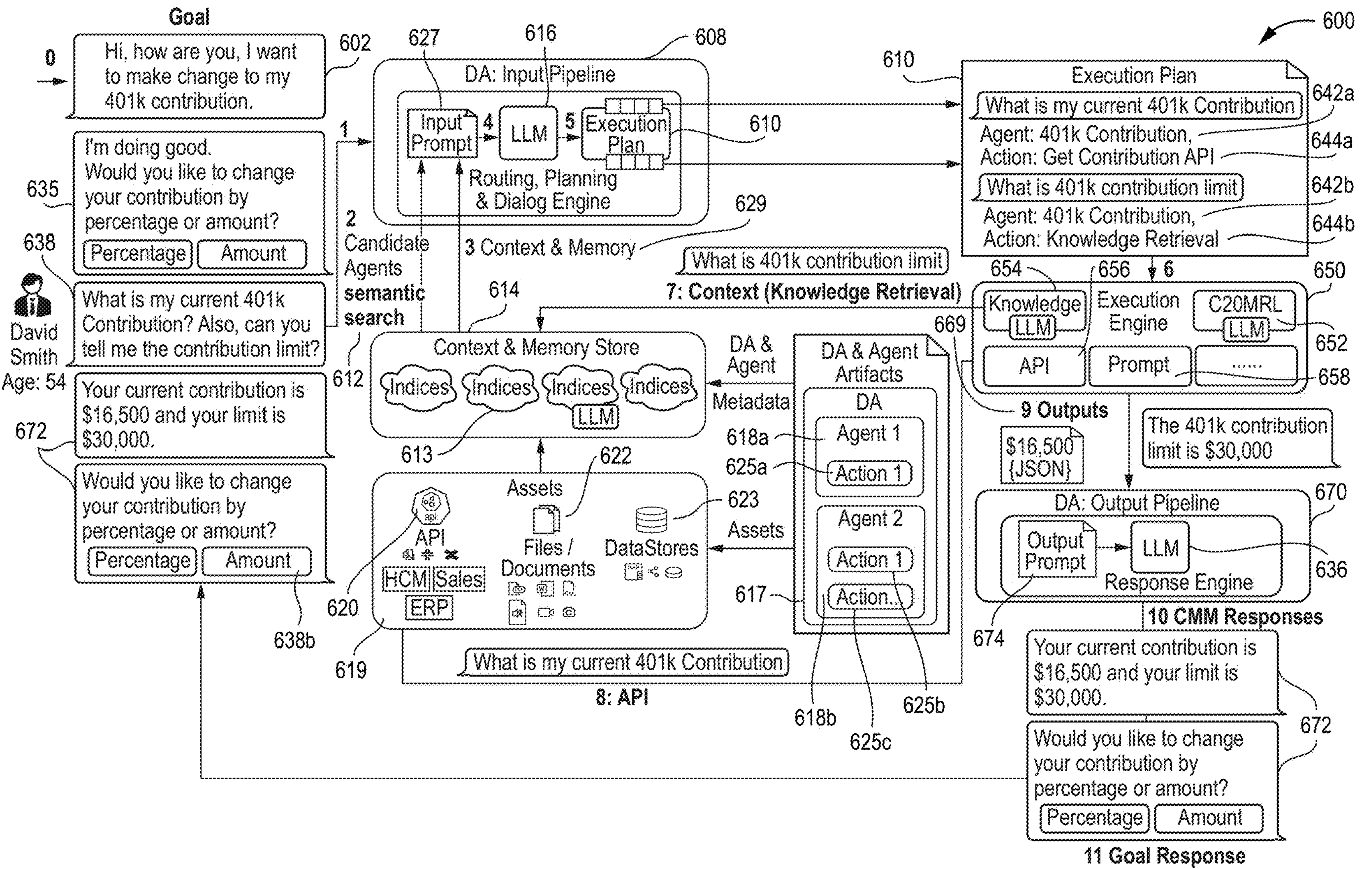
FIG. 6 is an exemplary architecture for an LLM-based digital assistant in accordance with various embodiments.

FIG. 6 is an example of an architecture for a computing environment 200 for a digital assistant implemented with generative artificial intelligence in accordance with various embodiments. As illustrated in FIG. 6, an infrastructure and various services and features can be used to enable a user to interact with a digital assistant (e.g., digital assistant 515A described with respect to FIG. 5) based at least in part on a series of prompts such as a conversation and/or a series of actions such as interactions with a user interface. The following is a detailed walkthrough of a conversation flow and the role and responsibility of the components, services, models, and the like of the computing environment 600 within a conversation flow. In this walkthrough, it is assumed that a user "David" is interested in making a change to his 401k contribution, and in an utterance 602, David provides the following input: Hi, how are you, I want to make a change to my 401k contribution. The utterance 602 can be communicated to the digital assistant (e.g., via a digital assistant user interface such as a text dialogue box or microphone). At this stage upon receipt of the utterance 602, a sessionizer creates a new session or retrieves the current session context and a user message publisher updates session transcript and LLM message history with the new user message (e.g., utterance 602).

In instances where the user provides the utterance 602 and/or performs an action while using an application supported by a digital assistant, the application issues update application context commands as the user interacts with the application (e.g., provides an utterance via text or audio, triggers a user interface element, navigates between pages of the application, and the like). Whenever an update application context command message is received by the digital assistant from the application, the application context processor (part of the context manager) is implemented. The application context processor performs the following tasks: (i) manages dialog threads based on the application context message, e.g., if the threadId specified with the message doesn't exist yet, a new dialog thread is created and made current, and if the threadId already exists, the corresponding dialog thread is made current, (ii) creates or updates the application context object for the current dialog thread, (iii) if a service call ID such as a REST request ID is included, the application context may be enriched (as described in greater detail herein). As should be understood, the application context only contains information that reflects the state of the application user interface and plugins (if available), it does not contain other state information (e.g., user or page state information/context).

Is some instances, when an update application context command message is received, an application event processor checks on whether the update application context command message includes an event definition. The event is uniquely identified by the following properties in the message payload: (i) context: the context path and/or the plugin path (For a top-level workspace plugin the context is set to the plugin name, for nested plugins the plugin path is included where plugins are separated with a slash, for example Patient/Vitalschart), (ii) eventType: the type of event can be one of the built in events or a custom event, and (iii) semantic object: the semantic object to which the event applies. An event can be mapped to one or more actions, and the message payload properties can be mapped to action parameters. This mapping takes place through an application event subscription. Each property in the message payload can be mapped to an agent action parameter using an application event property mapping.

In some instances, the utterance 602 and/or action performed by the user is provided directly as input to a planner 608. In other instances where the application event processor is implemented, the utterance 602 and/or action performed by the user is provided as input to the planner 608 when the application event processor determines an event such as receipt of utterance 602 is mapped to an agent or action associated with the digital assistant. The planner 608 is used by the digital assistant to create an execution plan 610 with specified parameters either from the utterance 602, the action performed by the user, the context, or any combination thereof. The execution plan 610 identifies one or more agents and/or one or more actions for the one or more agents to execute in response to the utterance 602 and/or action performed by the user.

A two-step approach can be taken via the planner 608 to generate the execution plan 610. First, a search 612 can be performed to identify a list of candidate agents and/or actions. The search 612 comprises running a query on indices 613 (e.g., semantic indices) of a context and memory store 614 based on the utterance 602 and/or action performed by the user. In some instances, the search 612 is a semantic search performed using words from the utterance 602 and/or representative of the action performed by the user. The semantic search uses NLP and optionally machine learning techniques to understand the meaning of the utterance 602 and/or action performed by the user and retrieve relevant information from the context and memory store 614. In contrast to traditional keyword-based searches, which rely on exact matches between the words in the query and the data in the context and memory store 614, a semantic search takes into account the relationships between words, the context of the query and/or action, synonyms, and other linguistic nuances. This allows the digital assistant to provide more accurate and contextually relevant results, making it more effective in understanding the user's intent in the utterance 602 and/or action performed by the user.

In order to run the query, the planner 608 calls the context and memory store 614 (e.g., a semantic index of the context and memory store 614) to get the list of candidate agents and/or actions. The following information is passed in the call: (i) the ID of the digital assistant (the ID scopes the set of agent and/or actions the semantic index will search for and thus the agents and/or actions must be part of the digital assistant), and (ii) the last X number of user messages and/or actions (e.g., X can be set to the last 5 turns), which can be configurable through the digital assistant settings.

The context and memory store 614 is implemented using a data framework for connecting external data to LLMs 616 to make it easy for users to plug in custom data sources. The data framework provides rich and efficient retrieval mechanisms over data from various sources such as files, documents, datastores, APIs, and the like. The data can be external (e.g., enterprise assets) and/or internal (e.g., user preferences, memory, digital assistant, and agent metadata, etc.). In some instances, the data comprises metadata extracted from artifacts 617 associated with the digital assistant and its agents 618 (e.g., 618*a* and 618*b*). The artifacts 617 for the digital assistant include information on the general capabilities of the digital assistant and specific information concerning the capabilities of each of the agents 618 (e.g., actions) available to the digital assistant (e.g., agent artifacts). Additionally or alternatively, the artifacts 617 can encompass parameters or information associated with the artifacts 617 and that can be used to define the agents 618 in which the parameters or information associated with the artifacts 617 can include a name, a description, one or more actions, one or more assets, one or more customizations, etc. In some instances, the data further includes metadata extracted from assets 619 associated with the digital assistant and its agents 618 (e.g., 618*a* and 618*b*). The assets 619 may be resources, such as APIs 620, files and/or documents 622, data stores 623, and the like, available to the agents 618 for the execution of actions (e.g., actions 625*a*, 625*b*, and 625*c*). The data is indexed in the context and memory store 614 as indices 613, which are data structures that provide a fast and efficient way to look up and retrieve specific data records within the data. Consequently, the context and memory store 614 provides a searchable comprehensive record of the capabilities of all agents and associated assets that are available to the digital assistant for responding to the request and/or action.

The response of context and memory store 614 is converted into a list of agent and/or action instances that are not just available to the digital assistant for responding to the request but also potentially capable of facilitating the generation of a response to the utterance 602 and/or action performed by the user. The list of candidate agents and/or actions includes the metadata (e.g., metadata extracted from artifacts 617 and assets 619) from the context and memory store 614 that is associated with each of the candidate agents and/or actions. The list can be limited to a predetermined number of candidate agents and/or actions (e.g., top 10) that satisfy the query or can include all agents and/or actions that satisfy the query. The list of candidate agents and/or actions with associated metadata is appended to the utterance 602 and/or action performed by the user to construct an input prompt 627 for the LLM 616. The search 612 is important to the digital assistant because it filters out agents and/or actions that are unlikely to be capable of facilitating the generation of a response to the utterance 602 and/or action performed by the user. This filter ensures that the number of tokens (e.g., word tokens) generated from the input prompt 627 remains under a maximum token limit or context limit set for the LLM 616. Token limits represent the maximum amount of text that can be inputted into an LLM. This limit is of a technical nature and arises due to computational constraints, such as memory and processing resources, and thus makes certain that the LLMs can take the input prompt as input.

In some instances, one or more knowledge actions are additionally appended to the list of candidate agents and the utterance 602. The knowledge actions allow for additional knowledge to be acquired that is pertinent to the utterance 602 and/or action performed by the user (this knowledge is typically outside the scope of the knowledge used to train an LLM of the digital assistant). The are two types of knowledge action sources: (i) structure: the knowledge source defines a list of pre-defined questions that the user might ask and exposes them as some APIs (e.g., Multum), and (ii) unstructured: with the knowledge source, the user has unlimited ways to ask questions and the knowledge source exposes a generic query interface (e.g., medical documents (SOAP notes, discharge summary, etc.)).

In some instances, conversation context 629 concerning the utterance 602 are additionally appended to the list of candidate agents and the utterance 602. The conversation context 629 can be retrievable from one or more sources including the context and memory store 614, and includes user session information, dialog state, conversation or contextual history, application context, page context, user information, or any combination thereof. For example, the conversation context 629 can include: the current date and time, needed to resolve temporal references in user query like "yesterday", or "next Thursday", additional context, which contains information such as user profile properties and application context groups with semantic object properties, and the chat history with the digital assistant (and/or other digital assistant or system internal or external to the computing environment 600.

The second step of the two-step approach is for the LLM 616 to generate an execution plan 610 based on the input prompt 627. The LLM 616 can be invoked by creating an LLM chat message with role system passing in the input prompt 227, converting the candidate agents and/or actions into LLM function definitions, retrieving a proper LLM client based on the LLM configuration options, optionally transforming the input prompt 627, LLM chat message, etc. into a proper format for the LLM client, and sending the LLM chat message to the LLM client for invoking the LLM 616. The LLM client then sends back an LLM success response in CLMI format or a provider specific response is converted back to the LLM success response in CLMI format using an adapter such as OpenAIAdapter (or send back or is converted to an LLM error response in case an unexpected error occurred). An LLM call instance is created and added to the conversation history which captures all the request and response details including the execution time.

The LLM 616 has a deep generative model architecture (e.g., a reversible or autoregressive architecture with) for generating the execution plan 610. In some instances, the LLM 616 has over 100 billion parameters and generates the execution plan 610 using autoregressive language modeling within a transformer architecture, allowing the LLM 616 to capture complex patterns and dependencies in the input prompt 627. The LLM's 616 ability to generate the execution plan 610 is a result of its training on diverse and extensive textual data, enabling the LLM to understand human language across a wide range of contexts. During training, the LLM 616 learns to predict the next word in a sequence given the context of the preceding words. This process involves adjusting the model's parameters (weights and biases) based on the errors between its predictions and the actual next words in the training data. When the LLM 616 receives an input such as the input prompt 627, the LLM 616 tokenizes the text into smaller units such as words or sub-words. Each token is then represented as a vector in a high-dimensional space. The LLM 616 processes the input sequence token by token, maintaining an internal representation of context. The LLM's 616 attention mechanism allows it to weigh the importance of different tokens in the context of generating the next word. For each token in the vocabulary, the LLM 616 calculates a probability distribution based on its learned parameters. This probability distribution represents the likelihood of each token being the next word given the context. For example, to generate the execution plan 610, the LLM 616 samples a token from the calculated probability distribution. The sampled token becomes the next word in the generated sequence. This process is repeated iteratively, with each newly generated token influencing the context for generating the subsequent token. The LLM 616 can continue generating tokens until a predefined length or stopping condition is reached.

In some instances, as illustrated in FIG. 6, the LLM 616 may not be able to generate a complete execution plan 610 because it is missing information such as if more information is required to determine an appropriate agent for the response, execute one or more actions, or the like. In this particular instance, the LLM 616 has determine that in order to change the 401k contribution as request by the user, it is necessary to understand whether the user would like to change the contribution by a percentage or certain currency amount. In order to obtain this information, the LLM 616 (or another LLM such as LLM 636) generates end-user response 635 (I'm doing good. Would you like to change your contribution by percentage or amount?[Percentage] [Amount]) to the input prompt 627 that can obtain the missing information such that the LLM 616 is able to generate a complete execution plan 610. In some instances, the response may be rendered within a dialogue box of a UI having one or more UI elements allowing for an easier response by the user. In other instances, the response may be rendered within a dialogue box of a UI allowing for the user to reply using the dialogue box (or alternative means such as a microphone). In this particular instance, the user responds with an additional query 638 (What is my current 401k Contribution?Also, can you tell me the contribution limit?) to gather additional information such that the user can reply to the response 635. The subsequent response—additional query 638—is input into the planner 608 and the same processes described above with respect to utterance 602 are executed but this time with the context of the prior utterances/replies (e.g., utterance 602 and response 635) from the user's conversation with the digital assistant. This time, as illustrated in FIG. 6, the LLM 616 is able to generate a complete execution plan 610 because it has all the information it needs.

In some instances, the utterance 602 by the user may be determined by the LLM 616 to be non-sequitur (i.e., an utterance that does not logically follow from the previous utterance in a dialogue or conversation). In such an instance, an execution plan orchestrator can be used to handle the switch among different dialog paths. The execution plan orchestrator is configured to track all the ongoing conversation paths, create a new entry if a new dialog path is created and pause the current ongoing conversation if any, remove the entry if the conversation completes based on the metadata of the new action or user preference, it might generate a prompt message when starting a non-sequitur or resuming the previous one, manage the dialog for the prompt message and either proceed or restore the current conversation, confirm or cancel when the user responds to the prompt for the non-sequitur. and manages a cancel or exit from a dialog.

The execution plan 610 includes an ordered list of agents and/or actions that can be used and/or executed to sufficiently respond to the request such as the additional query 638. For example, and as illustrated in FIG. 6, the execution plan 610 can be an ordered list that includes a first agent **642*a* capable of executing a first action 644*a* via an associated asset and a second agent 642*b* capable of executing a second action 644*b* via an associated asset. The agents, and by extension the actions, may be ordered to cause the first action 644*a* to be executed by the first agent 642*a* prior to causing the second action 644*b* to be executed by the second agent 642*b*. In some instances, the execution plan 610 may be ordered based on dependencies indicated by the agents and/or actions included in the execution plan 610. For example, if executing the second agent 642*b* is dependent on, or otherwise requires, an output generated by the first agent 642*a* executing the first action 644*a*, then the execution plan 610 may order the first agent 642*a* and the second agent 642*b*** to comply with the dependency. As should be understood, other examples of dependencies are possible.

The execution plan 610 is then transmitted to an execution engine 650 for implementation. The execution engine 650 includes a number of engines, including a natural language-to-programming language translator 652, a knowledge engine 654, an API engine 656, a prompt engine 658, and the like. for executing the actions of agents and implementing the execution plan 610. For example, the natural language-to-programming language translator 652, such as a Conversation to Oracle Meaning Representation Language (C2OMRL) model, may be used by an agent to translate natural language into a intermedial logical for (e.g., OMRL), convert the intermediate logical form into a system programming language (e.g., SQL) and execute the system programming language (e.g., execute an SQL query) on an asset 619 such as data stores 623 to execute actions and/or obtain data or information. The knowledge engine 654 may be used by an agent to obtain data or information from the context and memory store 614 or an asset 619 such as files/documents 622. The API engine 656 may be used by an agent to call an API 620 and interface with an application such as retirement fund account management application to execute actions and/or obtain data or information. The prompt engine 658 may be used by an agent to construct a prompt for input into an LLM such as an LLM in the context and memory store 614 or an asset 619 to execute actions and/or obtain data or information.

The execution engine 650 implements the execution plan 610 by running each agent and executing each action in order based on the ordered list of agents and/or actions using the appropriate engine(s). To facilitate this implementation, the execution engine 650 is communicatively connected (e.g., via a public and/or provue network) with the agents (e.g., 642*a*, 642*b*, etc.), the context and memory store 614, and the assets 619. For example, as illustrated in FIG. 6, when the execution engine 650 implements the execution plan 610, it will first execute the agent 642*a* and action 644*a* using API engine 656 to call the API 620 and interface with a retirement fund account management application to retrieve the user's current 401k contribution. Subsequently, the execution engine 650 can execute the agent 642*b* and action 644*b* using knowledge engine 654 to retrieve knowledge on 401k contribution limits. In some instances, the knowledge is retrieved by knowledge engine 654 from the assets 619 (e.g., files/documents 622). In other instances (as in this particular instance), the knowledge is retrieved by knowledge engine 654 from the context and memory store 614. Knowledge retrieval and action execution using the context and memory store 614 may be implemented using various techniques including internal task mapping and/or machine learning models such as additional LLM models. For example, the query and associated agent for "What is 401k contribution limit" may be mapped to a 'semantic search' knowledge task type for searching the indices 613 within the context and memory store 614 for a response to a given query. By way of another example, a request such as "Can you summarize the key points relating to 401k contribution" can be or include a 'summary' knowledge task type that may be mapped to a different index within the context and memory store 614 having an LLM trained to create a natural language response (e.g., summary of key points relating to 401k contribution) to a given query. Over time, a library of generic end-user task or action types (e.g., semantic search, summarization, compare/contrast, heterogeneous data synthesis, etc.) may be built to ensure that the indices and models within the context and memory store 614 are optimized to the various task or action types.

The result of implementing the execution plan 610 is output data 669 (e.g., results of actions, data, information, etc.), which is transmitted to an output pipeline 670 for generating end-user responses 672. For example, the output data 669 from the assets 619 (knowledge, API, dialog history, etc.) and relevant information from the context and memory store 614 can be transmitted to the output pipeline 670. The output data 669 is appended to the utterance 602 to construct an output prompt 674 for input to the LLM 636. In some instances, context 629 concerning the utterance 602 are additionally appended to the output data 669 and the utterance 602. The context 629 is retrievable from the context and memory store 614 and includes user session information, dialog state, conversation or contextual history, user information, or any combination thereof. The LLM 636 generates responses 672 based on the output prompt 674. In some instances, the LLM 636 is the same or similar model as LLM 616. In other instances, the LLM 636 different from LLM 616 (e.g., trained on a different set of data, a different architecture, trained for a one or more different tasks, etc.). In either instance, the LLM 636 has a deep generative model architecture (e.g., a reversible or autoregressive architecture with) for generating the responses 672 using similar training and generative processes described above with respect to LLM 616. In some instances, the LLM 636 has over 100 billion parameters and generates the responses 672 using autoregressive language modeling within a transformer architecture, allowing the LLM 636 to capture complex patterns and dependencies in the output prompt 674.

In some instances, the end-user responses 672 may be in the format of a Conversation Message Model (CMM) and output as rich multi-modal responses. The CMM defines the various message types that the digital assistant can send to the user (outbound), and the user can send to the digital assistant (inbound). In certain instances, the CMM identifies the following message types:

- text: Basic text message
- card: A card representation that contains a title and, optionally, a description, image, and link
- attachment: A message with a media URL (file, image, video, or audio)
- location: A message with geo-location coordinates
- postback: A message with a postback payload Messages that are defined in CMM are channel-agnostic and can be created using CMM syntax. The channel-specific connectors transform the CMM message into the format required by the specific channel, allowing a user to run the digital assistant on multiple channels without the need to create separate message formats for each channel.

Lastly, the output pipeline 670 transmits the responses 672 to the end user such as via a user device or interface. In some instances, the responses 672 are rendered within a dialogue box of a GUI allowing for the user to view and reply using the dialogue box (or alternative means such as a microphone). In other instances, the responses 672 are rendered within a dialogue box of a GUI having one or more GUI elements allowing for an easier response by the user. In this particular instance, a first response 672 (What is my current 401k Contribution?Also, can you tell me the contribution limit?) to the additional query 638 is rendered within the dialogue box of a GUI. Additionally, in order to follow-up on obtaining information still required for the initial utterance 602, the LLM 636 generates another response 672 prompting the user for the missing information (Would you like to change your contribution by percentage or amount?[Percentage][Amount]).

While the embodiment of computing environment 600 in FIG. 6 illustrates the digital assistant interacting in a particular conversation flow, this is not intended to be limiting and is merely provided to facilitate a better understanding of the role and responsibility of the components, services, models, and the like of the computing environment 600 within the conversation flow.

A Digital Assistant with Copilot Support

Copilot represents a new generation of innovative user experiences aimed at enhancing application (e.g., business application) usage. With the digital assistant framework as described with respect to FIGS. 1-6, developers can create customized digital assistants comprising multiple skills, including specialized functionalities such as a ready-to-use digital assistant, which has skills like Expenses, Project Management, Human Capital Management (HCM) and more. As discussed herein, skill developers now have the ability to incorporate generative AI components such as LLMs into their skill flows which allow them to introduce generative AI capability into their existing digital assistant. With blended capabilities of the digital assistant, copilot can seamlessly integrate with applications, thus providing conversational AI and generative AI tailored experience to users' needs while using applications for various tasks.

Copilot Implementation

In order to integrate the copilot into an application such as the HCM application or a Skill Bot design application, the developer accesses the application development environment and configures the Copilot SDK integration endpoints and credentials with the DA. This streamlines the integration process, enabling the developer to efficiently incorporate copilot's digital assistant capabilities into the application.

For integration of Context Passing: The developer enables the context-aware framework features, which include the passage of application context, page context, and user-context from the application and other sources to copilot and ultimately the DA. The passage of context and ability to execute a skill or LLM component of the DA using the context may be implemented via a set of REST APIs exposed to the developer for copilot support (the Copilot SDK provides a convenience wrapper around these REST API's), which allows for a REST API's call to the digital assistant dialog pipeline by sending CMM messages that use new types of the CommandMessagePayload (start thread and update context) (CMM defines the various message types that a DA skill or LLM can send to the user (outbound), and the user can send to the DA skill or LLM (inbound)). For the start thread, the command property value in the CommandMessagePayload for the Invoke Flow command may be set as a key value such as startThread. The following properties in Table 2 may be used:

TABLE 2

| Property Name | Property Type | Description |
|---|---|---|
| skillName | String | Only required when invoking a DA |
| flowName | String | The name of the flow to invoke |
| inputParameters | JSONObject | key-value pairs where each key is the name of an input parameter as defined in the flow. The value of each input parameter will be set when invoking the flow. |

The threadId (thread identifier) of the new thread can be passed in as part of the channel conversation metadata.

For the context to be updated, the Copilot SDK can provide methods to set user, application, page (including contextual widget—e.g., obtaining context from a user's interaction with a UI element) and field context within a context variable data structure (e.g., one or more JSON conversation objects stored in association with a JSON session object). The context variable data structure can be associated with the threadId. These methods translate in CMM messages that are sent by the chat server. The command property value in the CommandMessagePayload for the update context command may be set as a key value such as updateContext. The following properties in Table 3 may be used:

TABLE 3

| Property Name | Property Type | Description |
|---|---|---|
| context | String | Includes: the name of the application the user is in, the current page the user is in, and the current field the user is in. |
| variables | JSONObject | Additional key-value pairs that are stored as skill/DA-scoped variables |

For user context, using SDK APIs the developer can configure the CommandMessagePayload to pass User's First Name, Last Name, Email, Job Title, Department, Work Location, preferences such as Language, time zone, date format, and the like. For application context, using SDK APIs the developer can configure the CommandMessage-Payload to pass the navigations such as "Navigation: Home". For the page context, with controls available, the developer has options to either pass full page content to the copilot or choose as per need. For example, the developer can decide not to pass it fully for Home Page as it might not have the right applicability. So, the developer configures the copilot to pass the page context such as Current Page view viz Home view of application, using the SDK APIs. These contexts and CMM messages enable defining declaratively the functionality of the copilot to obtain and synchronize application context (app, page, field) within the context variable data structure. Based on context within the context variable data structure, routing rules are used by the copilot to invoke a conversation flow between the DA/Skill and user (support routing to various Skills or LLMs within the DA system), and trigger actions based on the current context (e.g., to assist application navigation based on indicated context). Advantageously, this provides a personalized conversation starter prompt and dialogue, which is conveyed to the user via an interface of Copilot.

To support contextually aware routing, a copilot routing section can be added to the dialog engine of the DA via skill settings for supporting routing. The copilot routing section defines the routing rules when receiving an updateContext CommandMessagePayload. The routing rules map various applications, application components, pages, page content, etc. to various skills, LLMs, and/or dialog flows. For example, the routing section may contain a table (see example Table 4) with the following fields:

TABLE 4

| Property | Required | Description |
|---|---|---|
| applicationName | Yes | The name of the application the user is in |
| pageName | No | The name of the current page the user is located in |
| flowName | Yes | The flow that should be invoked when the updateContext CommandMessagePayload contains the specified application name, and optionally the page name. |

Here is an example (see example Table 5) of how this table may be populated in the HCM use case (where the 3 context property values from Tables 3 and 4 may be hcm, hcm: jobDescription, and hcm:benefits):

TABLE 5

| Application | Page | Flow |
|---|---|---|
| hcm | | HomeFlow |
| hcm | jobDescription | JobDescriptionFlow |
| hcm | benefits | BenefitsFlow |

With this routing configuration in place, an updateContext command message can be processed as follows:

1. Internally, a thread concept can be used (similar to that used with the Interaction Modalities of copilot). Each flow that is triggered through an updateContext command message, will run on its own thread. This allows the state to be maintained per running flow, so when the user switches between pages, the correct thread can be resumed, and the state associated with that thread can be restored. States that need to be shared across threads can be stored in skill-scoped variables. The Copilot SDK can simply ignore the threadId that will be included in the channel conversation metadata of the bot responses.
2. The flow that matches the applicationName is looked up using the table, and optionally the flowName as specified in the message.
3. Then check if there is an existing thread running within the session with the threadId set to the flow name.
   a. If no such thread exists, the flow is invoked using a new thread with the threadId set to the flow name.
   b. If such a thread exists, the thread is resumed.
4. Introduce a new system.coPilotContext variable that holds a map with application name, page name and field name
5. The optional variables that are passed in with the the updateContext CommandMessagePayload are stored within a new skill/DA-scoped variable named, system-.coPilotContext. This variable may be a JSONObject with each key containing the variable name, and the value the variable value.

As a validation step, the developer can test the context-aware feature in the application UI by manually navigating to a page such as the Benefits section of the HCM application and launching the side-panel chat. The developer is able to see a personalized and contextual response from the Copilot "Hi Michael, What more information you require on your benefits plan?", with suggested actions like "Summarize Medical Benefits", "What is my upper limit", "How much I have to Co-pay?". The developer may then select summarize medical benefits action and get to see the summary.

Follows is an end user example:

To initiate the recruitment process, Sarah logs into the Oracle HCM system. It's been 12 months since she last hired someone and doesn't fully recall how the process works and the system has also been upgraded since then. Sarah is afraid as her 30 mins are going to be spent just figuring out what she needs to-do and not actually posting the job reqs.

Sarah is overwhelmed by the broad set of options and menus on the HCM landing page but a small welcoming button catches her eye in the bottom right of the page. She's seen similar chat buttons on her favorite e-tailer sites so she clicks on it. The chat window expands into side-panel chat and Sarah is greeted by the HCM Copilot:

"Hi Sarah, I'm your HCM Copilot. I can help you with:

Your employee self-service tasks

Managing your team

Hiring and onboarding new team members"

Sarah is relieved that this copilot will be able to help her with her hiring task. Behind the scenes the copilot is contextually aware of Sarah's profile and the current application view (home), it knows she's an employee, also a manager & currently on the home view of the application and hence provides the appropriate bullets in its greeting.

As Sarah's aim is to create a Job Requisition for a Senior App Developer, she navigates by herself to Job Requisition Creation Page.

Sarah sees 6 sections to be filled out by her in-total. Copilot gets the application and page context about different section and type of fields.

Sarah sees that in opened side-panel chat, the Copilot now responds, "How can I help you with your Job Requisition Creation?". She can type or, better yet, use her microphone to talk to the copilot. She clicks the microphone icon and engages the copilot.

Sarah says: "I need to create a new Job Requisition for a Senior Application Developer. Can you assist me?"

Copilot acknowledges Sarah's request and asks targeted questions about the new job opening, such as Job Level, Location and required qualifications.

Copilot: "To create the Job Requisition, I'll need some details. What will be the Job Level, Location and required minimum qualification?"

Sarah: "This will be a full-time remote worker in US and working for our client's project which requires full-stack tech skills corley into java"

Copilot acknowledges Sarah's response. Behind the scenes, Copilot is getting to know about page context of Sarah's Current view, which includes available elements as per the form. And is also able to update the fields with the provided data by Sarah. But before that, Copilot seeks confirmation from Sarah.

Copilot: "Thanks Sarah, I will guide you step by step through the job requisition process. Do you want me to auto-fill some of the gathered data?" with option "Yes" or "No"

Interface Modalities

The side-panel chat is a chat interface, where users can interact with copilot while still having full visibility of the application. The side-panel chat is context aware UI embedded within the application, and shows generated responses from Skills and LLM components of the DA. For example, the side-panel chat is capable of (i) determining the context for a task to be performed using an application when a user opens a specific page within the application like Benefits Page, Job Requisition page, (ii) routing CMM messages to appropriate Skills and LLMs of the DA based on the context and routing rules, and (iii) displaying the contextual responses from the DA. The side-panel chat also provides capability to copilot for understanding and correlating information being asked/input with what is available on the page view. And offers to the user the ability to update the page input area or fields value from either the generated content or as per user input.

Follows is an end user example:

To initiate the recruitment process, Sarah logs into the Oracle HCM system. It's been 12 months since she last hired someone and doesn't fully recall how the process works and the system has also been upgraded since then. Sarah is afraid as her 30 mins are going to be spent just figuring out what she needs to-do and not actually posting the job reqs.

Figure 7:
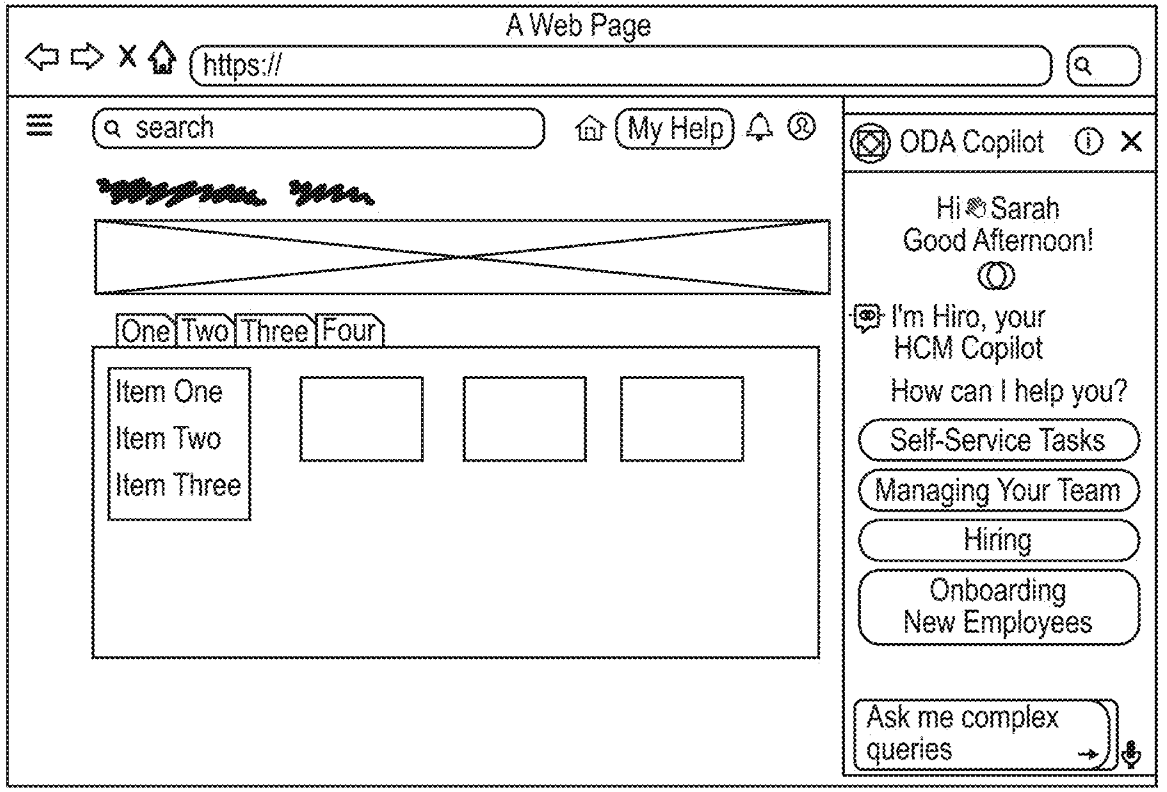
FIG. 7 illustrates a side-panel chat as part of a Copilot UI in accordance with various embodiments.

Sarah is overwhelmed by the broad set of options and menus on the HCM landing page but a small welcoming button catches her eye in the bottom right of the page. She's seen similar chat buttons on her favorite e-tailer sites so she clicks on it. The chat window expands (shown in FIG. 7) into side-panel chat and Sarah is greeted by the HCM Copilot: "Hi Sarah, I'm your HCM Copilot. I can help you with:

Your employee self-service tasks

Managing your team

Hiring and onboarding new team members"

Sarah is relieved that this copilot will be able to help her with her hiring task. Behind the scenes the copilot is contextually aware of Sarah's profile and the current application view (home), it knows she's an employee, also a manager and currently on the home view of the application and hence provides the appropriate bullets in its greeting.

Figure 8:
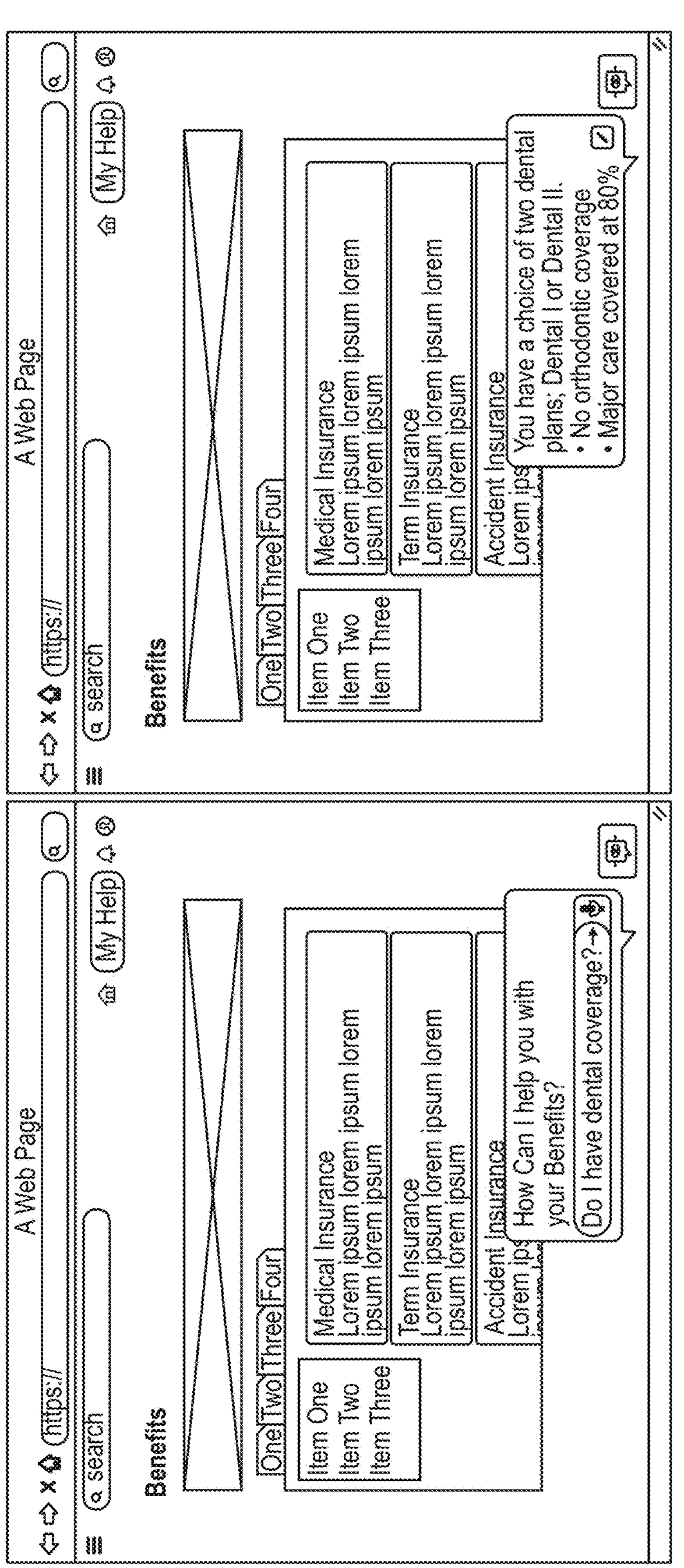
FIG. 8 illustrates a micro-conversation mode as part of a Copilot UI in accordance with various embodiments.

The micro-conversation mode is a chat-style user interface designed to facilitate quick and focused single-turn interactions. It provides a simple and condensed chat-like interface where the user can input queries and receive single responses at a time. As illustrated in FIG. 8, the micro-conversation mode provides: Quick Interactions: For simple and quick interactions where users need to receive concise responses one at a time, the micro-conversation UI view is suitable. It focuses on delivering essential information without overwhelming the user with a full chat interface. Space Constraints: In scenarios where the application's user interface has limited space, such as narrow sidebars, the micro-conversation UI can be more efficient in utilizing the available real estate.

There are Four Types of Micro-conversation interactions:

1. A user initiates the chat by clicking on Chat icon button at a location such as the bottom right, which expands to micro chat style view, greets the user in a contextual way and offers way to input the query through text or microphone.
2. Automatically Activates Micro-conversation, when the detection of an event like a certain content is highlighted on the application page. Application passes the selected page content to the micro-conversation and offers contextual and pro-active assistance.
3. Developer wants to explicitly invoke micro-conversation UI for a certain section when user clicks on a button like help or info tool-tip.
4. Inline Contextual Widget for Input Fields: The inline contextual widget is a component that appears within input fields or near user interactions, providing real-time suggestions, content generation based on the context. It assists users as they interact with various elements on the page, guiding them through the input process. For example, when user brings the Job description text area in focus, Inline Contextual widget gets activated which has the context about the field/elements and offer suggestive actions like "Auto Generate Content". Once Content is generated it offers pre-defined actions to format or refine the output the way user wants, e.g., Improve & Rephrase (Refine), Shorten, Elaborate, Fix Grammar, or Undo.

Follows is an end user example:

Excited about the content generation feature, Michael decided to enable the Inline Contextual widget for the Job description field in the "Create a Job Requisition" page using Copilot SDK.

So, starting with configuration, he enables the Inline Contextual Widget using SDK APIs which enables micro UI view which is inline to the JD text area field. This gets activated as soon as user clicks on the JD text area.

At this point, the SDK will pass the contents of the element to the dialog flow when invoked. At an initial state, the element is empty.

When the flow is invoked, the SDK passes the contents of the text area into the current_job_description parameter.

The JD_Flow responds back with a payload that describes the state of the contextual widget:

'Auto-generate' action

Stop action (disabled)

So, Michael, can now click the Auto-generate action and invoke the flow which then return another payload:

Generated job description ("streamed")

Free form message input

To support the micro conversations on a single page, the concept of multi-turn chat using text input or action buttons within an Inline Contextual widget may be introduced as follows: (1) All required information is passed in when the user starts interacting with the widget buttons, see next points. (2) When configuring a widget for a field, the co-pilot SDK allows the developer to configure the list of initial button actions when the widget is activated, this may be a static list of actions. When the user starts interacting with the widget by clicking on one of the buttons, the LLM bot response includes a new list of dynamic actions that will replace the initial static list of actions. (3) When configuring a button for a contextual widget, the developer is able to configure the following properties:

1. buttonLabel: the label of the button
2. flowName: the name of the flow that will be invoked.
3. skillName: optional, may be used when copilot skill is a DA
4. fieldInputParameters: key-value pairs with the key being the flow input parameter name, and the value the name of a field from which the value should be passed as parameter. For example:
   a. role→jobRoleField
5. additionalInputParameters: key-value pairs with the key being the flow input parameter name, and the value the value of the parameter. For example:
   a. language→'english'

(4) When the user clicks an initial button on the contextual widget, the Copilot SDK method named something such as startWidgetInteraction is called which takes the button configuration and sends the startThread command message. (The message might be sent directly, or through a REST API wrapper). The bot response text is displayed in the field associated with the widget. The bot response actions are shown as the new list of buttons with the widget. (5) An additional flag may be provided in the button configuration to tell the SDK whether the bot response should be streamed back to the field or into the contextual widget mini chat window. (6) After the thread is started using one of the INITIAL actions, the widget buttons are replaced by the actions returned as part of the bot message. These may be implemented with CMM actions, for example postback actions with a payload that can be sent back as-is to the dialog engine, similar to what happens when clicking a button in a 'normal' conversation. The only difference is that the postback message should include the threadId in the channel conversation metadata. When the user navigates away from a page with a contextual widget, then comes back at the page, and the field associated with the widget already has a value because the user interacted with the widget before, then the SDK should show the last set of action buttons as returned by the skill from the last interaction with the widget.

Threading

In order to allow for or maintaining state and context of conversations between a user and the DA, threads are used. Threading is maintaining multiple isolated conversations within a same session between a user and digital assistant. The thread identifier is main concept to switch between and determine which thread is being used or should be used. Threads are initiated as part of an executable action identified via a GenAI model such as an LLM. Alternatively, threads are initiated as part of an executable action directly identified via a UI event. The executable action has a thread ID configuration such as when specific to patient records, the thread ID=patient name [-] patient ID. The threads maintain state with conversation or task context for a particular dialogue or flow, which includes all utterances, responses, actions executed, etc. The conversation or task context is stored in the context memory store in association with the thread ID. The thread manager handles all thread IDs, states, and switching. Threading has the benefit of ensuring that utterances and actions are all grouped based on a given domain such as a patient identifier (e.g., a doctor cannot mistakenly mix data/information between patients). Threads can also be separated based on multiple domains such as per patient and per action. An ancillary technical challenge is knowing when to switch threads especially when the utterance does not match context. So, the dialogue may include a confirmation sent to user making sure they wish to switch threads.

In particular, to support the side-panel chat widget, as well as multiple micro conversations on a single page, the concept of a thread within a session may be implemented as follows. Each contextual UI widget starts a micro-conversation on its own thread. For example, if a user navigates to a specific page to do a certain task—Copilot assists with this first task using a side-panel chat supported via a first thread. And if the user has to go to another part of the application for a second task in the middle of completing the first task, the user can get help on a second thread separate from the first thread. This allows the DA to maintain separate states for different tasks or conversations within a same session.

A thread has a unique name (identifier) that the client should pass in when creating the thread. Each thread has its own flow stack (e.g. when a flow invokes another flow, or non-sequitur happens), current flow, and current state. Each thread has its own flow-scoped context variables (associated with the flows that are executed within the thread, no new thread-level context is introduced). All threads within a session share the same skill context, user context and profile context. A thread can be started by specifying a new threadId with the UpdateApplicationContextCommand message and may start a specific flow. Flow input parameters can be specified to pass in additional context from the page. Once a thread is started, the conversation in the thread can be continued by sending CMM messages as usual, with one addition: in addition to the userId which is used as session key, the threadId can be passed in as part of the channel conversation metadata. All bot response messages that are created in response to a user message that includes a threadId, will include the same threadId in the channel conversation metadata, so the Co-Pilot SDK can filter responses based on the thread. The copilot and DA can switch between threads in the same session as the user moves between various tasks or conversations.

In the example of an inline contextual widget (one of the micro-conversation interaction types), the threading may be implemented as follows. On the SessionContext, store a 'thread map' with threadId as key, and ExecutionContext as value. By default, this map only has one entry for system.mainThread, the internal thread ID may be used for 'normal' conversations. Then a ThreadPreProcessor and a ThreadPostProcessor may be added to the pipeline in the Skill Track implementation. The pre-processor executes before the Dialog Engine and picks the correct execution context for the requested thread (system.mainThread if no threadId is specified in the incoming user message), and stores this as the execution context in the session. The post-processor executes after the Dialog Engine and stores the updated execution context in the thread map. This way the Dialog Engine can remain unaware of the thread-concept.

It should be understood that although the threading implementation is described with respect to the particular use cases of side-panel chat and inline contextual widget, threading could also be used in a similar manner to maintain isolation between other objects within a same session, e.g., multiple conversations within the LLM based DA.

Design Time Implementation of Copilot

Artificial intelligence has diverse applications, with a notable evolution in the realm of digital assistants or chatbots. Originally, many users sought instant reactions through instant messaging or chat platforms. Organizations, recognizing the potential for engagement, utilized these platforms to interact with entities, such as end users, in real-time conversations. However, maintaining a live communication channel with entities through human service personnel proved to be costly for organizations. In response to this challenge, digital assistants or chatbots, also known as bots, emerged as a solution to simulate conversations with entities, particularly over the Internet. The bots enabled entities to engage with users through messaging apps they already used or other applications with messaging capabilities. Nonetheless, creating bots can be complex requiring the performance of tedious, repetitive, and time-consuming tasks for training, testing, validating, and deploying bots.

In order to address this challenge, a design time (DT) copilot was developed to streamline the creation of end-to-end working skills and LLM agents for bots (e.g., DA bots), providing a solution for bot or skill developers looking to enhance efficiency in their development processes via a bot development application (e.g., a DA application). This feature enables the rapid generation of end-to-end working skills/LLM agents and facilitates their review and modification, covering fundamental functionalities crucial for bot development. The DT copilot empowers developers to embrace a more task-oriented approach during the implementation of working skills, enabling them to concentrate on the application's requirements without getting bogged down by the intricacies of bot platform's functionality. For example, consider the process of creating an intent. Typically, a bot developer must generate an intent and add 5 to 10 examples (with a recommended minimum of 12 utterances for each intent). Following this, they need to create a flow and map the intent to the flow. However, with the DT copilot, the repetitive and time-consuming task of generating multiple variations of similar sentences to train the intent model is eliminated. Developers can now skip the tedious steps of adding identical sentences in various ways by leveraging the intelligent capabilities of the DT Copilot, which automates this process. All the bot developer needs to provide is the task they aim to accomplish within the skill or agent. The DT Copilot skill will then generate the intent, intent utterances, flow, and flow mapping. This not only expedites the skill development lifecycle but also boosts the overall productivity of bot developers.

This functionality is delivered using the above-described aspects of copilot including the two channels: the Chat Widget (a type of Micro Conversation Chat) and the side-panel chat. When a developer lands on a UI of the bot development application containing the Chat Widget, the developer can observe the widgets on each page and can activate them to obtain assistance with particular aspects of the application identified on the page. Moreover, as the developer navigates to each page of the application, the navigation triggers an embedded help menu in the side-panel chat to guide the developer through various tasks to be performed in the development of a bot. Advantageously, there is no disconnect between these two channels. When the developer updates something from the Chat Widget, the modified variable is seamlessly sent to the side-panel chat context, ensuring it does not retain obsolete values. This integration guarantees a smooth and coherent user experience across both channels.

More specifically, when a user communicates using side-panel chat an utterance or event, a skill starts with a given flow such as 'GetOperation' flow which determines the intent (including Operation and Artifact) of the user's utterance or event using a machine learning model such as generative artificial intelligence model (e.g., an LLM) and stores the intent into a variable. And once the intent is resolved, the next step of the process is dynamic, where a stored prompt is retrieved and a machine learning model such as generative artificial intelligence model (e.g., an LLM) is invoked. Each of artifact and operation combination may need a different prompt. Along with the prompt, a schema (e.g., a JSON schema or object schema) is also retrieved from a resource bundle. The schema has slot information that is then filled by the machine learning model for the given artifact and operation combination. Slot filling is the task of filling argument slots in a schema with parameters (e.g., date/time values) or variations of parameters (e.g., September 1 as compared to today or 9/1). Again, each artifact and operation may need different information or parameters from either the context or user's utterance. Once the slots in the schema are filled, another machine learning model call is initiated and the machine learning model generates the final schema so that an internal service call can be made to an API (e.g., REST API).

Figure 9:
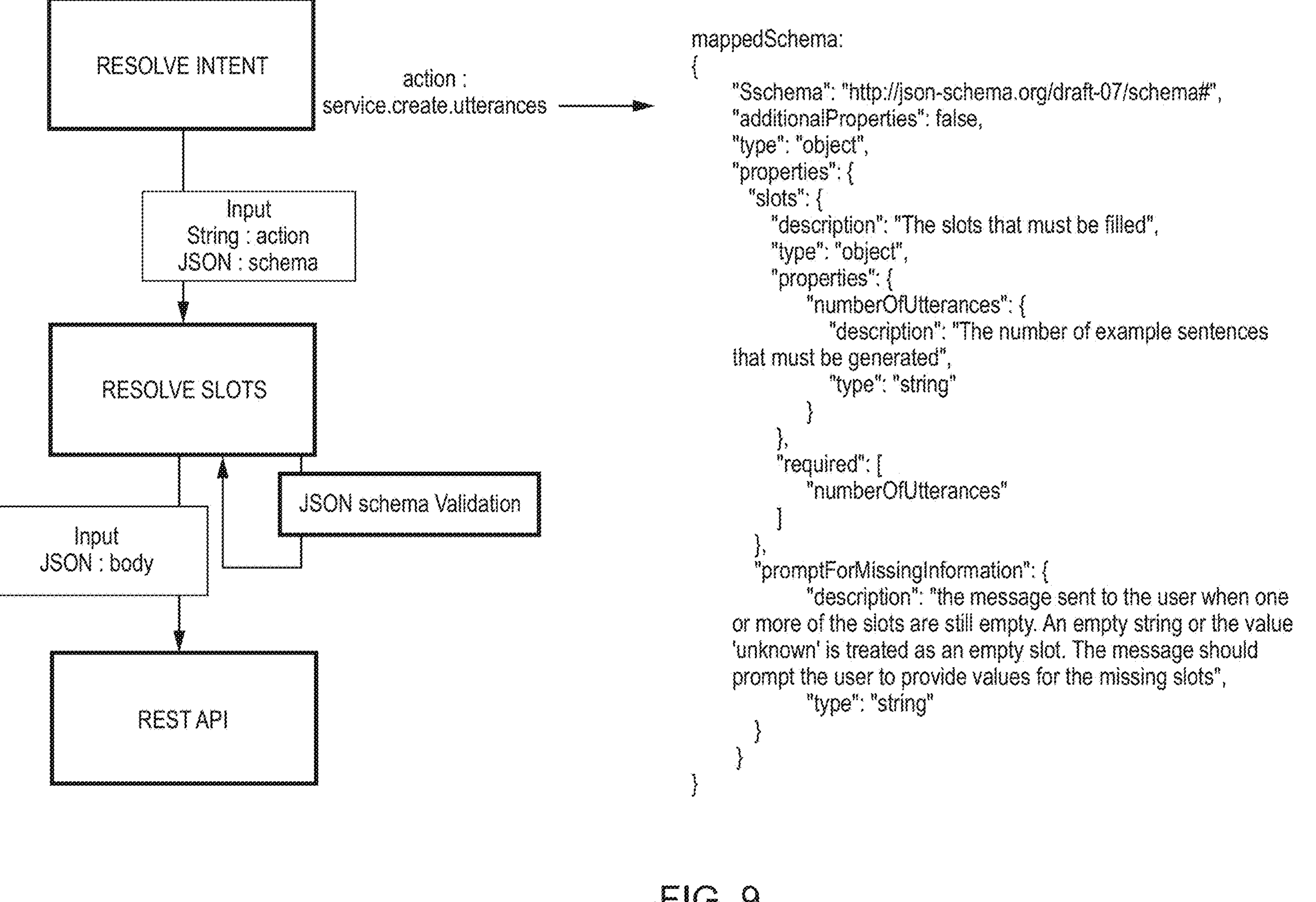
FIG. 9 is a simplified block diagram of a workflow for implementing copilot in accordance with various embodiments.

For example and as illustrated in FIG. 9, initially a message payload (e.g., a CMM message payload) may be received as described herein. The message payload may include: (i) an utterance or indication of an interface action (e.g., an event or interaction of the user with a UI element), and (ii) application context. The message payload is associated with an interaction between a user and an application (e.g., a bot development application). The message payload can trigger a flow using a thread, e.g., trigger the 'GetOperation' flow which determines the intent (including Operation and Artifact) of the user's utterance or event using a machine learning model. In some instances, a context variable data structure is generated by storing variables from the application context as at least a portion of data stored within the context variable data structure to maintain context (e.g., application context) associated with the thread.

Figure 10:
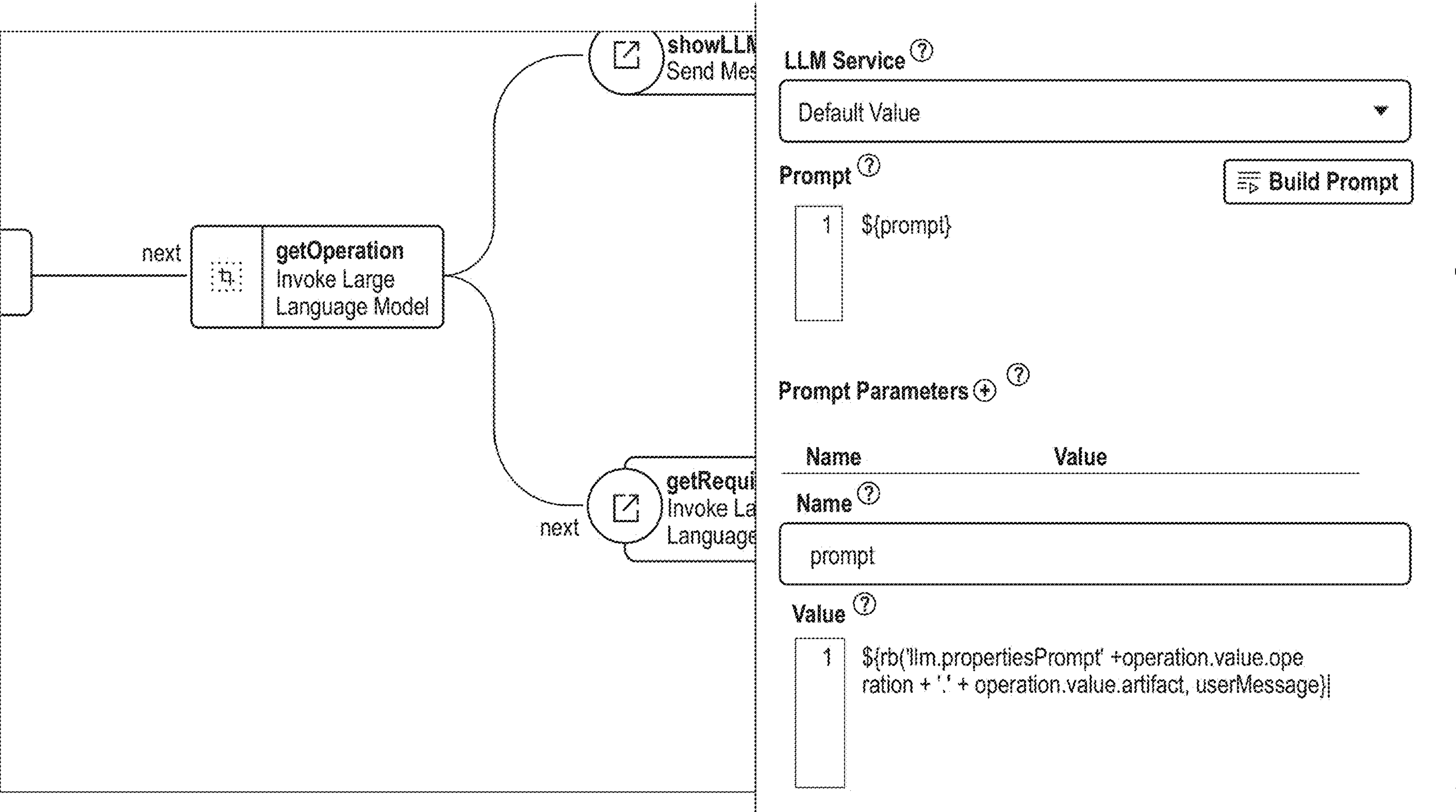
FIG. 10 illustrates identification of a prompt (having one or more prompt parameters) based on a flow and intent in accordance with various embodiments.

The machine learning model is then used to resolve the intent (including Operation and Artifact). For example, when the user's utterance is 'create intent', the machine learning model may return Operation: CREATE and Artifact: INTENT. The prompt associated with Operation: CREATE and Artifact: INTENT is retrieved. As illustrated in FIG. 10, the prompt may be used in a flow and the intent resolution is used to obtain the correct prompt for the determined intent. In some instances, there may be multiple resource bundle entries so that one or more prompts for each of Operation and Artifact can be retrieved. The prompts include executable actions and fields required to be completed by the system (e.g., prompt generator) and there is a corresponding schema for each prompt that is also retrieved. To get the schema, a similar technique may be used to dynamically retrieve the correct schema from the resource bundle. In some instances, a skill can be stored in the resource bundle in replacement of the schema, where the skill includes the schema.

Each service skill invokes a reusable flow to resolve the slots, passing to the machine learning model the prompt and schema that defines the slots that need to be filled. Resolving the slots may comprise generating, using the machine learning model, a list comprising one or more executable actions based on the prompt. The one or more executable actions comprising argument slots to be filled. This slot filling process included: deriving one or more parameters (e.g., data and time values, name values, location values, currency values, etc.) from the message payload, the data in the context variable data structure, or any combination thereof, and filling the argument slots of the one or more executable actions with a version of the one or more parameters (e.g., the original version derived from the utterance or context or a standardized or normalized value for the parameter) that conforms to the schema.

The machine learning model used to resolve the slots validates against the schema validation and ensures that the user is prompted for any missing information. For example, if the current utterance and context includes information or parameters for skillName and skillPurpose, the machine learning model fills in those argument slots in the schema. Otherwise, the machine learning model can return a message to the user to fill up the missing information. During runtime, if message ForMissingInformation is not null, then the machine learning model event handler can send that message back to user for the additional information or parameters. Once all required slots have been filled, then the schema can be sent to a machine learning model and the machine learning model generates the final schema so that an internal service call can be made to a management API (e.g., REST API), as shown in FIG. 11. In particular, the machine learning model is invoked to create a schema payload (e.g., JSON payload) required to generate DA artefacts. The LLM component or similar component may be used to constrict the schema payload that is required to make the final call to the management API that creates the DA artefacts for carrying out the task associated with the intent (e.g., create cancelPizza Intent for a skill). Thereafter, the appropriate management API is invoked via the call and the application executes the task associated with the intent. As part of executing the task, the management API or another component of the DA (e.g., dialogue engine) may communicate output or a communication derived from the output from executing actions for competing the task to the user.

In instances where the utterance, event, context, or any combination thereof conflict with one another, the machine learning model is trained to still determine the correct intent of the user. For example, if a user is at the orderPizza Intent creation page of a skill development application, and the user tells the DA via copilot that they want to create a "cancel a Pizza intent", then the machine learning model should disregard the current context orderPizza and return cancelPizza as the correct intent of the user.

FIG. 12 is a flowchart of a process 1200 for maintaining state and context of conversations between a user and digital assistant using threads in accordance with various embodiments. The processing depicted in FIG. 12 may be implemented in software (e.g., code, instructions, program) executed by one or more processing units (e.g., processors, cores) of the respective systems, hardware, or combinations thereof. The software may be stored on a non-transitory storage medium (e.g., on a memory device). The process presented in FIG. 12 and described below is intended to be illustrative and non-limiting. Although FIG. 12 illustrates the various processing steps occurring in a particular sequence or order, this is not intended to be limiting. In certain alternative embodiments, the steps may be performed in some different order or some steps may also be performed at least partially in parallel. The example method 1200 may be performed by some or all components of any device, system, or apparatus illustrated and described herein with respect to FIGS. 1-11 and 13-17.

The process 1200 may begin at step 1205 where a natural language utterance is received (at a digital assistant) from a user during a session between the user and the digital assistant.

At step 1210, a topic context instance is obtained for the natural language utterance.

At step 1215, a list is generated by a GenAI model. The list comprises an executable action based on one or more candidate actions associated with the topic context instance.

At step 1220, the executable action is executed to produce an output. The executing comprises: determining there is no thread running within the session that is associated with the topic context instance, the executable action, or both, responsive to determining there is no thread running, creating a thread associated with the topic context instance, the executable action, or both, wherein the thread maintains the topic context instance, the executable action, or both as a separate context from that of context associated with any other conversations for a distinct conversation comprising the natural language utterance between the user and the digital assistant, and executing, using the thread, the executable action to obtain the output At step 1225, the output or a communication derived from the output is sent to the user.

In some instances, the process 1200 further includes: receiving, at the digital assistant, a subsequent natural language utterance from the user during the session between the user and the digital assistant; obtaining the topic context instance for the natural language utterance; generating, by the GenAI model, another list comprising another executable action based on one or more candidate actions associated with the topic context instance; executing the another executable action, wherein the executing comprises: identifying the thread running within the session is associated with the topic context instance, the executable action, or both, determining the another executable action should be executed using the thread based on an identifier associated with the topic context instance, the executable action, or both, and executing, using the thread, the another executable action to obtain another output; and sending the another output or a communication derived from the another output to the user.

In some instances, the process 1200 further includes: receiving, at the digital assistant, a subsequent natural language utterance from the user during the session between the user and the digital assistant; obtaining a topic context instance for the subsequent natural language; generating, by the GenAI model, another list comprising another executable action based on one or more candidate actions associated with the topic context instance for the subsequent natural language utterance; executing the another executable action, wherein the executing comprises: identifying the thread running within the session is associated with the topic context instance for the natural language utterance, the executable action, or both, determining there is no thread running within the session that is associated with the topic context instance for the subsequent natural language utterance, the another executable action, or both, responsive to determining there is no thread running within the session that is associated with the topic context instance for the subsequent natural language utterance, creating another thread having an identifier associated with the topic context instance for the subsequent natural language utterance, the another executable action, or both, wherein the another thread maintains the topic context instance for the subsequent natural language utterance, the another executable action, or both as a separate context for another distinct conversation between the user and the digital assistant, and executing, using the another thread, the another executable action to obtain another output; and sending the another output or a communication derived from the another output to the user.

In some instances, the process 1200 further includes: responsive to identifying the thread running within the session is associated with the topic context instance for the natural language utterance, the executable action, or both and determining there is no thread running within the session that is associated with the topic context instance for the subsequent natural language utterance, sending a confirmation communication to the user requesting confirmation of the subsequent natural language utterance, the topic context instance for the subsequent natural language utterance, or both; and receiving, at the digital assistant, a confirmation utterance from the user that confirms the subsequent natural language utterance, the topic context instance for the subsequent natural language utterance, or both, wherein responsive to determining there is no thread running within the session that is associated with the topic context instance for the subsequent natural language utterance and receipt of the confirmation utterance, creating the another thread.

In some instances, the process 1200 further includes: receiving a message payload comprising: (i) a subsequent utterance or indication of an event, and (ii) application context, associated with an interaction between a user and an application; identifying an identifier associated with the subsequent utterance or the indication of the interface action, (ii) the application context, or (iii) both; determining the identifier associated with the subsequent utterance or the indication of the interface action, (ii) the application context, or (iii) both is the same identifier associated with the topic context instance, the executable action, or both; and responsive to determining the identifiers are the same, processing the message payload using the thread.

In some instances, the process 1200 further includes: receiving a message payload comprising: (i) a subsequent utterance or indication of an event, and (ii) application context, associated with an interaction between a user and an application; identifying an identifier associated with (i) the subsequent utterance or the indication of the interface action, (ii) the application context, or (iii) both; determining the identifier associated with (i) the subsequent utterance or the indication of the interface action, (ii) the application context, or (iii) both is different from an identifier associated with the topic context instance, the executable action, or both; and responsive to determining the identifiers are different, creating another thread having an identifier associated with (i) the subsequent utterance or the indication of the interface action, (ii) the application context, or (iii) both, wherein the another thread maintains (i) the subsequent utterance or the indication of the interface action, (ii) the application context, or (iii) both as a separate context for another distinct conversation between the user and the digital assistant; and processing the message payload using the another thread.

In some instances, the process 1200 further includes: responsive to determining the identifiers are different, sending a confirmation communication to the user requesting confirmation of (i) the subsequent utterance or the indication of the interface action, (ii) the application context, or (iii) both; and receiving, at the digital assistant, a confirmation utterance from the user that confirms (i) the subsequent utterance or the indication of the interface action, (ii) the application context, or (iii) both, wherein responsive to determining the identifiers are different and receipt of the confirmation utterance, creating the another thread.

EMBODIMENTS (A) a computer-implemented method includes: receiving, at a digital assistant, a natural language utterance from a user during a session between the user and the digital assistant; obtaining a topic context instance for the natural language utterance; generating, by a generative artificial intelligence (GenAI) model, a list comprising an executable action based on one or more candidate actions associated with the topic context instance; executing the executable action to produce an output, wherein the executing comprises: determining there is no thread running within the session that is associated with the topic context instance, the executable action, or both, responsive to determining there is no thread running, creating a thread associated with the topic context instance, the executable action, or both, wherein the thread maintains the topic context instance, the executable action, or both as a separate context from that of context associated with any other conversations for a distinct conversation comprising the natural language utterance between the user and the digital assistant, and executing, using the thread, the executable action to obtain the output; and sending the output or a communication derived from the output to the user.

(B) the computer-implemented method of embodiment (A) further includes: receiving, at the digital assistant, a subsequent natural language utterance from the user during the session between the user and the digital assistant; obtaining the topic context instance for the natural language utterance; generating, by the GenAI model, another list comprising another executable action based on one or more candidate actions associated with the topic context instance; executing the another executable action, wherein the executing comprises: identifying the thread running within the session is associated with the topic context instance, the executable action, or both, determining the another executable action should be executed using the thread based on an identifier associated with the topic context instance, the executable action, or both, and executing, using the thread, the another executable action to obtain another output; and sending the another output or a communication derived from the another output to the user.

(C) the computer-implemented method of embodiment (A) further includes: receiving, at the digital assistant, a subsequent natural language utterance from the user during the session between the user and the digital assistant; obtaining a topic context instance for the subsequent natural language; generating, by the GenAI model, another list comprising another executable action based on one or more candidate actions associated with the topic context instance for the subsequent natural language utterance; executing the another executable action, wherein the executing comprises: identifying the thread running within the session is associated with the topic context instance for the natural language utterance, the executable action, or both, determining there is no thread running within the session that is associated with the topic context instance for the subsequent natural language utterance, the another executable action, or both, responsive to determining there is no thread running within the session that is associated with the topic context instance for the subsequent natural language utterance, creating another thread having an identifier associated with the topic context instance for the subsequent natural language utterance, the another executable action, or both, wherein the another thread maintains the topic context instance for the subsequent natural language utterance, the another executable action, or both as a separate context for another distinct conversation between the user and the digital assistant, and executing, using the another thread, the another executable action to obtain another output; and sending the another output or a communication derived from the another output to the user.

(D) the computer-implemented method of embodiment (C): responsive to identifying the thread running within the session is associated with the topic context instance for the natural language utterance, the executable action, or both and determining there is no thread running within the session that is associated with the topic context instance for the subsequent natural language utterance, sending a confirmation communication to the user requesting confirmation of the subsequent natural language utterance, the topic context instance for the subsequent natural language utterance, or both; and receiving, at the digital assistant, a confirmation utterance from the user that confirms the subsequent natural language utterance, the topic context instance for the subsequent natural language utterance, or both, wherein responsive to determining there is no thread running within the session that is associated with the topic context instance for the subsequent natural language utterance and receipt of the confirmation utterance, creating the another thread.

(E) the computer-implemented method of embodiment (A) further includes receiving a message payload comprising: (i) a subsequent utterance or indication of an event, and (ii) application context, associated with an interaction between a user and an application; identifying an identifier associated with the subsequent utterance or the indication of the interface action, (ii) the application context, or (iii) both; determining the identifier associated with the subsequent utterance or the indication of the interface action, (ii) the application context, or (iii) both is the same identifier associated with the topic context instance, the executable action, or both; and responsive to determining the identifiers are the same, processing the message payload using the thread.

(F) the computer-implemented method of embodiment (A) further includes: receiving a message payload comprising: (i) a subsequent utterance or indication of an event, and (ii) application context, associated with an interaction between a user and an application; identifying an identifier associated with (i) the subsequent utterance or the indication of the interface action, (ii) the application context, or (iii) both; determining the identifier associated with (i) the subsequent utterance or the indication of the interface action, (ii) the application context, or (iii) both is different from an identifier associated with the topic context instance, the executable action, or both; and responsive to determining the identifiers are different, creating another thread having an identifier associated with (i) the subsequent utterance or the indication of the interface action, (ii) the application context, or (iii) both, wherein the another thread maintains (i) the subsequent utterance or the indication of the interface action, (ii) the application context, or (iii) both as a separate context for another distinct conversation between the user and the digital assistant; and processing the message payload using the another thread.

(G) the computer-implemented method of embodiment (F) further includes: responsive to determining the identifiers are different, sending a confirmation communication to the user requesting confirmation of (i) the subsequent utterance or the indication of the interface action, (ii) the application context, or (iii) both; and receiving, at the digital assistant, a confirmation utterance from the user that confirms (i) the subsequent utterance or the indication of the interface action, (ii) the application context, or (iii) both, wherein responsive to determining the identifiers are different and receipt of the confirmation utterance, creating the another thread.

(H) a system comprises: one or more processors; and one or more computer-readable media storing instructions which, when executed by the one or more processors, cause the system to perform operations including: receiving, at a digital assistant, a natural language utterance from a user during a session between the user and the digital assistant; obtaining a topic context instance for the natural language utterance; generating, by a generative artificial intelligence (GenAI) model, a list comprising an executable action based on one or more candidate actions associated with the topic context instance; executing the executable action to produce an output, wherein the executing comprises: determining there is no thread running within the session that is associated with the topic context instance, the executable action, or both, responsive to determining there is no thread running, creating a thread associated with the topic context instance, the executable action, or both, wherein the thread maintains the topic context instance, the executable action, or both as a separate context from that of context associated with any other conversations for a distinct conversation comprising the natural language utterance between the user and the digital assistant, and executing, using the thread, the executable action to obtain the output; and sending the output or a communication derived from the output to the user.

(I) the operations of embodiment (H) further include: receiving, at the digital assistant, a subsequent natural language utterance from the user during the session between the user and the digital assistant; obtaining the topic context instance for the natural language utterance; generating, by the GenAI model, another list comprising another executable action based on one or more candidate actions associated with the topic context instance; executing the another executable action, wherein the executing comprises: identifying the thread running within the session is associated with the topic context instance, the executable action, or both, determining the another executable action should be executed using the thread based on an identifier associated with the topic context instance, the executable action, or both, and executing, using the thread, the another executable action to obtain another output; and sending the another output or a communication derived from the another output to the user.

(J) the operations of embodiment (H) further include: receiving, at the digital assistant, a subsequent natural language utterance from the user during the session between the user and the digital assistant; obtaining a topic context instance for the subsequent natural language; generating, by the GenAI model, another list comprising another executable action based on one or more candidate actions associated with the topic context instance for the subsequent natural language utterance; executing the another executable action, wherein the executing comprises: identifying the thread running within the session is associated with the topic context instance for the natural language utterance, the executable action, or both, determining there is no thread running within the session that is associated with the topic context instance for the subsequent natural language utterance, the another executable action, or both, responsive to determining there is no thread running within the session that is associated with the topic context instance for the subsequent natural language utterance, creating another thread having an identifier associated with the topic context instance for the subsequent natural language utterance, the another executable action, or both, wherein the another thread maintains the topic context instance for the subsequent natural language utterance, the another executable action, or both as a separate context for another distinct conversation between the user and the digital assistant, and executing, using the another thread, the another executable action to obtain another output; and sending the another output or a communication derived from the another output to the user.

(K) the operations of embodiment (J) further include: responsive to identifying the thread running within the session is associated with the topic context instance for the natural language utterance, the executable action, or both and determining there is no thread running within the session that is associated with the topic context instance for the subsequent natural language utterance, sending a confirmation communication to the user requesting confirmation of the subsequent natural language utterance, the topic context instance for the subsequent natural language utterance, or both; and receiving, at the digital assistant, a confirmation utterance from the user that confirms the subsequent natural language utterance, the topic context instance for the subsequent natural language utterance, or both, wherein responsive to determining there is no thread running within the session that is associated with the topic context instance for the subsequent natural language utterance and receipt of the confirmation utterance, creating the another thread.

(L) the operations of embodiment (H) further include receiving a message payload comprising: (i) a subsequent utterance or indication of an event, and (ii) application context, associated with an interaction between a user and an application; identifying an identifier associated with the subsequent utterance or the indication of the interface action, (ii) the application context, or (iii) both; determining the identifier associated with the subsequent utterance or the indication of the interface action, (ii) the application context, or (iii) both is the same identifier associated with the topic context instance, the executable action, or both; and responsive to determining the identifiers are the same, processing the message payload using the thread.

(M) the operations of embodiment (H) further include: receiving a message payload comprising: (i) a subsequent utterance or indication of an event, and (ii) application context, associated with an interaction between a user and an application; identifying an identifier associated with (i) the subsequent utterance or the indication of the interface action, (ii) the application context, or (iii) both; determining the identifier associated with (i) the subsequent utterance or the indication of the interface action, (ii) the application context, or (iii) both is different from an identifier associated with the topic context instance, the executable action, or both; and responsive to determining the identifiers are different, creating another thread having an identifier associated with (i) the subsequent utterance or the indication of the interface action, (ii) the application context, or (iii) both, wherein the another thread maintains (i) the subsequent utterance or the indication of the interface action, (ii) the application context, or (iii) both as a separate context for another distinct conversation between the user and the digital assistant; and processing the message payload using the another thread.

(N) the operations of embodiment (M) further include: responsive to determining the identifiers are different, sending a confirmation communication to the user requesting confirmation of (i) the subsequent utterance or the indication of the interface action, (ii) the application context, or (iii) both; and receiving, at the digital assistant, a confirmation utterance from the user that confirms (i) the subsequent utterance or the indication of the interface action, (ii) the application context, or (iii) both, wherein responsive to determining the identifiers are different and receipt of the confirmation utterance, creating the another thread.

(O) one or more non-transitory computer-readable media storing instructions which, when executed by one or more processors, cause the one or more processors to perform operations including: receiving, at a digital assistant, a natural language utterance from a user during a session between the user and the digital assistant; obtaining a topic context instance for the natural language utterance; generating, by a generative artificial intelligence (GenAI) model, a list comprising an executable action based on one or more candidate actions associated with the topic context instance; executing the executable action to produce an output, wherein the executing comprises: determining there is no thread running within the session that is associated with the topic context instance, the executable action, or both, responsive to determining there is no thread running, creating a thread associated with the topic context instance, the executable action, or both, wherein the thread maintains the topic context instance, the executable action, or both as a separate context from that of context associated with any other conversations for a distinct conversation comprising the natural language utterance between the user and the digital assistant, and executing, using the thread, the executable action to obtain the output; and sending the output or a communication derived from the output to the user.

(P) the operations of embodiment (O) further include: receiving, at the digital assistant, a subsequent natural language utterance from the user during the session between the user and the digital assistant; obtaining the topic context instance for the natural language utterance; generating, by the GenAI model, another list comprising another executable action based on one or more candidate actions associated with the topic context instance; executing the another executable action, wherein the executing comprises: identifying the thread running within the session is associated with the topic context instance, the executable action, or both, determining the another executable action should be executed using the thread based on an identifier associated with the topic context instance, the executable action, or both, and executing, using the thread, the another executable action to obtain another output; and sending the another output or a communication derived from the another output to the user.

(Q) the operations of embodiment (O) further include: receiving, at the digital assistant, a subsequent natural language utterance from the user during the session between the user and the digital assistant; obtaining a topic context instance for the subsequent natural language; generating, by the GenAI model, another list comprising another executable action based on one or more candidate actions associated with the topic context instance for the subsequent natural language utterance; executing the another executable action, wherein the executing comprises: identifying the thread running within the session is associated with the topic context instance for the natural language utterance, the executable action, or both, determining there is no thread running within the session that is associated with the topic context instance for the subsequent natural language utterance, the another executable action, or both, responsive to determining there is no thread running within the session that is associated with the topic context instance for the subsequent natural language utterance, creating another thread having an identifier associated with the topic context instance for the subsequent natural language utterance, the another executable action, or both, wherein the another thread maintains the topic context instance for the subsequent natural language utterance, the another executable action, or both as a separate context for another distinct conversation between the user and the digital assistant, and executing, using the another thread, the another executable action to obtain another output; and sending the another output or a communication derived from the another output to the user.

(R) the operations of embodiment (Q) further include: responsive to identifying the thread running within the session is associated with the topic context instance for the natural language utterance, the executable action, or both and determining there is no thread running within the session that is associated with the topic context instance for the subsequent natural language utterance, sending a confirmation communication to the user requesting confirmation of the subsequent natural language utterance, the topic context instance for the subsequent natural language utterance, or both; and receiving, at the digital assistant, a confirmation utterance from the user that confirms the subsequent natural language utterance, the topic context instance for the subsequent natural language utterance, or both, wherein responsive to determining there is no thread running within the session that is associated with the topic context instance for the subsequent natural language utterance and receipt of the confirmation utterance, creating the another thread.

(S) the operations of embodiment (O) further include receiving a message payload comprising: (i) a subsequent utterance or indication of an event, and (ii) application context, associated with an interaction between a user and an application; identifying an identifier associated with the subsequent utterance or the indication of the interface action, (ii) the application context, or (iii) both; determining the identifier associated with the subsequent utterance or the indication of the interface action, (ii) the application context, or (iii) both is the same identifier associated with the topic context instance, the executable action, or both; and responsive to determining the identifiers are the same, processing the message payload using the thread.

(T) the operations of embodiment (O) further include: receiving a message payload comprising: (i) a subsequent utterance or indication of an event, and (ii) application context, associated with an interaction between a user and an application; identifying an identifier associated with (i) the subsequent utterance or the indication of the interface action, (ii) the application context, or (iii) both; determining the identifier associated with (i) the subsequent utterance or the indication of the interface action, (ii) the application context, or (iii) both is different from an identifier associated with the topic context instance, the executable action, or both; and responsive to determining the identifiers are different, creating another thread having an identifier associated with (i) the subsequent utterance or the indication of the interface action, (ii) the application context, or (iii) both, wherein the another thread maintains (i) the subsequent utterance or the indication of the interface action, (ii) the application context, or (iii) both as a separate context for another distinct conversation between the user and the digital assistant; and processing the message payload using the another thread.

(U) the operations of embodiment (T) the operations further include: responsive to determining the identifiers are different, sending a confirmation communication to the user requesting confirmation of (i) the subsequent utterance or the indication of the interface action, (ii) the application context, or (iii) both; and receiving, at the digital assistant, a confirmation utterance from the user that confirms (i) the subsequent utterance or the indication of the interface action, (ii) the application context, or (iii) both, wherein responsive to determining the identifiers are different and receipt of the confirmation utterance, creating the another thread.

Illustrative Systems

As noted above, infrastructure as a service (IaaS) is one particular type of cloud computing. IaaS can be configured to provide virtualized computing resources over a public network (e.g., the Internet). In an IaaS model, a cloud computing provider can host the infrastructure components (e.g., servers, storage devices, network nodes (e.g., hardware), deployment software, platform virtualization (e.g., a hypervisor layer), or the like). In some cases, an IaaS provider may also supply a variety of services to accompany those infrastructure components (example services include billing software, monitoring software, logging software, load balancing software, clustering software, etc.). Thus, as these services may be policy-driven, IaaS users may be able to implement policies to drive load balancing to maintain application availability and performance.

In some instances, IaaS customers may access resources and services through a wide area network (WAN), such as the Internet, and can use the cloud provider's services to install the remaining elements of an application stack. For example, the user can log in to the IaaS platform to create virtual machines (VMs), install operating systems (OSs) on each VM, deploy middleware such as databases, create storage buckets for workloads and backups, and even install enterprise software into that VM. Customers can then use the provider's services to perform various functions, including balancing network traffic, troubleshooting application issues, monitoring performance, managing disaster recovery, etc.

In most cases, a cloud computing model will require the participation of a cloud provider. The cloud provider may, but need not be, a third-party service that specializes in providing (e.g., offering, renting, selling) IaaS. An entity might also opt to deploy a private cloud, becoming its own provider of infrastructure services.

In some examples, IaaS deployment is the process of putting a new application, or a new version of an application, onto a prepared application server or the like. It may also include the process of preparing the server (e.g., installing libraries, daemons, etc.). This is often managed by the cloud provider, below the hypervisor layer (e.g., the servers, storage, network hardware, and virtualization). Thus, the customer may be responsible for handling (OS), middleware, and/or application deployment (e.g., on self-service virtual machines (e.g., that can be spun up on demand)) or the like.

In some examples, IaaS provisioning may refer to acquiring computers or virtual hosts for use, and even installing needed libraries or services on them. In most cases, deployment does not include provisioning, and the provisioning may need to be performed first.

In some cases, there are two different challenges for IaaS provisioning. First, there is the initial challenge of provisioning the initial set of infrastructure before anything is running. Second, there is the challenge of evolving the existing infrastructure (e.g., adding new services, changing services, removing services, etc.) once everything has been provisioned. In some cases, these two challenges may be addressed by enabling the configuration of the infrastructure to be defined declaratively. In other words, the infrastructure (e.g., what components are needed and how they interact) can be defined by one or more configuration files. Thus, the overall topology of the infrastructure (e.g., what resources depend on which, and how they each work together) can be described declaratively. In some instances, once the topology is defined, a workflow can be generated that creates and/or manages the different components described in the configuration files.

In some examples, an infrastructure may have many interconnected elements. For example, there may be one or more virtual private clouds (VPCs) (e.g., a potentially on-demand pool of configurable and/or shared computing resources), also known as a core network. In some examples, there may also be one or more inbound/outbound traffic group rules provisioned to define how the inbound and/or outbound traffic of the network will be set up and one or more virtual machines (VMs). Other infrastructure elements may also be provisioned, such as a load balancer, a database, or the like. As more and more infrastructure elements are desired and/or added, the infrastructure may incrementally evolve.

In some instances, continuous deployment techniques may be employed to enable deployment of infrastructure code across various virtual computing environments. Additionally, the described techniques can enable infrastructure management within these environments. In some examples, service teams can write code that is desired to be deployed to one or more, but often many, different production environments (e.g., across various different geographic locations, sometimes spanning the entire world). However, in some examples, the infrastructure on which the code will be deployed must first be set up. In some instances, the provisioning can be done manually, a provisioning tool may be utilized to provision the resources, and/or deployment tools may be utilized to deploy the code once the infrastructure is provisioned.

Figure 13:
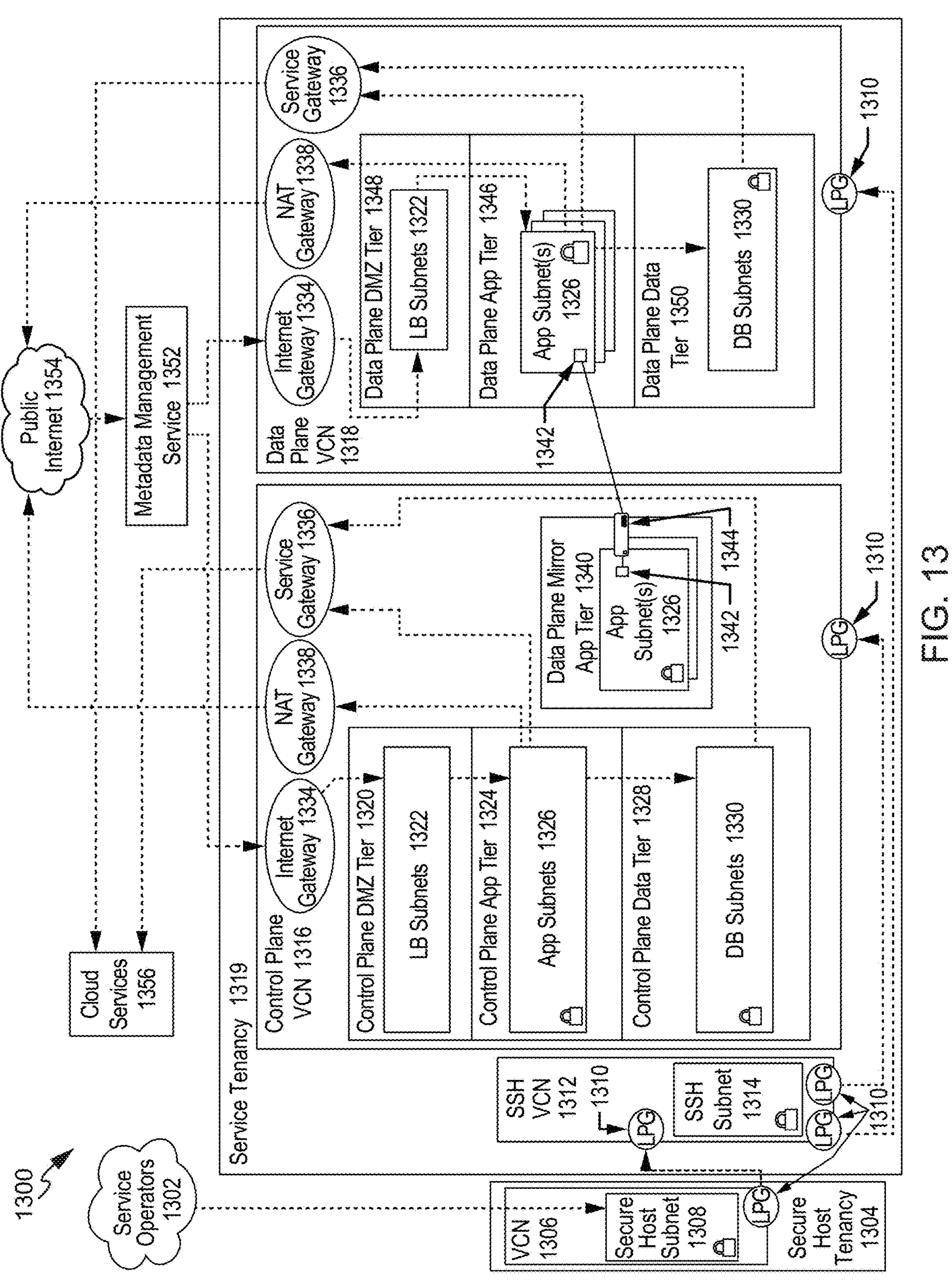
FIG. 13 is a block diagram illustrating one pattern for implementing a cloud infrastructure as a service system, according to at least one embodiment.

FIG. 13 is a block diagram 1300 illustrating an example pattern of an IaaS architecture, according to at least one embodiment. Service operators 1302 can be communicatively coupled to a secure host tenancy 1304 that can include a virtual cloud network (VCN) 1306 and a secure host subnet 1308. In some examples, the service operators 1302 may be using one or more client computing devices, which may be portable handheld devices (e.g., an iPhone®, cellular telephone, an iPad®, computing tablet, a personal digital assistant (PDA)) or wearable devices (e.g., a Google Glass® head mounted display), running software such as Microsoft Windows Mobile®, and/or a variety of mobile operating systems such as iOS, Windows Phone, Android, BlackBerry 8, Palm OS, and the like, and being Internet, e-mail, short message service (SMS), Blackberry®, or other communication protocol enabled. Alternatively, the client computing devices can be general purpose personal computers including, by way of example, personal computers and/or laptop computers running various versions of Microsoft Windows®, Apple Macintosh®, and/or Linux operating systems. The client computing devices can be workstation computers running any of a variety of commercially-available UNIX® or UNIX-like operating systems, including without limitation the variety of GNU/Linux operating systems, such as for example, Google Chrome OS. Alternatively, or in addition, client computing devices may be any other electronic device, such as a thin-client computer, an Internet-enabled gaming system (e.g., a Microsoft Xbox gaming console with or without a Kinect® gesture input device), and/or a personal messaging device, capable of communicating over a network that can access the VCN 1306 and/or the Internet.

The VCN 1306 can include a local peering gateway (LPG) 1310 that can be communicatively coupled to a secure shell (SSH) VCN 1312 via an LPG 1310 contained in the SSH VCN 1312. The SSH VCN 1312 can include an SSH subnet 1314, and the SSH VCN 1312 can be communicatively coupled to a control plane VCN 1316 via the LPG 1310 contained in the control plane VCN 1316. Also, the SSH VCN 1312 can be communicatively coupled to a data plane VCN 1318 via an LPG 1310. The control plane VCN 1316 and the data plane VCN 1318 can be contained in a service tenancy 1319 that can be owned and/or operated by the IaaS provider.

The control plane VCN 1316 can include a control plane demilitarized zone (DMZ) tier 1320 that acts as a perimeter network (e.g., portions of a corporate network between the corporate intranet and external networks). The DMZ-based servers may have restricted responsibilities and help keep breaches contained. Additionally, the DMZ tier 1320 can include one or more load balancer (LB) subnet(s) 1322, a control plane app tier 1324 that can include app subnet(s) 1326, a control plane data tier 1328 that can include database (DB) subnet(s) 1330 (e.g., frontend DB subnet(s) and/or backend DB subnet(s)). The LB subnet(s) 1322 contained in the control plane DMZ tier 1320 can be communicatively coupled to the app subnet(s) 1326 contained in the control plane app tier 1324 and an Internet gateway 1334 that can be contained in the control plane VCN 1316, and the app subnet(s) 1326 can be communicatively coupled to the DB subnet(s) 1330 contained in the control plane data tier 1328 and a service gateway 1336 and a network address translation (NAT) gateway 1338. The control plane VCN 1316 can include the service gateway 1336 and the NAT gateway 1338.

The control plane VCN 1316 can include a data plane mirror app tier 1340 that can include app subnet(s) 1326. The app subnet(s) 1326 contained in the data plane mirror app tier 1340 can include a virtual network interface controller (VNIC) 1342 that can execute a compute instance 1344. The compute instance 1344 can communicatively couple the app subnet(s) 1326 of the data plane mirror app tier 1340 to app subnet(s) 1326 that can be contained in a data plane app tier 1346.

The data plane VCN 1318 can include the data plane app tier 1346, a data plane DMZ tier 1348, and a data plane data tier 1350. The data plane DMZ tier 1348 can include LB subnet(s) 1322 that can be communicatively coupled to the app subnet(s) 1326 of the data plane app tier 1346 and the Internet gateway 1334 of the data plane VCN 1318. The app subnet(s) 1326 can be communicatively coupled to the service gateway 1336 of the data plane VCN 1318 and the NAT gateway 1338 of the data plane VCN 1318. The data plane data tier 1350 can also include the DB subnet(s) 1330 that can be communicatively coupled to the app subnet(s) 1326 of the data plane app tier 1346.

The Internet gateway 1334 of the control plane VCN 1316 and of the data plane VCN 1318 can be communicatively coupled to a metadata management service 1352 that can be communicatively coupled to public Internet 1354. Public Internet 1354 can be communicatively coupled to the NAT gateway 1338 of the control plane VCN 1316 and of the data plane VCN 1318. The service gateway 1336 of the control plane VCN 1316 and of the data plane VCN 1318 can be communicatively coupled to cloud services 1356.

In some examples, the service gateway 1336 of the control plane VCN 1316 or of the data plane VCN 1318 can make application programming interface (API) calls to cloud services 1356 without going through public Internet 1354. The API calls to cloud services 1356 from the service gateway 1336 can be one-way: the service gateway 1336 can make API calls to cloud services 1356, and cloud services 1356 can send requested data to the service gateway 1336. But, cloud services 1356 may not initiate API calls to the service gateway 1336.

In some examples, the secure host tenancy 1304 can be directly connected to the service tenancy 1319, which may be otherwise isolated. The secure host subnet 1308 can communicate with the SSH subnet 1314 through an LPG 1310 that may enable two-way communication over an otherwise isolated system. Connecting the secure host subnet 1308 to the SSH subnet 1314 may give the secure host subnet 1308 access to other entities within the service tenancy 1319.

The control plane VCN 1316 may allow users of the service tenancy 1319 to set up or otherwise provision desired resources. Desired resources provisioned in the control plane VCN 1316 may be deployed or otherwise used in the data plane VCN 1318. In some examples, the control plane VCN 1316 can be isolated from the data plane VCN 1318, and the data plane mirror app tier 1340 of the control plane VCN 1316 can communicate with the data plane app tier 1346 of the data plane VCN 1318 via VNICs 1342 that can be contained in the data plane mirror app tier 1340 and the data plane app tier 1346.

In some examples, users of the system, or customers, can make requests, for example create, read, update, or delete (CRUD) operations, through public Internet 1354 that can communicate the requests to the metadata management service 1352. The metadata management service 1352 can communicate the request to the control plane VCN 1316 through the Internet gateway 1334. The request can be received by the LB subnet(s) 1322 contained in the control plane DMZ tier 1320. The LB subnet(s) 1322 may determine that the request is valid, and in response to this determination, the LB subnet(s) 1322 can transmit the request to app subnet(s) 1326 contained in the control plane app tier 1324. If the request is validated and requires a call to public Internet 1354, the call to public Internet 1354 may be transmitted to the NAT gateway 1338 that can make the call to public Internet 1354. Metadata that may be desired to be stored by the request can be stored in the DB subnet(s) 1330.

In some examples, the data plane mirror app tier 1340 can facilitate direct communication between the control plane VCN 1316 and the data plane VCN 1318. For example, changes, updates, or other suitable modifications to configuration may be desired to be applied to the resources contained in the data plane VCN 1318. Via a VNIC 1342, the control plane VCN 1316 can directly communicate with, and can thereby execute the changes, updates, or other suitable modifications to configuration to, resources contained in the data plane VCN 1318.

In some embodiments, the control plane VCN 1316 and the data plane VCN 1318 can be contained in the service tenancy 1319. In this case, the user, or the customer, of the system may not own or operate either the control plane VCN 1316 or the data plane VCN 1318. Instead, the IaaS provider may own or operate the control plane VCN 1316 and the data plane VCN 1318, both of which may be contained in the service tenancy 1319. This embodiment can enable isolation of networks that may prevent users or customers from interacting with other users', or other customers', resources. Also, this embodiment may allow users or customers of the system to store databases privately without needing to rely on public Internet 1354, which may not have a desired level of threat prevention, for storage.

In other embodiments, the LB subnet(s) 1322 contained in the control plane VCN 1316 can be configured to receive a signal from the service gateway 1336. In this embodiment, the control plane VCN 1316 and the data plane VCN 1318 may be configured to be called by a customer of the IaaS provider without calling public Internet 1354. Customers of the IaaS provider may desire this embodiment since database(s) that the customers use may be controlled by the IaaS provider and may be stored on the service tenancy 1319, which may be isolated from public Internet 1354.

Figure 14:
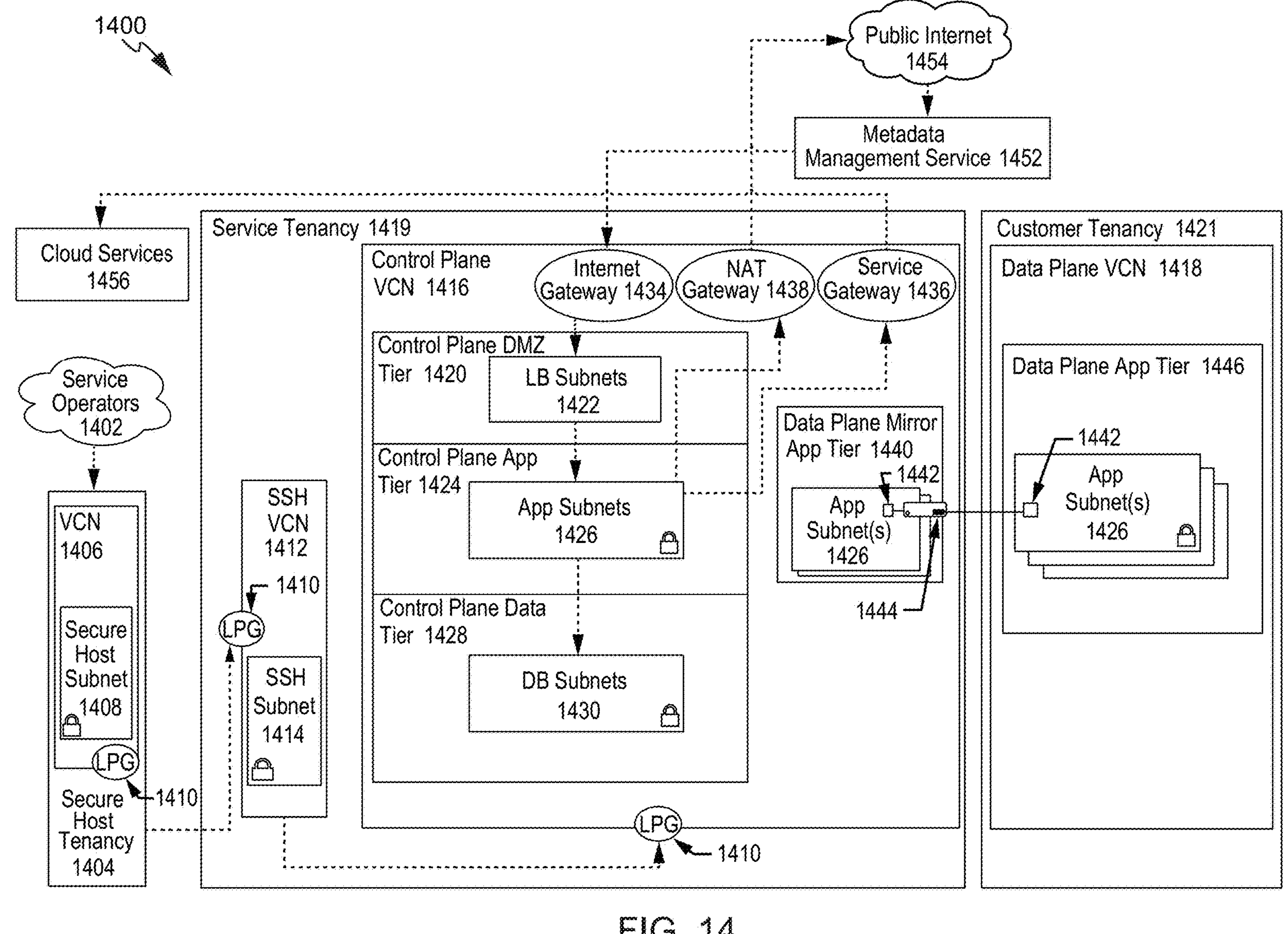
FIG. 14 is a block diagram illustrating another pattern for implementing a cloud infrastructure as a service system, according to at least one embodiment.

FIG. 14 is a block diagram 1400 illustrating another example pattern of an IaaS architecture, according to at least one embodiment. Service operators 1402 (e.g., service operators 1302 of FIG. 13) can be communicatively coupled to a secure host tenancy 1404 (e.g., the secure host tenancy 1304 of FIG. 13) that can include a virtual cloud network (VCN) 1406 (e.g., the VCN 1306 of FIG. 13) and a secure host subnet 1408 (e.g., the secure host subnet 1308 of FIG. 13). The VCN 1406 can include a local peering gateway (LPG) 1410 (e.g., the LPG 1310 of FIG. 13) that can be communicatively coupled to a secure shell (SSH) VCN 1412 (e.g., the SSH VCN 1312 of FIG. 13) via an LPG 1310 contained in the SSH VCN 1412. The SSH VCN 1412 can include an SSH subnet 1414 (e.g., the SSH subnet 1314 of FIG. 13), and the SSH VCN 1412 can be communicatively coupled to a control plane VCN 1416 (e.g., the control plane VCN 1316 of FIG. 13) via an LPG 1410 contained in the control plane VCN 1416. The control plane VCN 1416 can be contained in a service tenancy 1419 (e.g., the service tenancy 1319 of FIG. 13), and the data plane VCN 1418 (e.g., the data plane VCN 1318 of FIG. 13) can be contained in a customer tenancy 1421 that may be owned or operated by users, or customers, of the system.

The control plane VCN 1416 can include a control plane DMZ tier 1420 (e.g., the control plane DMZ tier 1320 of FIG. 13) that can include LB subnet(s) 1422 (e.g., LB subnet(s) 1322 of FIG. 13), a control plane app tier 1424 (e.g., the control plane app tier 1324 of FIG. 13) that can include app subnet(s) 1426 (e.g., app subnet(s) 1326 of FIG. 13), a control plane data tier 1428 (e.g., the control plane data tier 1328 of FIG. 13) that can include database (DB) subnet(s) 1430 (e.g., similar to DB subnet(s) 1330 of FIG. 13). The LB subnet(s) 1422 contained in the control plane DMZ tier 1420 can be communicatively coupled to the app subnet(s) 1426 contained in the control plane app tier 1424 and an Internet gateway 1434 (e.g., the Internet gateway 1334 of FIG. 13) that can be contained in the control plane VCN 1416, and the app subnet(s) 1426 can be communicatively coupled to the DB subnet(s) 1430 contained in the control plane data tier 1428 and a service gateway 1436 (e.g., the service gateway 1336 of FIG. 13) and a network address translation (NAT) gateway 1438 (e.g., the NAT gateway 1338 of FIG. 13). The control plane VCN 1416 can include the service gateway 1436 and the NAT gateway 1438.

The control plane VCN 1416 can include a data plane mirror app tier 1440 (e.g., the data plane mirror app tier 1340 of FIG. 13) that can include app subnet(s) 1426. The app subnet(s) 1426 contained in the data plane mirror app tier 1440 can include a virtual network interface controller (VNIC) 1442 (e.g., the VNIC of 1342) that can execute a compute instance 1444 (e.g., similar to the compute instance 1344 of FIG. 13). The compute instance 1444 can facilitate communication between the app subnet(s) 1426 of the data plane mirror app tier 1440 and the app subnet(s) 1426 that can be contained in a data plane app tier 1446 (e.g., the data plane app tier 1346 of FIG. 13) via the VNIC 1442 contained in the data plane mirror app tier 1440 and the VNIC 1442 contained in the data plane app tier 1446.

The Internet gateway 1434 contained in the control plane VCN 1416 can be communicatively coupled to a metadata management service 1452 (e.g., the metadata management service 1352 of FIG. 13) that can be communicatively coupled to public Internet 1454 (e.g., public Internet 1354 of FIG. 13). Public Internet 1454 can be communicatively coupled to the NAT gateway 1438 contained in the control plane VCN 1416. The service gateway 1436 contained in the control plane VCN 1416 can be communicatively coupled to cloud services 1456 (e.g., cloud services 1356 of FIG. 13).

In some examples, the data plane VCN 1418 can be contained in the customer tenancy 1421. In this case, the IaaS provider may provide the control plane VCN 1416 for each customer, and the IaaS provider may, for each customer, set up a unique compute instance 1444 that is contained in the service tenancy 1419. Each compute instance 1444 may allow communication between the control plane VCN 1416, contained in the service tenancy 1419, and the data plane VCN 1418 that is contained in the customer tenancy 1421. The compute instance 1444 may allow resources, that are provisioned in the control plane VCN 1416 that is contained in the service tenancy 1419, to be deployed or otherwise used in the data plane VCN 1418 that is contained in the customer tenancy 1421.

In other examples, the customer of the IaaS provider may have databases that live in the customer tenancy 1421. In this example, the control plane VCN 1416 can include the data plane mirror app tier 1440 that can include app subnet(s) 1426. The data plane mirror app tier 1440 can reside in the data plane VCN 1418, but the data plane mirror app tier 1440 may not live in the data plane VCN 1418. That is, the data plane mirror app tier 1440 may have access to the customer tenancy 1421, but the data plane mirror app tier 1440 may not exist in the data plane VCN 1418 or be owned or operated by the customer of the IaaS provider. The data plane mirror app tier 1440 may be configured to make calls to the data plane VCN 1418 but may not be configured to make calls to any entity contained in the control plane VCN 1416. The customer may desire to deploy or otherwise use resources in the data plane VCN 1418 that are provisioned in the control plane VCN 1416, and the data plane mirror app tier 1440 can facilitate the desired deployment, or other usage of resources, of the customer.

In some embodiments, the customer of the IaaS provider can apply filters to the data plane VCN 1418. In this embodiment, the customer can determine what the data plane VCN 1418 can access, and the customer may restrict access to public Internet 1454 from the data plane VCN 1418. The IaaS provider may not be able to apply filters or otherwise control access of the data plane VCN 1418 to any outside networks or databases. Applying filters and controls by the customer onto the data plane VCN 1418, contained in the customer tenancy 1421, can help isolate the data plane VCN 1418 from other customers and from public Internet 1454.

In some embodiments, cloud services 1456 can be called by the service gateway 1436 to access services that may not exist on public Internet 1454, on the control plane VCN 1416, or on the data plane VCN 1418. The connection between cloud services 1456 and the control plane VCN 1416 or the data plane VCN 1418 may not be live or continuous. Cloud services 1456 may exist on a different network owned or operated by the IaaS provider. Cloud services 1456 may be configured to receive calls from the service gateway 1436 and may be configured to not receive calls from public Internet 1454. Some cloud services 1456 may be isolated from other cloud services 1456, and the control plane VCN 1416 may be isolated from cloud services 1456 that may not be in the same region as the control plane VCN 1416. For example, the control plane VCN 1416 may be located in "Region 1," and cloud service "Deployment 13," may be located in Region 1 and in "Region 2." If a call to Deployment 13 is made by the service gateway 1436 contained in the control plane VCN 1416 located in Region 1, the call may be transmitted to Deployment 13 in Region 1. In this example, the control plane VCN 1416, or Deployment 13 in Region 1, may not be communicatively coupled to, or otherwise in communication with, Deployment 13 in Region 2.

Figure 15:
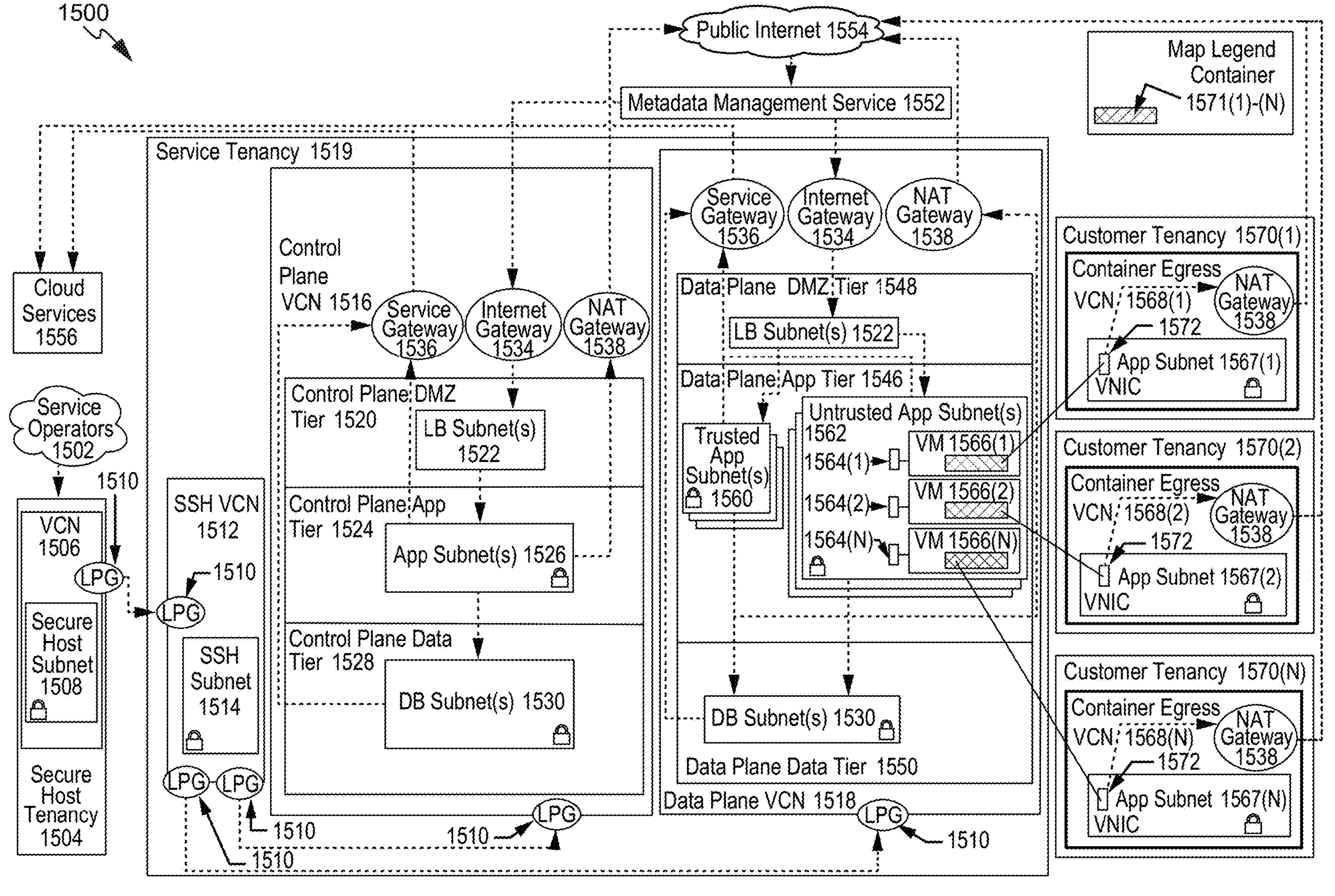
FIG. 15 is a block diagram illustrating another pattern for implementing a cloud infrastructure as a service system, according to at least one embodiment.

FIG. 15 is a block diagram 1500 illustrating another example pattern of an IaaS architecture, according to at least one embodiment. Service operators 1502 (e.g., service operators 1302 of FIG. 13) can be communicatively coupled to a secure host tenancy 1504 (e.g., the secure host tenancy 1304 of FIG. 13) that can include a virtual cloud network (VCN) 1506 (e.g., the VCN 1306 of FIG. 13) and a secure host subnet 1508 (e.g., the secure host subnet 1308 of FIG. 13). The VCN 1506 can include an LPG 1510 (e.g., the LPG 1310 of FIG. 13) that can be communicatively coupled to an SSH VCN 1512 (e.g., the SSH VCN 1312 of FIG. 13) via an LPG 1510 contained in the SSH VCN 1512. The SSH VCN 1512 can include an SSH subnet 1514 (e.g., the SSH subnet 1314 of FIG. 13), and the SSH VCN 1512 can be communicatively coupled to a control plane VCN 1516 (e.g., the control plane VCN 1316 of FIG. 13) via an LPG 1510 contained in the control plane VCN 1516 and to a data plane VCN 1518 (e.g., the data plane 1318 of FIG. 13) via an LPG 1510 contained in the data plane VCN 1518. The control plane VCN 1516 and the data plane VCN 1518 can be contained in a service tenancy 1519 (e.g., the service tenancy 1319 of FIG. 13).

The control plane VCN 1516 can include a control plane DMZ tier 1520 (e.g., the control plane DMZ tier 1320 of FIG. 13) that can include load balancer (LB) subnet(s) 1522 (e.g., LB subnet(s) 1322 of FIG. 13), a control plane app tier 1524 (e.g., the control plane app tier 1324 of FIG. 13) that can include app subnet(s) 1526 (e.g., similar to app subnet(s) 1326 of FIG. 13), a control plane data tier 1528 (e.g., the control plane data tier 1328 of FIG. 13) that can include DB subnet(s) 1530. The LB subnet(s) 1522 contained in the control plane DMZ tier 1520 can be communicatively coupled to the app subnet(s) 1526 contained in the control plane app tier 1524 and to an Internet gateway 1534 (e.g., the Internet gateway 1334 of FIG. 13) that can be contained in the control plane VCN 1516, and the app subnet(s) 1526 can be communicatively coupled to the DB subnet(s) 1530 contained in the control plane data tier 1528 and to a service gateway 1536 (e.g., the service gateway of FIG. 13) and a network address translation (NAT) gateway 1538 (e.g., the NAT gateway 1338 of FIG. 13). The control plane VCN 1516 can include the service gateway 1536 and the NAT gateway 1538.

The data plane VCN 1518 can include a data plane app tier 1546 (e.g., the data plane app tier 1346 of FIG. 13), a data plane DMZ tier 1548 (e.g., the data plane DMZ tier 1348 of FIG. 13), and a data plane data tier 1550 (e.g., the data plane data tier 1350 of FIG. 13). The data plane DMZ tier 1548 can include LB subnet(s) 1522 that can be communicatively coupled to trusted app subnet(s) 1560 and untrusted app subnet(s) 1562 of the data plane app tier 1546 and the Internet gateway 1534 contained in the data plane VCN 1518. The trusted app subnet(s) 1560 can be communicatively coupled to the service gateway 1536 contained in the data plane VCN 1518, the NAT gateway 1538 contained in the data plane VCN 1518, and DB subnet(s) 1530 contained in the data plane data tier 1550. The untrusted app subnet(s) 1562 can be communicatively coupled to the service gateway 1536 contained in the data plane VCN 1518 and DB subnet(s) 1530 contained in the data plane data tier 1550. The data plane data tier 1550 can include DB subnet(s) 1530 that can be communicatively coupled to the service gateway 1536 contained in the data plane VCN 1518.

The untrusted app subnet(s) 1562 can include one or more primary VNICs 1564(1)-(N) that can be communicatively coupled to tenant virtual machines (VMs) 1566(1)-(N). Each tenant VM 1566(1)-(N) can be communicatively coupled to a respective app subnet 1567(1)-(N) that can be contained in respective container egress VCNs 1568(1)-(N) that can be contained in respective customer tenancies 1570(1)-(N). Respective secondary VNICs 1572(1)-(N) can facilitate communication between the untrusted app subnet(s) 1562 contained in the data plane VCN 1518 and the app subnet contained in the container egress VCNs 1568(1)-(N). Each container egress VCNs 1568(1)-(N) can include a NAT gateway 1538 that can be communicatively coupled to public Internet 1554 (e.g., public Internet 1354 of FIG. 13).

The Internet gateway 1534 contained in the control plane VCN 1516 and contained in the data plane VCN 1518 can be communicatively coupled to a metadata management service 1552 (e.g., the metadata management system 1352 of FIG. 13) that can be communicatively coupled to public Internet 1554. Public Internet 1554 can be communicatively coupled to the NAT gateway 1538 contained in the control plane VCN 1516 and contained in the data plane VCN 1518. The service gateway 1536 contained in the control plane VCN 1516 and contained in the data plane VCN 1518 can be communicatively coupled to cloud services 1556.

In some embodiments, the data plane VCN 1518 can be integrated with customer tenancies 1570. This integration can be useful or desirable for customers of the IaaS provider in some cases such as a case that may desire support when executing code. The customer may provide code to run that may be destructive, may communicate with other customer resources, or may otherwise cause undesirable effects. In response to this, the IaaS provider may determine whether to run code given to the IaaS provider by the customer.

In some examples, the customer of the IaaS provider may grant temporary network access to the IaaS provider and request a function to be attached to the data plane app tier 1546. Code to run the function may be executed in the VMs 1566(1)-(N), and the code may not be configured to run anywhere else on the data plane VCN 1518. Each VM 1566(1)-(N) may be connected to one customer tenancy 1570. Respective containers 1571(1)-(N) contained in the VMs 1566(1)-(N) may be configured to run the code. In this case, there can be a dual isolation (e.g., the containers 1571(1)-(N) running code, where the containers 1571(1)-(N) may be contained in at least the VM 1566(1)-(N) that are contained in the untrusted app subnet(s) 1562), which may help prevent incorrect or otherwise undesirable code from damaging the network of the IaaS provider or from damaging a network of a different customer. The containers 1571(1)-(N) may be communicatively coupled to the customer tenancy 1570 and may be configured to transmit or receive data from the customer tenancy 1570. The containers 1571(1)-(N) may not be configured to transmit or receive data from any other entity in the data plane VCN 1518. Upon completion of running the code, the IaaS provider may kill or otherwise dispose of the containers 1571(1)-(N).

In some embodiments, the trusted app subnet(s) 1560 may run code that may be owned or operated by the IaaS provider. In this embodiment, the trusted app subnet(s) 1560 may be communicatively coupled to the DB subnet(s) 1530 and be configured to execute CRUD operations in the DB subnet(s) 1530. The untrusted app subnet(s) 1562 may be communicatively coupled to the DB subnet(s) 1530, but in this embodiment, the untrusted app subnet(s) may be configured to execute read operations in the DB subnet(s) 1530. The containers 1571(1)-(N) that can be contained in the VM 1566(1)-(N) of each customer and that may run code from the customer may not be communicatively coupled with the DB subnet(s) 1530.

In other embodiments, the control plane VCN 1516 and the data plane VCN 1518 may not be directly communicatively coupled. In this embodiment, there may be no direct communication between the control plane VCN 1516 and the data plane VCN 1518. However, communication can occur indirectly through at least one method. An LPG 1510 may be established by the IaaS provider that can facilitate communication between the control plane VCN 1516 and the data plane VCN 1518. In another example, the control plane VCN 1516 or the data plane VCN 1518 can make a call to cloud services 1556 via the service gateway 1536. For example, a call to cloud services 1556 from the control plane VCN 1516 can include a request for a service that can communicate with the data plane VCN 1518.

Figure 16:
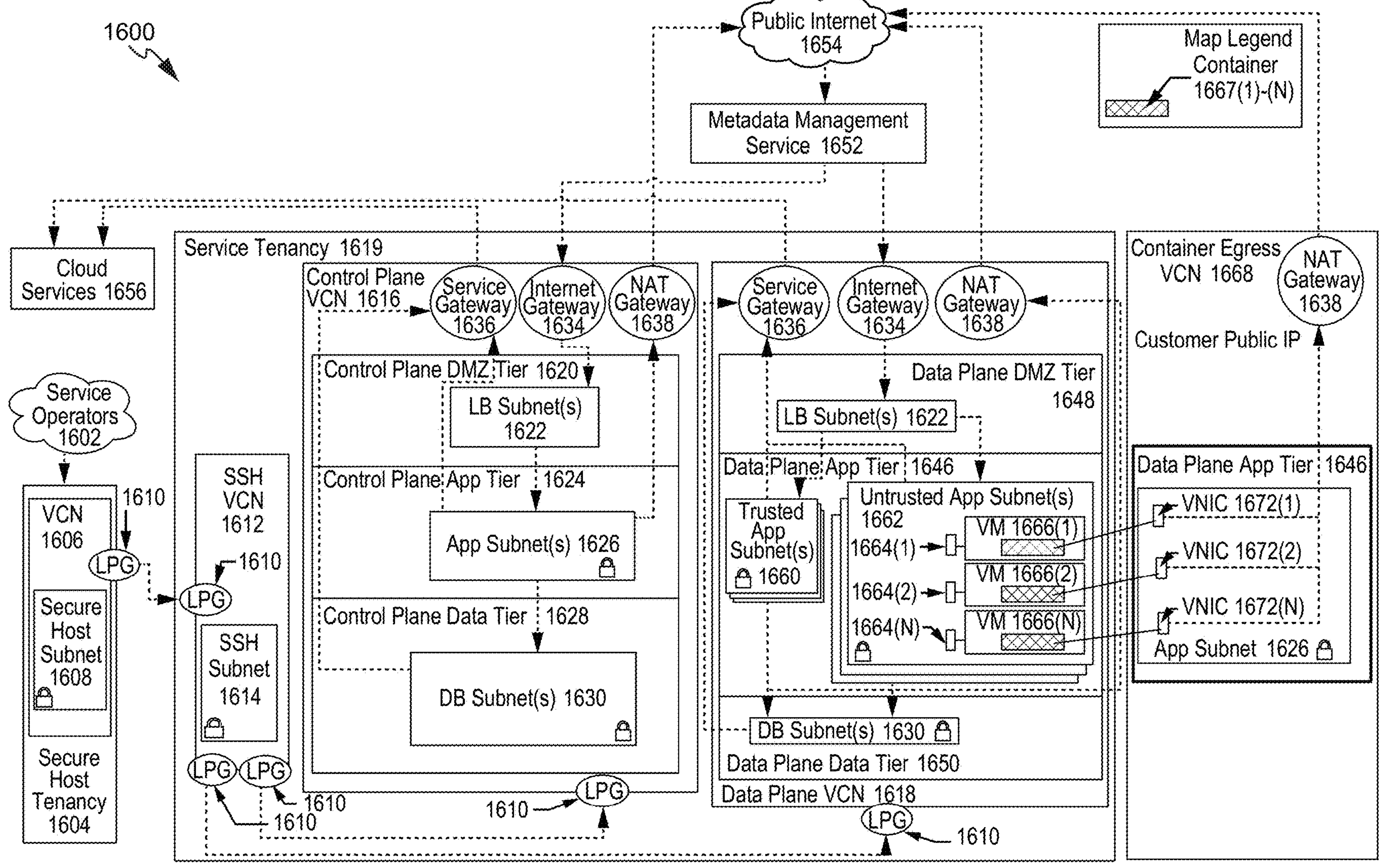
FIG. 16 is a block diagram illustrating another pattern for implementing a cloud infrastructure as a service system, according to at least one embodiment.

FIG. 16 is a block diagram 1600 illustrating another example pattern of an IaaS architecture, according to at least one embodiment. Service operators 1602 (e.g., service operators 1302 of FIG. 13) can be communicatively coupled to a secure host tenancy 1604 (e.g., the secure host tenancy 1304 of FIG. 13) that can include a virtual cloud network (VCN) 1606 (e.g., the VCN 1306 of FIG. 13) and a secure host subnet 1608 (e.g., the secure host subnet 1308 of FIG. 13). The VCN 1606 can include an LPG 1610 (e.g., the LPG 1310 of FIG. 13) that can be communicatively coupled to an SSH VCN 1612 (e.g., the SSH VCN 1312 of FIG. 13) via an LPG 1610 contained in the SSH VCN 1612. The SSH VCN 1612 can include an SSH subnet 1614 (e.g., the SSH subnet 1314 of FIG. 13), and the SSH VCN 1612 can be communicatively coupled to a control plane VCN 1616 (e.g., the control plane VCN 1316 of FIG. 13) via an LPG 1610 contained in the control plane VCN 1616 and to a data plane VCN 1618 (e.g., the data plane 1318 of FIG. 13) via an LPG 1610 contained in the data plane VCN 1618. The control plane VCN 1616 and the data plane VCN 1618 can be contained in a service tenancy 1619 (e.g., the service tenancy 1319 of FIG. 13).

The control plane VCN 1616 can include a control plane DMZ tier 1620 (e.g., the control plane DMZ tier 1320 of FIG. 13) that can include LB subnet(s) 1622 (e.g., LB subnet(s) 1322 of FIG. 13), a control plane app tier 1624 (e.g., the control plane app tier 1324 of FIG. 13) that can include app subnet(s) 1626 (e.g., app subnet(s) 1326 of FIG. 13), a control plane data tier 1628 (e.g., the control plane data tier 1328 of FIG. 13) that can include DB subnet(s) 1630 (e.g., DB subnet(s) 1530 of FIG. 15). The LB subnet(s) 1622 contained in the control plane DMZ tier 1620 can be communicatively coupled to the app subnet(s) 1626 contained in the control plane app tier 1624 and to an Internet gateway 1634 (e.g., the Internet gateway 1334 of FIG. 13) that can be contained in the control plane VCN 1616, and the app subnet(s) 1626 can be communicatively coupled to the DB subnet(s) 1630 contained in the control plane data tier 1628 and to a service gateway 1636 (e.g., the service gateway of FIG. 13) and a network address translation (NAT) gateway 1638 (e.g., the NAT gateway 1338 of FIG. 13). The control plane VCN 1616 can include the service gateway 1636 and the NAT gateway 1638.

The data plane VCN 1618 can include a data plane app tier 1646 (e.g., the data plane app tier 1346 of FIG. 13), a data plane DMZ tier 1648 (e.g., the data plane DMZ tier 1348 of FIG. 13), and a data plane data tier 1650 (e.g., the data plane data tier 1350 of FIG. 13). The data plane DMZ tier 1648 can include LB subnet(s) 1622 that can be communicatively coupled to trusted app subnet(s) 1660 (e.g., trusted app subnet(s) 1560 of FIG. 15) and untrusted app subnet(s) 1662 (e.g., untrusted app subnet(s) 1562 of FIG. 15) of the data plane app tier 1646 and the Internet gateway 1634 contained in the data plane VCN 1618. The trusted app subnet(s) 1660 can be communicatively coupled to the service gateway 1636 contained in the data plane VCN 1618, the NAT gateway 1638 contained in the data plane VCN 1618, and DB subnet(s) 1630 contained in the data plane data tier 1650. The untrusted app subnet(s) 1662 can be communicatively coupled to the service gateway 1636 contained in the data plane VCN 1618 and DB subnet(s) 1630 contained in the data plane data tier 1650. The data plane data tier 1650 can include DB subnet(s) 1630 that can be communicatively coupled to the service gateway 1636 contained in the data plane VCN 1618.

The untrusted app subnet(s) 1662 can include primary VNICs 1664(1)-(N) that can be communicatively coupled to tenant virtual machines (VMs) 1666(1)-(N) residing within the untrusted app subnet(s) 1662. Each tenant VM 1666(1)-(N) can run code in a respective container 1667(1)-(N), and be communicatively coupled to an app subnet 1626 that can be contained in a data plane app tier 1646 that can be contained in a container egress VCN 1668. Respective secondary VNICs 1672(1)-(N) can facilitate communication between the untrusted app subnet(s) 1662 contained in the data plane VCN 1618 and the app subnet contained in the container egress VCN 1668. The container egress VCN can include a NAT gateway 1638 that can be communicatively coupled to public Internet 1654 (e.g., public Internet 1354 of FIG. 13).

The Internet gateway 1634 contained in the control plane VCN 1616 and contained in the data plane VCN 1618 can be communicatively coupled to a metadata management service 1652 (e.g., the metadata management system 1352 of FIG. 13) that can be communicatively coupled to public Internet 1654. Public Internet 1654 can be communicatively coupled to the NAT gateway 1638 contained in the control plane VCN 1616 and contained in the data plane VCN 1618. The service gateway 1636 contained in the control plane VCN 1616 and contained in the data plane VCN 1618 can be communicatively coupled to cloud services 1656.

In some examples, the pattern illustrated by the architecture of block diagram 1600 of FIG. 16 may be considered an exception to the pattern illustrated by the architecture of block diagram 1500 of FIG. 15 and may be desirable for a customer of the IaaS provider if the IaaS provider cannot directly communicate with the customer (e.g., a disconnected region). The respective containers 1667(1)-(N) that are contained in the VMs 1666(1)-(N) for each customer can be accessed in real-time by the customer. The containers 1667(1)-(N) may be configured to make calls to respective secondary VNICs 1672(1)-(N) contained in app subnet(s) 1626 of the data plane app tier 1646 that can be contained in the container egress VCN 1668. The secondary VNICs 1672(1)-(N) can transmit the calls to the NAT gateway 1638 that may transmit the calls to public Internet 1654. In this example, the containers 1667(1)-(N) that can be accessed in real-time by the customer can be isolated from the control plane VCN 1616 and can be isolated from other entities contained in the data plane VCN 1618. The containers 1667(1)-(N) may also be isolated from resources from other customers.

In other examples, the customer can use the containers 1667(1)-(N) to call cloud services 1656. In this example, the customer may run code in the containers 1667(1)-(N) that requests a service from cloud services 1656. The containers 1667(1)-(N) can transmit this request to the secondary VNICs 1672(1)-(N) that can transmit the request to the NAT gateway that can transmit the request to public Internet 1654. Public Internet 1654 can transmit the request to LB subnet(s) 1622 contained in the control plane VCN 1616 via the Internet gateway 1634. In response to determining the request is valid, the LB subnet(s) can transmit the request to app subnet(s) 1626 that can transmit the request to cloud services 1656 via the service gateway 1636.

It should be appreciated that IaaS architectures 1300, 1400, 1500, 1600 depicted in the figures may have other components than those depicted. Further, the embodiments shown in the figures are only some examples of a cloud infrastructure system that may incorporate an embodiment of the disclosure. In some other embodiments, the IaaS systems may have more or fewer components than shown in the figures, may combine two or more components, or may have a different configuration or arrangement of components.

In certain embodiments, the IaaS systems described herein may include a suite of applications, middleware, and database service offerings that are delivered to a customer in a self-service, subscription-based, elastically scalable, reliable, highly available, and secure manner. An example of such an IaaS system is the Oracle Cloud Infrastructure (OCI) provided by the present assignee.

Figure 17:
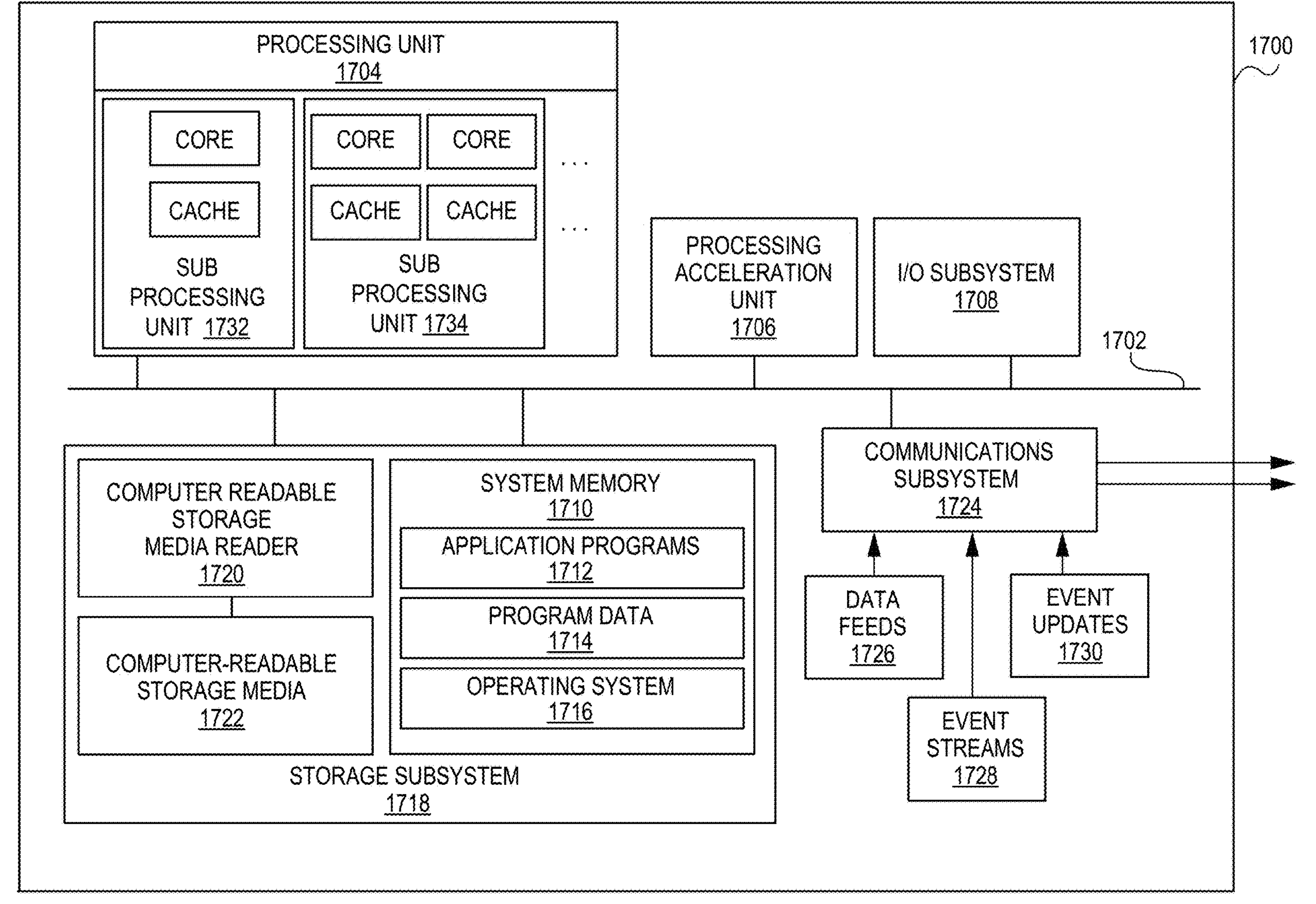
FIG. 17 is a block diagram illustrating an example computer system, according to at least one embodiment

FIG. 17 illustrates an example computer system 1700, in which various embodiments may be implemented. The system 1700 may be used to implement any of the computer systems described above. As shown in the figure, computer system 1700 includes a processing unit 1704 that communicates with a number of peripheral subsystems via a bus subsystem 1702. These peripheral subsystems may include a processing acceleration unit 1706, an I/O subsystem 1708, a storage subsystem 1718 and a communications subsystem 1724. Storage subsystem 1718 includes tangible computer-readable storage media 1722 and a system memory 1710.

Bus subsystem 1702 provides a mechanism for letting the various components and subsystems of computer system 1700 communicate with each other as intended. Although bus subsystem 1702 is shown schematically as a single bus, alternative embodiments of the bus subsystem may utilize multiple buses. Bus subsystem 1702 may be any of several types of bus structures including a memory bus or memory controller, a peripheral bus, and a local bus using any of a variety of bus architectures. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 1704, which can be implemented as one or more integrated circuits (e.g., a conventional microprocessor or microcontroller), controls the operation of computer system 1700. One or more processors may be included in processing unit 1704. These processors may include single core or multicore processors. In certain embodiments, processing unit 1704 may be implemented as one or more independent processing units 1732 and/or 1734 with single or multicore processors included in each processing unit. In other embodiments, processing unit 1704 may also be implemented as a quad-core processing unit formed by integrating two dual-core processors into a single chip.

In various embodiments, processing unit 1704 can execute a variety of programs in response to program code and can maintain multiple concurrently executing programs or processes. At any given time, some or all of the program code to be executed can be resident in processor(s) 1704 and/or in storage subsystem 1718. Through suitable programming, processor(s) 1704 can provide various functionalities described above. Computer system 1700 may additionally include a processing acceleration unit 1706, which can include a digital signal processor (DSP), a special-purpose processor, and/or the like.

I/O subsystem 1708 may include user interface input devices and user interface output devices. User interface input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may include, for example, motion sensing and/or gesture recognition devices such as the Microsoft Kinect® motion sensor that enables users to control and interact with an input device, such as the Microsoft Xbox® 360 game controller, through a natural user interface using gestures and spoken commands. User interface input devices may also include eye gesture recognition devices such as the Google Glass® blink detector that detects eye activity (e.g., 'blinking' while taking pictures and/or making a menu selection) from users and transforms the eye gestures as input into an input device (e.g., Google Glass®). Additionally, user interface input devices may include voice recognition sensing devices that enable users to interact with voice recognition systems (e.g., Siri® navigator), through voice commands.

User interface input devices may also include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, medical ultrasonography devices. User interface input devices may also include, for example, audio input devices such as MIDI keyboards, digital musical instruments and the like.

User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. In general, use of the term "output device" is intended to include all possible types of devices and mechanisms for outputting information from computer system 1700 to a user or other computer. For example, user interface output devices may include, without limitation, a variety of display devices that visually convey text, graphics and audio/video information such as monitors, printers, speakers, headphones, automotive navigation systems, plotters, voice output devices, and modems.

Computer system 1700 may comprise a storage subsystem 1718 that provides a tangible non-transitory computer-readable storage medium for storing software and data constructs that provide the functionality of the embodiments described in this disclosure. The software can include programs, code modules, instructions, scripts, etc., that when executed by one or more cores or processors of processing unit 1704 provide the functionality described above. Storage subsystem 1718 may also provide a repository for storing data used in accordance with the present disclosure.

As depicted in the example in FIG. 17, storage subsystem 1718 can include various components including a system memory 1710, computer-readable storage media 1722, and a computer readable storage media reader 1720. System memory 1710 may store program instructions that are loadable and executable by processing unit 1704. System memory 1710 may also store data that is used during the execution of the instructions and/or data that is generated during the execution of the program instructions. Various different kinds of programs may be loaded into system memory 1710 including but not limited to client applications, Web browsers, mid-tier applications, relational database management systems (RDBMS), virtual machines, containers, etc.

System memory 1710 may also store an operating system 1716. Examples of operating system 1716 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® OS, and Palm® OS operating systems. In certain implementations where computer system 1700 executes one or more virtual machines, the virtual machines along with their guest operating systems (GOSs) may be loaded into system memory 1710 and executed by one or more processors or cores of processing unit 1704.

System memory 1710 can come in different configurations depending upon the type of computer system 1700. For example, system memory 1710 may be volatile memory (such as random access memory (RAM)) and/or non-volatile memory (such as read-only memory (ROM), flash memory, etc.) Different types of RAM configurations may be provided including a static random access memory (SRAM), a dynamic random access memory (DRAM), and others. In some implementations, system memory 1710 may include a basic input/output system (BIOS) containing basic routines that help to transfer information between elements within computer system 1700, such as during start-up.

Computer-readable storage media 1722 may represent remote, local, fixed, and/or removable storage devices plus storage media for temporarily and/or more permanently containing, storing, computer-readable information for use by computer system 1700 including instructions executable by processing unit 1704 of computer system 1700.

Computer-readable storage media 1722 can include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media.

By way of example, computer-readable storage media 1722 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 1722 may include, but is not limited to, Zip® drives, flash memory cards, universal serial bus (USB) flash drives, secure digital (SD) cards, DVD disks, digital video tape, and the like. Computer-readable storage media 1722 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 1700.

Machine-readable instructions executable by one or more processors or cores of processing unit 1704 may be stored on a non-transitory computer-readable storage medium. A non-transitory computer-readable storage medium can include physically tangible memory or storage devices that include volatile memory storage devices and/or non-volatile storage devices. Examples of non-transitory computer-readable storage medium include magnetic storage media (e.g., disk or tapes), optical storage media (e.g., DVDs, CDs), various types of RAM, ROM, or flash memory, hard drives, floppy drives, detachable memory drives (e.g., USB drives), or other type of storage device.

Communications subsystem 1724 provides an interface to other computer systems and networks. Communications subsystem 1724 serves as an interface for receiving data from and transmitting data to other systems from computer system 1700. For example, communications subsystem 1724 may enable computer system 1700 to connect to one or more devices via the Internet. In some embodiments communications subsystem 1724 can include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof)), global positioning system (GPS) receiver components, and/or other components. In some embodiments communications subsystem 1724 can provide wired network connectivity (e.g., Ethernet) in addition to or instead of a wireless interface.

In some embodiments, communications subsystem 1724 may also receive input communication in the form of structured and/or unstructured data feeds 1726, event streams 1728, event updates 1730, and the like on behalf of one or more users who may use computer system 1700.

By way of example, communications subsystem 1724 may be configured to receive data feeds 1726 in real-time from users of social networks and/or other communication services such as Twitter® feeds, Facebook® updates, web feeds such as Rich Site Summary (RSS) feeds, and/or real-time updates from one or more third party information sources.

Additionally, communications subsystem 1724 may also be configured to receive data in the form of continuous data streams, which may include event streams 1728 of real-time events and/or event updates 1730, that may be continuous or unbounded in nature with no explicit end. Examples of applications that generate continuous data may include, for example, sensor data applications, financial tickers, network performance measuring tools (e.g., network monitoring and traffic management applications), clickstream analysis tools, automobile traffic monitoring, and the like.

Communications subsystem 1724 may also be configured to output the structured and/or unstructured data feeds 1726, event streams 1728, event updates 1730, and the like to one or more databases that may be in communication with one or more streaming data source computers coupled to computer system 1700.

Computer system 1700 can be one of various types, including a handheld portable device (e.g., an iPhone® cellular phone, an iPad® computing tablet, a PDA), a wearable device (e.g., a Google Glass® head mounted display), a PC, a workstation, a mainframe, a kiosk, a server rack, or any other data processing system.

Due to the ever-changing nature of computers and networks, the description of computer system 1700 depicted in the figure is intended only as a specific example. Many other configurations having more or fewer components than the system depicted in the figure are possible. For example, customized hardware might also be used and/or particular elements might be implemented in hardware, firmware, software (including applets), or a combination. Further, connection to other computing devices, such as network input/output devices, may be employed. Based on the disclosure and teachings provided herein, a person of ordinary skill in the art will appreciate other ways and/or methods to implement the various embodiments.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or services are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method comprising:

receiving a natural language utterance from a user during a session between the user and a digital assistant;

obtaining a topic context instance for the natural language utterance, wherein the topic context instance is a context variable data structure that comprises one or more context variables;

invoking, based on the one or more context variables within the context variable data structure, a conversation flow between the user and a digital assistant;

generating, by a generative artificial intelligence (GenAI) model, a list comprising an executable action, wherein the generating the list comprises:

identifying the executable action from one or more candidate actions based on the natural language utterance and the topic context instance, deriving, by the GenAI model, one or more parameters from the natural language utterance, the one or more context variables within the context variable data structure, or both, and filling empty argument slots of the executable action with the one or more parameters;

executing the executable action to produce an output, wherein the executing comprises:

determining there is no thread running within the session that is associated with the topic context instance, the executable action, or both, responsive to determining there is no thread running, creating a thread associated with the topic context instance, the executable action, or both, wherein creating the thread comprises specifying a thread identifier for the thread, and wherein the thread maintains the topic context instance, the executable action, or both as a separate context from that of context associated with any other conversations for a distinct conversation between the user and the digital assistant, storing the thread identifier in association with the topic context instance in a context memory store such that the thread maintains state with the topic context instance for the conversation flow, and executing, using the thread, the executable action to obtain the output; and sending the output or a communication derived from the output to the user, wherein the output or the communication derived from the output includes the thread identifier.

2. The computer-implemented method of claim 1, further comprising:

receiving a subsequent natural language utterance from the user during the session between the user and the digital assistant;

obtaining the topic context instance for the subsequent natural language utterance;

invoking, based on the one or more context variables within the context variable data structure, the conversation flow between the user and the digital assistant;

generating, by the GenAI model, another list comprising another executable action, wherein the generating the another list comprises:

identifying the another executable action from one or more candidate actions based on the subsequent natural language utterance and the topic context instance, deriving, by the GenAI model, one or more parameters from the subsequent natural language utterance, the one or more context variables within the context variable structure, or both, and filling empty argument slots of the another executable action with the one or more parameters;

executing the another executable action, wherein the executing comprises:

identifying that the thread running within the session is associated with the topic context instance, the executable action, or both, determining the another executable action should be executed using the thread based on the thread identifier, and executing, using the thread, the another executable action to obtain another output; and sending the another output or a communication derived from the another output to the user, wherein the another output or the communication derived from the another output includes the thread identifier.

3. The computer-implemented method of claim 1, further comprising:

receiving a subsequent natural language utterance from the user during the session between the user and the digital assistant;

obtaining a subsequent topic context instance for the subsequent natural language utterance, wherein the subsequent topic context instance is a context variable data structure that comprises one or more context variables;

invoking, based on the one or more context variables within the context variable data structure of the subsequent topic context instance, a conversation flow between the user and a digital assistant;

generating, by the GenAI model, another list comprising another executable action, wherein the generating the another list comprises:

identifying the another executable action from one or more candidate actions based on the subsequent natural language utterance and the context variable structure of the subsequent topic context instance, deriving, by the GenAI model, one or more parameters from the subsequent natural language utterance, the one or more context variables within the context variable structure of the subsequent topic context instance, or both, and filling empty argument slots of the another executable action with the one or more parameters;

executing the another executable action, wherein the executing comprises:

identifying that the thread running within the session is associated with the topic context instance for the natural language utterance, the executable action, or both, determining there is no thread running within the session that is associated with the subsequent topic context instance for the subsequent natural language utterance, the another executable action, or both, responsive to determining there is no thread running, creating another thread having an identifier associated with the subsequent topic context instance for the subsequent natural language utterance, the another executable action, or both, wherein creating the another thread comprises specifying another thread identifier for the another thread, and wherein the another thread maintains the subsequent topic context instance for the subsequent natural language utterance, the another executable action, or both as a separate context for another distinct conversation between the user and the digital assistant, storing the another thread identifier in association with the subsequent topic context instance in a context memory store such that the another thread maintains state with the subsequent topic context instance for the conversation flow, and executing, using the another thread, the another executable action to obtain another output; and sending the another output or a communication derived from the another output to the user, wherein the another output or the communication derived from the another output includes the another thread identifier.

4. The computer-implemented method of claim 3, further comprising:

responsive to identifying the thread running within the session is associated with the topic context instance for the natural language utterance, the executable action, or both and determining there is no thread running within the session that is associated with the subsequent topic context instance for the subsequent natural language utterance, sending a confirmation communication to the user requesting confirmation of the subsequent natural language utterance, the subsequent topic context instance for the subsequent natural language utterance, or both; and receiving, at the digital assistant, a confirmation utterance from the user that confirms the subsequent natural language utterance, the subsequent topic context instance for the subsequent natural language utterance, or both, wherein responsive to determining there is no thread running and receipt of the confirmation utterance, creating the another thread.

5. The computer-implemented method of claim 1, further comprising:

receiving a message payload comprising: (i) a subsequent utterance or indication of an event, and (ii) application context, associated with an interaction between a user and an application;

identifying an identifier associated with (i) the subsequent utterance or the indication of the event, (ii) the application context, or (iii) both;

determining the identifier associated with the subsequent utterance or the indication of the event, (ii) the application context, or (iii) both is the same identifier associated with the topic context instance, the executable action, or both; and responsive to determining the identifiers are the same, processing the message payload using the thread.

6. The computer-implemented method of claim 1, further comprising:

receiving a message payload comprising: (i) a subsequent utterance or indication of an event, and (ii) application context, associated with an interaction between a user and an application;

identifying an identifier associated with (i) the subsequent utterance or the indication of the event, (ii) the application context, or (iii) both;

determining the identifier associated with (i) the subsequent utterance or the indication of the event, (ii) the application context, or (iii) both is different from an identifier associated with the topic context instance, the executable action, or both; and responsive to determining the identifiers are different, creating another thread having an identifier associated with (i) the subsequent utterance or the indication of the event, (ii) the application context, or (iii) both, wherein the another thread maintains (i) the subsequent utterance or the indication of the event, (ii) the application context, or (iii) both as a separate context for another distinct conversation between the user and the digital assistant; and processing the message payload using the another thread.

7. The computer-implemented method of claim 6, further comprising:

responsive to determining the identifiers are different, sending a confirmation communication to the user requesting confirmation of (i) the subsequent utterance or the indication of the interface action, (ii) the application context, or (iii) both; and receiving, at the digital assistant, a confirmation utterance from the user that confirms (i) the subsequent utterance or the indication of the interface action, (ii) the application context, or (iii) both, wherein responsive to determining the identifiers are different and receipt of the confirmation utterance, creating the another thread.

8. A system comprising:

one or more processors; and one or more computer-readable media storing instructions which, when executed by the one or more processors, cause the system to perform operations comprising:

receiving a natural language utterance from a user during a session between the user and a digital assistant;

obtaining a topic context instance for the natural language utterance, wherein the topic context instance is a context variable data structure that comprises one or more context variables;

invoking, based on the one or more context variables within the context variable data structure, a conversation flow between the user and a digital assistant;

generating, by a generative artificial intelligence (GenAI) model, a list comprising an executable action, wherein the generating the list comprises:

identifying the executable action from one or more candidate actions based on the natural language utterance and the topic context instance, deriving, by the GenAI model, one or more parameters from the natural language utterance, the one or more context variables within the context variable structure, or both, and filling empty argument slots of the executable action with the one or more parameters;

executing the executable action to produce an output, wherein the executing comprises:

determining there is no thread running within the session that is associated with the topic context instance, the executable action, or both, responsive to determining there is no thread running, creating a thread associated with the topic context instance, the executable action, or both, wherein creating the thread comprises specifying a thread identifier for the thread, and wherein the thread maintains the topic context instance, the executable action, or both as a separate context from that of context associated with any other conversations for a distinct conversation between the user and the digital assistant, storing the thread identifier in association with the topic context instance in a context memory store such that the thread maintains state with the topic context instance for the conversation flow, and executing, using the thread, the executable action to obtain the output; and sending the output or a communication derived from the output to the user, wherein the output or the communication derived from the output includes the thread identifier.

9. The system of claim 8, wherein the operations further comprise:

receiving a subsequent natural language utterance from the user during the session between the user and the digital assistant;

obtaining the topic context instance for the subsequent natural language utterance;

invoking, based on the one or more context variables within the context variable data structure, the conversation flow between the user and the digital assistant;

generating, by the GenAI model, another list comprising another executable action, wherein the generating the another list comprises:

identifying the another executable action from one or more candidate actions based on the subsequent natural language utterance and the topic context instance, deriving, by the GenAI model, one or more parameters from the subsequent natural language utterance, the one or more context variables within the context variable structure, or both, and filling empty argument slots of the another executable action with the one or more parameters;

executing the another executable action, wherein the executing comprises:

identifying tha the thread running within the session is associated with the topic context instance, the executable action, or both, determining the another executable action should be executed using the thread based on the thread identifier, and executing, using the thread, the another executable action to obtain another output; and sending the another output or a communication derived from the another output to the user, wherein the another output or the communication derived from the another output includes the thread identifier.

10. The system of claim 8, wherein the operations further comprise:

receiving a subsequent natural language utterance from the user during the session between the user and the digital assistant;

obtaining a subsequent topic context instance for the subsequent natural language utterance, wherein the subsequent topic context instance is a context variable data structure that comprises one or more context variables;

invoking, based on the one or more context variables within the context variable data structure of the subsequent topic context instance, a conversation flow between the user and a digital assistant;

generating, by the GenAI model, another list comprising another executable action, wherein the generating the another list comprises:

identifying the another executable action from one or more candidate actions based on the subsequent natural language utterance and the context variable structure of the subsequent topic context instance, deriving, by the GenAI model, one or more parameters from the subsequent natural language utterance, the one or more context variables within the context variable structure of the subsequent topic context instance, or both, and filling empty argument slots of the another executable action with the one or more parameters;

executing the another executable action, wherein the executing comprises:

identifying that the thread running within the session is associated with the topic context instance for the natural language utterance, the executable action, or both, determining there is no thread running within the session that is associated with the subsequent topic context instance for the subsequent natural language utterance, the another executable action, or both, responsive to determining there is no thread running within the session that is associated with the subsequent topic context instance for the subsequent natural language utterance, creating another thread having an identifier associated with the subsequent topic context instance for the subsequent natural language utterance, the another executable action, or both, wherein creating the another thread comprises specifying another thread identifier for the another thread, and wherein the another thread maintains the subsequent topic context instance for the subsequent natural language utterance, the another executable action, or both as a separate context for another distinct conversation between the user and the digital assistant, storing the another thread identifier in association with the subsequent topic context instance in a context memory store such that the another thread maintains state with the subsequent topic context instance for the conversation flow, and executing, using the another thread, the another executable action to obtain another output; and sending the another output or a communication derived from the another output to the user, wherein the another output or the communication derived from the another output includes the another thread identifier.

11. The system of claim 10, wherein the operations further comprise:

responsive to identifying that the thread running within the session is associated with the topic context instance for the natural language utterance, the executable action, or both and determining there is no thread running within the session that is associated with the subsequent topic context instance for the subsequent natural language utterance, sending a confirmation communication to the user requesting confirmation of the subsequent natural language utterance, the subsequent topic context instance for the subsequent natural language utterance, or both; and receiving, at the digital assistant, a confirmation utterance from the user that confirms the subsequent natural language utterance, the subsequent topic context instance for the subsequent natural language utterance, or both, wherein responsive to determining there is no thread running within the session that is associated with the subsequent topic context instance for the subsequent natural language utterance and receipt of the confirmation utterance, creating the another thread.

12. The system of claim 8, wherein the operations further comprise:

receiving a message payload comprising: (i) a subsequent utterance or indication of an event, and (ii) application context, associated with an interaction between a user and an application;

identifying an identifier associated with the subsequent utterance or the indication of the event, (ii) the application context, or (iii) both;

determining the identifier associated with (i) the subsequent utterance or the indication of the event, (ii) the application context, or (iii) both is the same identifier associated with the topic context instance, the executable action, or both; and responsive to determining the identifiers are the same, processing the message payload using the thread.

13. The system of claim 8, wherein the operations further comprise:

receiving a message payload comprising: (i) a subsequent utterance or indication of an event, and (ii) application context, associated with an interaction between a user and an application;

identifying an identifier associated with (i) the subsequent utterance or the indication of the event, (ii) the application context, or (iii) both;

determining the identifier associated with (i) the subsequent utterance or the indication of the event, (ii) the application context, or (iii) both is different from an identifier associated with the topic context instance, the executable action, or both; and responsive to determining the identifiers are different, creating another thread having an identifier associated with (i) the subsequent utterance or the indication of the event, (ii) the application context, or (iii) both, wherein the another thread maintains (i) the subsequent utterance or the indication of the event, (ii) the application context, or (iii) both as a separate context for another distinct conversation between the user and the digital assistant; and processing the message payload using the another thread.

14. The system of claim 13, wherein the operations further comprise:

responsive to determining the identifiers are different, sending a confirmation communication to the user requesting confirmation of (i) the subsequent utterance or the indication of the event, (ii) the application context, or (iii) both; and receiving, at the digital assistant, a confirmation utterance from the user that confirms (i) the subsequent utterance or the indication of the event, (ii) the application context, or (iii) both, wherein responsive to determining the identifiers are different and receipt of the confirmation utterance, creating the another thread.

15. One or more non-transitory computer-readable media storing instructions which, when executed by one or more processors, cause the one or more processors to perform operations comprising:

receiving a natural language utterance from a user during a session between the user and a digital assistant;

obtaining a topic context instance for the natural language utterance, wherein the topic context instance is a context variable data structure that comprises one or more context variables;

invoking, based on the one or more context variables within the context variable data structure, a conversation flow between the user and a digital assistant;

generating, by a generative artificial intelligence (GenAI) model, a list comprising an executable action, wherein the generating the list comprises:

identifying the executable action from one or more candidate actions based on the natural language utterance and the topic context instance, deriving, by the GenAI model, one or more parameters from the natural language utterance, the one or more context variables within the context variable data structure, or both, and filling empty argument slots of the executable action with the one or more parameters;

executing the executable action to produce an output, wherein the executing comprises:

determining there is no thread running within the session that is associated with the topic context instance, the executable action, or both, responsive to determining there is no thread running, creating a thread associated with the topic context instance, the executable action, or both, wherein creating the thread comprises specifying a thread identifier for the thread, and wherein the thread maintains the topic context instance, the executable action, or both as a separate context from that of context associated with any other conversations for a distinct conversation between the user and the digital assistant, storing the thread identifier in association with the topic context instance in a context memory store such that the thread maintains state with the topic context instance for the conversation flow, and executing, using the thread, the executable action to obtain the output; and sending the output or a communication derived from the output to the user, wherein the output or the communication derived from the output includes the thread identifier.

16. The one or more non-transitory computer-readable media of claim 15, wherein the operations further comprise:

receiving a subsequent natural language utterance from the user during the session between the user and the digital assistant;

obtaining the topic context instance for the subsequent natural language utterance;

invoking, based on the one or more context variables within the context variable data structure, the conversation flow between the user and the digital assistant;

generating, by the GenAI model, another list comprising another executable action, wherein the generating the another list comprises:

identifying the another executable action from one or more candidate actions based on the subsequent natural language utterance and the topic context instance, deriving, by the GenAI model, one or more parameters from the subsequent natural language utterance, the one or more context variables within the context variable structure, or both, and filling empty argument slots of the another executable action with the one or more parameters;

executing the another executable action, wherein the executing comprises:

identifying that the thread running within the session is associated with the topic context instance, the executable action, or both, determining the another executable action should be executed using the thread based on the thread identifier, and executing, using the thread, the another executable action to obtain another output; and sending the another output or a communication derived from the another output to the user, wherein the another output or the communication derived from the another output includes the thread identifier.

17. The one or more non-transitory computer-readable media of claim 15, wherein the operations further comprise:

receiving a subsequent natural language utterance from the user during the session between the user and the digital assistant;

obtaining a subsequent topic context instance for the subsequent natural language utterance, wherein the subsequent topic context instance is a context variable data structure that comprises one or more context variables;

invoking, based on the one or more context variables within the context variable data structure of the subsequent topic context instance, a conversation flow between the user and a digital assistant;

generating, by the GenAI model, another list comprising another executable action, wherein the generating the another list comprises:

identifying the another executable action from one or more candidate actions based on the subsequent natural language utterance and the context variable structure of the subsequent topic context instance, deriving, by the GenAI model, one or more parameters from the subsequent natural language utterance, the one or more context variables within the context variable structure of the subsequent topic context instance, or both, and filling empty argument slots of the another executable action with the one or more parameters;

executing the another executable action, wherein the executing comprises:

identifying that the thread running within the session is associated with the topic context instance for the natural language utterance, the executable action, or both, determining there is no thread running within the session that is associated with the subsequent topic context instance for the subsequent natural language utterance, the another executable action, or both, responsive to determining there is no thread running within the session that is associated with the subsequent topic context instance for the subsequent natural language utterance, creating another thread having an identifier associated with the subsequent topic context instance for the subsequent natural language utterance, the another executable action, or both, wherein creating the another thread comprises specifying another thread identifier for the another thread, and wherein the another thread maintains the subsequent topic context instance for the subsequent natural language utterance, the another executable action, or both as a separate context for another distinct conversation between the user and the digital assistant, storing the another thread identifier in association with the subsequent topic context instance in a context memory store such that the another thread maintains state with the subsequent topic context instance for the conversation flow, and executing, using the another thread, the another executable action to obtain another output; and sending the another output or a communication derived from the another output to the user, wherein the another output or the communication derived from the another output includes the another thread identifier.

18. The one or more non-transitory computer-readable media of claim 17, wherein the operations further comprise:

responsive to identifying that the thread running within the session is associated with the topic context instance for the natural language utterance, the executable action, or both and determining there is no thread running within the session that is associated with the subsequent topic context instance for the subsequent natural language utterance, sending a confirmation communication to the user requesting confirmation of the subsequent natural language utterance, the subsequent topic context instance for the subsequent natural language utterance, or both; and receiving, at the digital assistant, a confirmation utterance from the user that confirms the subsequent natural language utterance, the subsequent topic context instance for the subsequent natural language utterance, or both, wherein responsive to determining there is no thread running within the session that is associated with the subsequent topic context instance for the subsequent natural language utterance and receipt of the confirmation utterance, creating the another thread.

19. The one or more non-transitory computer-readable media of claim 15, wherein the operations further comprise:

receiving a message payload comprising: (i) a subsequent utterance or indication of an event, and (ii) application context, associated with an interaction between a user and an application;

identifying an identifier associated with (i) the subsequent utterance or the indication of the event, (ii) the application context, or (iii) both;

determining the identifier associated with (i) the subsequent utterance or the indication of the event, (ii) the application context, or (iii) both is the same identifier associated with the topic context instance, the executable action, or both; and responsive to determining the identifiers are the same, processing the message payload using the thread.

20. The one or more non-transitory computer-readable media of claim 15, wherein the operations further comprise:

receiving a message payload comprising: (i) a subsequent utterance or indication of an event, and (ii) application context, associated with an interaction between a user and an application;

identifying an identifier associated with (i) the subsequent utterance or the indication of the event, (ii) the application context, or (iii) both;

determining the identifier associated with (i) the subsequent utterance or the indication of the event, (ii) the application context, or (iii) both is different from an identifier associated with the topic context instance, the executable action, or both; and responsive to determining the identifiers are different, creating another thread having an identifier associated with (i) the subsequent utterance or the indication of the interface action, (ii) the application context, or (iii) both, wherein the another thread maintains (i) the subsequent utterance or the indication of the event, (ii) the application context, or (iii) both as a separate context for another distinct conversation between the user and the digital assistant; and processing the message payload using the another thread.

* * * * *